United States Patent
Ng et al.

(10) Patent No.: US 9,572,892 B2
(45) Date of Patent: Feb. 21, 2017

(54) POLYMER CONJUGATE FOR DELIVERY OF A BIOACTIVE AGENT

(71) Applicant: POLYACTIVA PTY LTD, Melbourne, Victoria (AU)

(72) Inventors: Sarah Man Yee Ng, Berwick (AU); Andrew Craig Donohue, Bentleigh East (AU); Russell John Tait, Balwyn (AU); Stephen Lonsdale Birkett, West Brunswick (AU); Adrian Sulistio, Glen Iris (AU); Anton Blencowe, Adelaide (AU)

(73) Assignee: POLYACTIVA PTY LTD, Melbourne, Victoria (AU)

( * ) Notice: Subject to any disclaimer, the term of this patent is extended or adjusted under 35 U.S.C. 154(b) by 0 days.

(21) Appl. No.: 14/772,981

(22) PCT Filed: Mar. 7, 2014

(86) PCT No.: PCT/AU2014/000231
§ 371 (c)(1),
(2) Date: Sep. 4, 2015

(87) PCT Pub. No.: WO2014/134689
PCT Pub. Date: Sep. 12, 2014

(65) Prior Publication Data
US 2016/0000929 A1 Jan. 7, 2016

(30) Foreign Application Priority Data

Mar. 8, 2013 (AU) ................................ 2013900883

(51) Int. Cl.
*C08G 73/00* (2006.01)
*A61K 47/48* (2006.01)
(Continued)

(52) U.S. Cl.
CPC ....... *A61K 47/48176* (2013.01); *A61K 9/0051* (2013.01); *A61K 31/5377* (2013.01);
(Continued)

(58) Field of Classification Search
CPC . C08G 73/08; C08G 2261/3221; C08G 12/28; A61K 47/48; A61K 31/5575
See application file for complete search history.

(56) References Cited

U.S. PATENT DOCUMENTS

| 4,228,152 A | 10/1980 | Ferruti et al. |
| 2011/0319487 A1 | 12/2011 | Mercier |
| 2014/0120058 A1 | 5/2014 | O'Shea et al. |

FOREIGN PATENT DOCUMENTS

| WO | WO 2010/040188 A1 | 4/2010 |
| WO | WO 2010/141507 A1 | 12/2010 |
| WO | WO 2012/075117 A2 | 6/2012 |

OTHER PUBLICATIONS

Gao et al. Bioconjugate Chem. 2011, 22, 1153-1161.*
(Continued)

*Primary Examiner* — Shane Fang
(74) *Attorney, Agent, or Firm* — Foley & Lardner LLP

(57) ABSTRACT

The present invention relates in general to polymer-bioactive agent conjugates for delivering a bioactive agent to a subject. The polymer-bioactive agent conjugates contain triazole moieties in the polymer backbone and a bioactive moiety selected from prostaglandin analogs, β-blockers and mixtures thereof. The present invention also relates to methods for preparing the polymer conjugates using click chemical reactions, to monomer-bioactive agent conjugates suitable for preparing the polymer conjugates, and to pharmaceutical products comprising the polymer conjugates for the treatment of glaucoma.

24 Claims, 2 Drawing Sheets

(51) Int. Cl.
A61K 9/00 (2006.01)
A61K 31/5377 (2006.01)
A61K 31/5575 (2006.01)

(52) U.S. Cl.
CPC .... *A61K 31/5575* (2013.01); *A61K 47/48192* (2013.01); *A61K 47/48215* (2013.01)

(56) References Cited

OTHER PUBLICATIONS

International Search Report issued on May 26, 2014 in application No. PCT/AU2014/000231.
Gao et al., "Linear Cationic Click Polymer for Gene Delivery: Synthesis, Biocompatibility, and in Vitro Transfection," Biomacromolecules, vol. 11, No. 11, pp. 3102-3111, Nov. 2010.
Meudtner et al., "Responsive Backbones Based on Alternating Triazole-Pyridine/Benzene Copolymers: From Helically Folding Polymers to Metallosupramolecularly Crosslinked Gels," Macromolecular Rapid Communications, vol. 29, No. 4, pp. 347-351, Feb. 2008.
Efthymiou et al., "Efficient synthesis and cell-based silencing activity of siRNAs that contain triazole backbone linkages," Bioorganic & Medicinal Chemistry Letters, vol. 22, No. 4, pp. 1722-1726, Feb. 2012.
Supplementary European Search Report issued on Oct. 20, 2016 in application No. EP 14 76 0322.

\* cited by examiner

POLYMER CONJUGATE FOR DELIVERY OF A BIOACTIVE AGENT

FIELD OF THE INVENTION

The present invention relates in general to polymer-bioactive agent conjugates for delivering a bioactive agent to a subject. In particular, the present invention relates to polymer-bioactive agent conjugates containing triazole moieties in the polymer backbone for delivering a bioactive agent selected from prostaglandin analogues and β-blockers. The present invention also relates to methods for preparing the polymer conjugates by means of alkyne/azide cycloaddition reactions ("click chemical reactions"), to monomer-bioactive agent conjugates suitable for preparing the polymer conjugates, and to pharmaceutical products comprising the polymer conjugates for the treatment of glaucoma.

BACKGROUND

Polymer-bioactive agent conjugates containing a bioactive agent covalently bound to a polymer are of interest for the targeted and controlled delivery of therapeutic agents. In the treatment of many different conditions, the site-specific delivery of a drug directly to or near a desired site of action in the body of a subject can be highly desirable to improve the efficacy and/or safety of the drug. Certain sites in a subject may require sophisticated delivery vehicles to overcome barriers for effective drug delivery. For example, the eye has a limited volume for administration and requires a pharmaceutical product with a high drug loading to ensure that adequate doses of drug can be delivered while keeping product volume to a minimum. Despite the limited volume it is desirable to be able to deliver drug to the site continuously and in a controlled manner over an extended period of time.

β-blockers are antagonists of beta-adrenoreceptor sites and are used to treat or manage a range of conditions, including cardiac arrhythmias, hypertension, hypotension and glaucoma. Elevated intraocular pressure (ocular hypertension) is a risk factor for glaucoma. β-blockers can reduce intraocular pressure and exert an ocular hypotensive effect by reducing the production of aqueous humour in the eye.

Prostaglandin analogues are molecules designed to bind to a prostaglandin receptor and are used to treat gastrointestinal acid related disorders such as duodenal and gastric ulcers, as abortifacients or uterotonics to induce labour or prevent past partum haemorrhage, and to treat ocular hypertension. Prostaglandin analogues exert an ocular hypotensive effect by increasing uveoscleral outflow of aqueous humour.

Prostaglandin analogues and β-blockers used in the treatment of glaucoma are presently formulated as eye drops, which if administered conscientiously to the affected eye will lower intraocular pressure. This in turn can slow the progression of glaucoma. The prostaglandin analogues and β-blockers are administered as eye drops, either alone (i.e. as a single agent) or in combination. It is postulated that combining prostaglandin analogues with β-blockers that exert their effect through a different mechanism, may provide an additive effect in reducing intraocular pressure. For example, some pharmaceutical preparations used in the treatment of glaucoma, such as Xalacom™ eye drops marketed by Pfizer and Ganfort™ eye drops marketed by Allergan, contain a prostaglandin analogue in combination with a β-blocker.

Unfortunately, as glaucoma is an asymptomatic disease many patients do not use their drops conscientiously, compromising therapy. A recent study by Friedman et al. (Friedman et al. *IOVS* 2007: 48, 5052-5057) showed that adherence to glaucoma treatment options is poor with only 59% of patients in possession of an ocular hypotensive agent at 12 months, and only 10% of patients used such medication continuously. Patient compliance in glaucoma therapy is therefore an issue.

Drug delivery systems have been developed to aid in the administration and/or sustained delivery of bioactive agents (such as drugs) to a desired site of action. One mode of delivering a drug to a subject involves the use of a polymer in association with the drug so that it can be delivered to and/or retained at a specific location.

One form of a polymer/drug delivery system utilises an admixture of a polymer with a drug, where the drug is blended with the polymer matrix. However, such admixtures generally result in poor control over the release of the drug, with a "burst effect" often occurring immediately after administration and significant changes in the physical properties of the admixture occurring as the drug is released (Sjoquist, B.; Basu, S.; Byding, P.; Bergh, K.; Stjernschantz, J. *Drug Metab. Dispos.* 1998, 26, 745.). In addition, such admixtures have limited dose loading capacity, resulting in a prohibitively large device for convenient administration to some sites in a subject.

Another form of a polymer/drug delivery system is based on the polymerisation of a drug so as to incorporate the drug molecule as part of the backbone of a polymer chain. Such a system is described in U.S. Pat. No. 6,613,807, WO2008/128193, WO94/04593 and U.S. Pat. No. 7,122,615. However, such polymer systems generally provide inefficient delivery of the drug, as release of the drug relies on breakdown of the polymer backbone. Furthermore, breakdown of the polymer backbone produces inactive intermediates. Such intermediates can complicate regulatory approval, which may require the safety of the intermediates to be demonstrated.

Another approach for preparing polymer-bioactive agent conjugates involves the covalent attachment of bioactive agent molecules to a pre-formed polymer backbone. Examples of such polymer conjugates have been reviewed in *Nature Reviews: Drug Discovery* 2003: 2, 347-360. However, this approach can also be problematic. In particular, steric and thermodynamic constraints can affect the amount of bioactive agent that can be covalently attached, and also impact on the distribution of the bioactive agent along the polymer backbone. These factors can, in turn, reduce control over the release of the bioactive agent. Furthermore, the use of a pre-formed polymer backbone provides limited scope for modification of the polymer conjugate after attachment of the bioactive agent should the properties of the conjugate need to be adjusted to improve drug release and/or to aid patient comfort, particularly in the eye.

For efficient delivery, bioactive agents such as drugs are ideally pendant from the backbone polymer chain.

In preparing polymer-bioactive agent conjugates, step-growth polymerisation is one approach that has been used. By means of step-growth polymerisation, polymer-bioactive agent conjugates can be prepared by covalently reacting a bioactive agent-functionalised monomer having at least two terminal reactive functional groups, with a co-monomer of complementary terminal functionality. An example is the reaction of a drug-functionalised dihydroxy monomer with a diisocyanate co-monomer to form a polymer-drug conjugate with a polyurethane polymer backbone. However, one problem with step-growth polymerisation methods is that many bioactive agents, such as drug molecules, can contain multiple functional groups that are capable of participating in the covalent reactions used to form the polymer. In such circumstances, there is a risk that a functional group on a drug molecule could react with a terminal functional group of a monomer, leading to intra-chain incorporation of the bioactive agent in the polymer. As a result, the bioactive agent becomes part of the polymer backbone structure, rather than forming a pendant group. Prostaglandin analogues and β-blockers are examples of such drugs with multiple nucleophilic functional groups with a consequential high risk of in-chain incorporation.

It would be desirable to provide new polymer-bioactive agent conjugates, which address or ameliorate one or more disadvantages or shortcomings associated with existing materials and/or their method of manufacture, or to at least provide a useful alternative to such materials and their method of manufacture.

SUMMARY OF THE INVENTION

The present invention provides in one aspect, a polymer-bioactive agent conjugate comprising a polymer backbone comprising a plurality of triazole moieties, and a plurality of releasable bioactive agents covalently bonded to and pendant from the polymer backbone, wherein the bioactive moieties are selected from the group consisting of prostaglandin analogues, β-blockers, and mixtures thereof.

Polymer-bioactive agent conjugates of the invention are obtained through the use of click chemistry, in particular through the application of variants of the Huisgen 1,3 dipolar cycloaddition of azides and alkynes. With click chemistry, at least two co-monomers of appropriate complementary terminal functionality covalently react to form the polymer-bioactive agent conjugate. At least one of the co-monomers carries a pendant bioactive agent. The triazole moieties present in the polymer backbone of the polymer-bioactive agent conjugate are reaction products obtained from the covalent coupling of terminal functional groups present on the co-monomers. Thus, the covalent reaction between the co-monomers results in the formation of a polymer-bioactive agent conjugate comprising a polymer backbone and bioactive agents pendant from the polymer backbone, together with triazole moieties in the polymer backbone structure.

In some embodiments, polymer-bioactive agent conjugates of the invention comprise a moiety of formula (I):

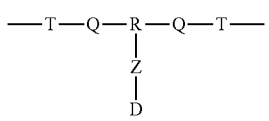

where:
T at each occurrence represents a triazole moiety;
Q is independently selected at each occurrence and may be present or absent and when present represents a linking group;
R is an optionally substituted linear or branched hydrocarbon and may comprise optionally substituted aromatic hydrocarbon or heteroaromatic hydrocarbon
Z is a cleavable linking group; and
D is a releasable bioactive agent.

In some embodiments, polymer-bioactive agent conjugates of the invention comprise a moiety of formula (Ib);

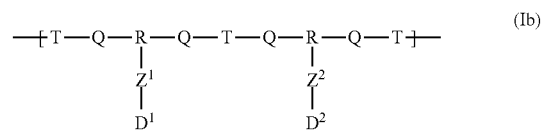

where:
T at each occurrence represents a triazole moiety;
Q is independently selected at each occurrence may be present or absent and when present represents a linking group;
R is an optionally substituted linear or branched hydrocarbon and may comprise optionally substituted aromatic hydrocarbon and or heteroaromatic hydrocarbon;
$Z^1$ and $Z^2$ are each cleavable linking groups that may be the same or different; and
$D^1$ and $D^2$ are each releasable bioactive agents that may be the same or different.

In formulae (I) and (Ib), the bioactive agent is selected from the group consisting of prostaglandin analogues, β-blockers, and mixtures thereof.

Triazole moieties present in the polymer backbone of the polymer-bioactive agent conjugates, which are the product of an azide/alkyne coupling, are 1,2,3-triazole moieties.

In some embodiments, the polymer backbone of the polymer-bioactive agent conjugate comprises at least one triazole moiety selected from the group consisting of formula (II), (III) and (IX):

wherein in formula (IX), A represents an optionally substituted cyclic group, preferably a cyclic group comprising from 7 to 9 ring atoms.

In some embodiments, the polymer-bioactive agent conjugate comprises at least one moiety selected from formula (IIa) and (IIb):

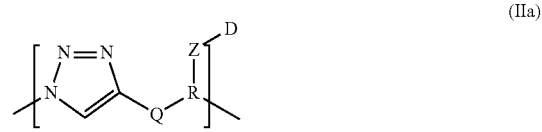

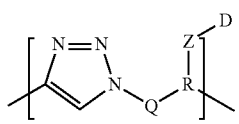

(IIb)

In some embodiments, the polymer-bioactive agent conjugate comprises at least one moiety selected from formula (IIIa) and (IIIb):

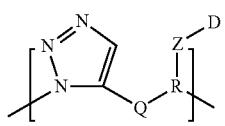

(IIIa)

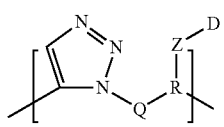

(IIIb)

In one set of embodiments the triazole unit T is of formula IV

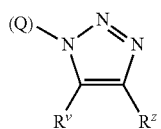

IV wherein:
either
A. one of $R^v$ and $R^z$ is (Q) and the other is hydrogen; or
B. $R^v$ and $R^z$ together complete a ring of from 7 to 9 constitutent ring members selected from the group consisting of carbon and from 0 to 2 heteroatom groups selected from sulfur and the group N—$R^t$ wherein $R^t$ is hydrogen, $C_1$ to $C_6$ alkyl or the group (Q) and wherein the ring is optionally substituted with at least one substituent selected from the group consisting of:
hydroxyl (preferably from 0 to 2 hydroxy);
oxo (i.e. =O) (preferably 0 or 1 oxo group);
halo (preferably from 0 to 2 halo selected from chloro, bromo and fluoro and most preferably fluoro);
$C_1$ to $C_6$ alkoxy (preferably from 0 to 2 $C_1$ to $C_6$ alkoxy); and
rings fused with said ring of 7 to 9 constituent members wherein said fused rings include 0 to 3 rings each fused with said 7 to 9 membered ring and selected from benzene, cyclopropanone, and cyclopropanewherein the fused benzene and cyclopropane rings are optionally further substituted with from one to three substituents selected from the group consisting of $C_1$ to $C_6$ alkyl, halo (preferably from 0 to 2 halo selected from chloro, bromo and fluoro and most preferably fluoro) and $C_1$ to $C_6$ alkoxy;
and wherein at least one ring member selected from nitrogen and carbon is substituted by the further Q polymer unit.

In some embodiments, the polymer-bioactive agent conjugate comprises at least one moiety of formula (IX):

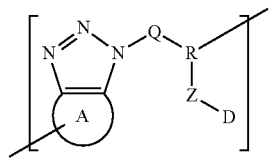

(IXa)

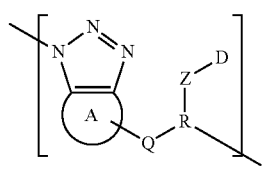

(IXb)

wherein the ring "A" may be said ring of from 7 to 9 constitutent ring members.

Co-monomers useful for the preparation of polymer-bioactive conjugates of the invention comprise terminal functional groups comprising an alkyne and/or an azide. One skilled in the relevant art would understand that under appropriate reaction conditions, an alkyne and an azide containing functional groups can covalently react to form a triazole moiety. Click reaction conditions have been described in for example, Chem. Rev. 2008, 108, 2952, Angew Chem Int Ed 2001, 40, 2004, Angew Chem Int Ed Engl. 2002, Jul. 15, 41(14): 2596-9, Aldrichimica Acta 2010, 43 (1) 15 and *Accounts of Chemical Research* 44 (9): 666-676

In accordance with one form of the invention, the triazole moieties constitute at least 10 mol % of the polymer backbone of the polymer-bioactive agent conjugates. In some embodiments, the triazole moieties constitute at least 20 mol % of the polymer backbone.

A polymer-bioactive agent conjugate according to one aspect of the invention comprises a bioactive agent selected from prostaglandin analogues. The prostaglandin analogue is preferably an analogue of the PGF2α class of prostaglandin. The prostaglandin analogue is conjugated to the polymer backbone at a position selected from the 1, 9, 11 and 15 position of the prostaglandin analogue. The prostaglandin analogue may be conjugated to the polymer backbone via an ester, anhydride or carbonate linking group.

In one set of embodiments, the bioactive agent is a prostaglandin analogue of formula (X):

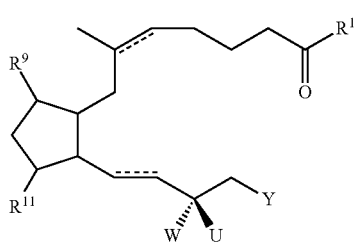

(X)

where:
------ represents a double or single bond;
W and U are selected from the group consisting of where W and U together form oxo (=O), where W and U are each halo, and where W is $R^{15}$ and U is hydrogen;
$R^y$ is an optional substituent selected from the group consisting of oxo and hydroxy;

Y is optionally substituted $C_4$ to $C_{10}$ hydrocarbyl or optionally substituted $C_4$ to $C_{10}$ hydrocarbyloxy; and one of $R^1$, $R^9$, $R^{11}$ and $R^{15}$ is linked to the polymer backbone and wherein:

$R^9$, $R^{11}$ and $R^{15}$ when linked to the polymer backbone are the alcohol residue of an ester or carbonate linking group and $R^1$ when linked to the polymer backbone forms the acid residue of an ester or anhydride linking group; and $R^1$ when not linked to the backbone is selected from the group consisting of —OH, —O($C_{1-6}$ alkyl), and —$NR^aR^b$ where $R^a$ and $R^b$ are each independently selected from the group consisting of H and $C_{1-6}$ alkyl;

$R^9$ and $R^{11}$ when not linked to the polymer backbone are each hydroxy and where one of $R^9$ and $R^{11}$ is linked to the backbone, the other is hydroxy; and when $R^{15}$ is not linked to the backbone then W is hydroxy and U is hydrogen, or W and U are each fluoro, or W and U together form oxo.

In some embodiments, the prostaglandin analogue is selected from the group consisting of:

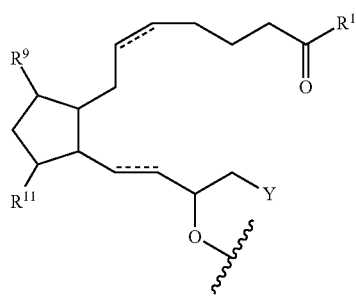
(Xa)

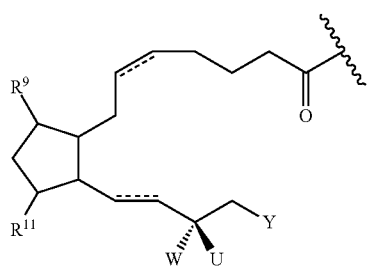
(Xb)

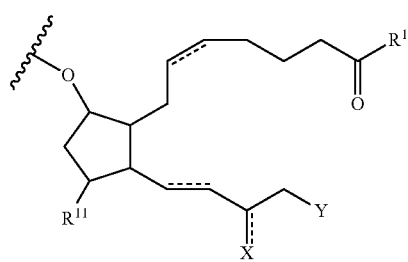
(Xc)

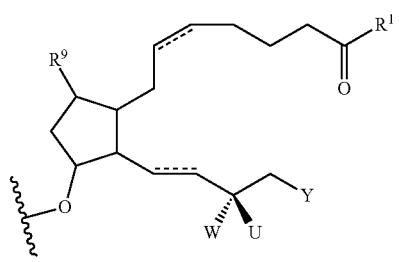
(Xd)

wherein:

〜〜〜 represents the point of attachment of the prostaglandin analogue to linking group Z;

===== represents a double or single bond;

Y is optionally substituted $C_4$ to $C_{10}$ hydrocarbyl or optionally substituted $C_4$ to $C_{10}$ hydrocarbyloxy;

in formulae (Xa), (Xc) and (Xd) $R^1$ is hydroxy, $C_1$ to $C_6$ alkoxy or $C_1$ to $C_6$ alkylamino (preferably, isopropoxy or ethylamino);

in formulae (Xa) and (Xb) $R^9$ and $R^{11}$ are hydroxy;

in formula (Xc) $R^{11}$ is hydroxy and X is O or hydroxy;

in formula (Xd) $R^9$ is hydroxy; and in formulae (Xb) and (Xd) W is hydroxy and U is hydrogen, or W and U are both fluoro, or W and U together form oxo.

Some specific examples of releasable prostaglandin analogues of formulae described herein are latanoprost, travoprost, bimatoprost and tafluprost, the free acid forms of latanoprost, travoprost (known as fluprostenol), bimatoprost and tafluprost, as well as carboprost, unoprostone and dinoprost.

A polymer-bioactive agent conjugate according to one aspect of the invention comprises a bioactive agent selected from β-blockers. The β-blocker analogue is preferably a beta-amino alcohol β-adrenergic antagonist. The β-blocker may be conjugated to the polymer backbone via an ester or carbonate linking group formed with the alcohol moiety of the beta-amino alcohol group.

In one set of embodiments the bioactive agent (D) is a β-blocker of formula (XX):

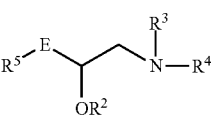
(XX)

wherein;

E is a bond or —$OCH_2$— (preferably —$OCH_2$—);

$R^2$ is linked to the polymer backbone and is the alcohol residue of an ester or carbonate linking group;

$R^3$ and $R^4$ are each independenly selected from the group consisting of H, and linear or branched $C_1$-$C_4$ alkyl optionally substituted by one or more substituents selected from the group consisting of hydroxy, optionally substituted alkoxy, optionally substituted aryloxy, optionally substituted amido, optionally substituted cycloalkyl, and optionally substituted aryl; (preferably $R^3$ is H and $R^4$ is isopropyl or tert-butyl); and $R^5$ is an optionally substituted cycloalkyl or aryl moiety (including polycyclic moieties).

In one set of embodiments of formula (XX), $R^5$ may be selected from the group consisting of 4-morpholin-4-yl-1, 2,5-thiadiazol-3-yl, [2-(cyclopropylmethoxy)ethyl]-phenyl, 3,4-dihydronaphthalen-1(2H)-one, 4-phenyl-acetamide, 1-napthyl, and 4-(2-methoxyethyl)phenyl In some embodiments, the n-blocker is of formula (XXb):

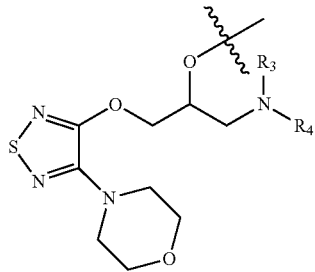

(XXb)

wherein:

⁓⁓⁓ represents the point of attachment of the β-blocker to the ester or carbonate linking group conjugating the drug to the polymer backbone;

$R^3$ and $R^4$ are each independently selected from the group consisting of H, and linear or branched $C_1$-$C_4$ alkyl optionally substituted by one or more substituents selected from the group consisting of hydroxy, optionally substituted alkoxy, optionally substituted aryloxy, optionally substituted amido, optionally substituted cycloalkyl, and optionally substituted aryl (preferably $R^3$ is H and $R^4$ is isopropyl or tert-butyl).

In some embodiments, the β-blocker is of formula (XXc):

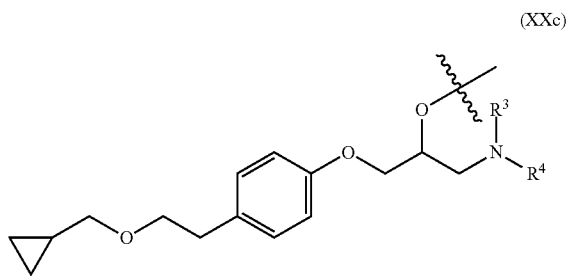

(XXc)

wherein:

⁓⁓⁓ represents the point of attachment of the β-blocker to the ester or carbonate linking group conjugating the drug to the polymer backbone;

$R^3$ and $R^4$ are each independently selected from the group consisting of H, and linear or branched $C_1$-$C_4$ alkyl optionally substituted by one or more substituents selected from the group consisting of hydroxy, optionally substituted alkoxy, optionally substituted aryloxy, optionally substituted amido, optionally substituted cycloalkyl, and optionally substituted aryl (preferably $R^3$ is H and $R^4$ is isopropyl or tert-butyl).

Some specific examples of releasable β-blockers of formulae described herein are betaxolol, carteolol, levobunolol, metripranolol, and timolol.

In some embodiments, a polymer-bioactive agent conjugate according to the invention is a copolymer of at least one monomer of formula (IV):

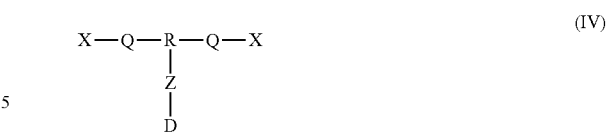

(IV)

where:

X may be the same or different at each occurrence and represents a terminal functional group comprising an alkyne or an azide;

Q is independently selected at each occurrence and may be present or absent and when present, represents a linking group;

R is an optionally substituted linear or branched hydrocarbon and may comprise optionally substituted aromatic hydrocarbon or heteroaromatic hydrocarbon Z is a cleavable linking group; and D is a bioactive agent selected from prostaglandin analogues and β-blockers;

with at least one monomer of formula (V):

(V)

where:

A may be the same or different at each occurrence and represents a group comprising a terminal functional group comprising an alkyne or an azide, wherein said terminal functional group is complementary to the terminal functional group of X;

L is an optionally substituted linker group; and n is an integer and is at least 1.

The moieties of formula (I), (II), (Ill) and (IX) can be produced when monomers of formula (IV) and formula (V) react under click chemistry conditions. Such moieties of formula (I), (II), (III) and (IX) therefore form part of the structure of the backbone polymer chain.

In some embodiments, polymer-bioactive agent conjugates of the invention are formed with a monomer of formula (V), where L is a linker group comprising a linker moiety selected from the group consisting of optionally substituted linear or branched aliphatic hydrocarbon, optionally substituted carbocyclyl, optionally substituted heterocyclyl, optionally substituted aryl, optionally substituted heteroaryl, and an optionally substituted polymeric segment.

In some embodiments of a monomer of formula (V), L comprises a biodegradable polymer. Biodegradable polymers may include at least one biodegradable moiety selected from the group consisting of an ester, an amide, a urethane, a urea and a disulfide moiety.

In some embodiments of a monomer of formula (V). L comprises a polymer selected from the group consisting of a polyether, a polyester, a polyamide, a polyurethane, and copolymers thereof.

In some embodiments of a monomer of formula (V), L comprises a functional group selected from the group consisting of an amide, ether, ester, urethane, urea, and carbonate ester.

In some embodiments of a monomer of formula (V), n is 1 or 2.

In some embodiments of a monomer of formula (IV), Q is present and said Q comprises a functional group selected from the group consisting of an amide, ether, ester, urethane, urea, and carbonate ester functional group.

In some embodiments of a monomer of formula (IV), Q is present and each Q-X is independently selected from the following group:

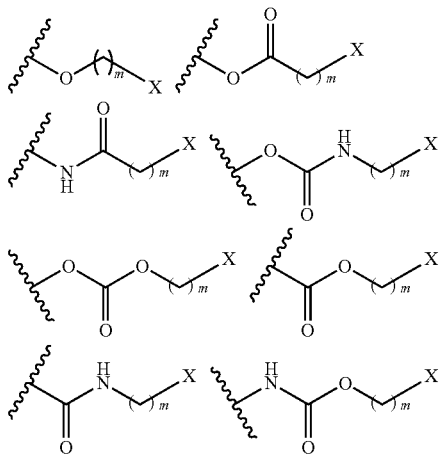

In some embodiments of a monomer of formula (IV), each Q-X is a group of formula (VII):

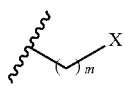

(VII)

where:

X is a terminal functional group selected from the group consisting of an alkyne and an azide; and m is an integer in the range of from 0 to 10, preferably in the range of from 1 to 5.

In some embodiments of a monomer of formula (IV), R is an optionally substituted linear or branched hydrocarbon having from 1 to 12 carbon atoms.

In some embodiments, polymer-bioactive agent conjugates of the invention are formed when at least one monomer of formula (IV) is reacted with a monomer for formula (V) such that the drug is pendant to a triazole-containing polymer backbone according to formula (I).

In one form of the invention, two or more monomers of formula (IV) are reacted with a monomer of formula (V). In such embodiments, the monomers of formula (IV) may contain different bioactive agents (D), such that the resulting polymer conjugate contains a mixture of different bioactive agents. The different bioactive agents may, for example, be a mixture of a prostaglandin analogue and a β-blocker.

In some embodiments, polymer-bioactive agent conjugates of the invention are formed when a monomer of formula (IV) is reacted with a complementary monomer of formula (IV) such that the bioactive agent is pendant to a triazole-containing polymer backbone according to formula (Ib).

In some embodiments, a polymer-bioactive agent conjugate according to any one of the embodiments described herein comprises at least about 15 mol % bioactive agent.

Polymer-bioactive agent conjugates of the present invention may be incorporated into drug delivery systems, therapeutic devices, articles or preparations, and pharmaceutical products for the treatment of ocular hypertension.

In another aspect, the present invention provides a pharmaceutical product as an ocular implant or drug delivery system for the treatment of glaucoma comprising a polymer-bioactive agent conjugate of any one of the embodiments described herein. The implant may be in the form of a solid article, deformable solid, hydrogel, or liquid for placement in the eye of a subject.

In another aspect, there is provided a method for the treatment of glaucoma in a subject suffering glaucoma in one or both eyes, the method comprising administering an article comprising a polymer-bioactive agent conjugate of any one of the embodiments described herein to an eye afflicted with glaucoma. In one set of embodiments, the method comprises depositing the article in the lumen of a needle and injecting the article into the eye from the needle.

In another aspect, there is provided use of a polymer-bioactive agent conjugate of any one of the embodiments described herein the manufacture of a pharmaceutical product for the treatment of glaucoma. In one set of embodiments, the pharmaceutical product is in the form of an ocular implant. An ocular implant comprising the polymer-bioactive agent conjugate may be injectable.

DETAILED DESCRIPTION OF THE INVENTION

In one aspect, the present invention relates to a polymer-bioactive agent conjugate comprising a polymer backbone and a plurality of releasable bioactive agents covalently bonded to and pendant from the polymer backbone. In accordance with this aspect, the polymer backbone comprises a plurality of triazole moieties. The releasable bioactive agents are selected from the group consisting of prostaglandin analogues, β-blockers, and mixtures thereof. Bioactive agents used in the polymer conjugate of the invention may also be referred to herein as "drugs" or "prodrugs".

The term "drug" refers to a substance for therapeutic use whose application (or one or more applications) involves: a chemical interaction, or physico-chemical interaction, with a subject's physiological system; or an action on an infectious agent, or on a toxin or other poison in a subject's body, or with biological material such as cells in vitro.

As used herein, the term "prodrug" refers to a derivative of the drug moiety, wherein the derivative may have little or none of the activity of the drug moiety per se yet is capable of being converted in vivo or in vitro into a bioactive moiety. An example of such derivatisation is the acetylation of one or more hydroxyl groups on a bioactive moiety, such that subsequent to being released in vivo the released prodrug is deactylated to produce the drug moiety.

As used herein, the term "pharmaceutically acceptable salt" means those salts that are safe and effective for use in pharmaceutical preparations. Pharmaceutically acceptable salts include salts of acidic groups present in compounds of the invention. Suitable salts may include sodium, potassium, ammonium, calcium, diethylamine and piperazine salts and the like. Pharmaceutically acceptable salts are described in Stahl P H, Wermuth C G, editors. 2002. Handbook of pharmaceutical salts: Properties, selection and use. Weinheim/Zurich: Wiley-VCH/VHCA.

Polymers having bioactive agents covalently attached thereto are sometimes referred to in the art as "polymer—bioactive agent conjugates". In some instances, it may be convenient to refer to a polymer-bioactive agent conjugate of the invention as a "bioactive-polymer conjugate", "polymer-drug conjugate", "drug-polymer conjugate", "polymer conjugate", or simply a "conjugate".

Polymer-bioactive agent conjugates of the invention comprise a polymer backbone comprising a plurality of triazole moieties. Each triazole moiety is incorporated in the structure of the polymer chain, and forms part of the polymer backbone. Accordingly, the polymer backbone may be considered to be a polytriazole polymer.

The triazole moieties present in the polymer backbone are 1,2,3-triazole moieties. A skilled person will understand that such triazole moieties are products of an alkyne/azide reaction cycloaddition reaction performed under "click" chemistry conditions.

As used herein, the expression forming "part of the polymer backbone" means that the triazole moiety is part of the string of atoms that are each connected so as to form the polymer chain. In embodiments where the polymer backbone has a branched structure (i.e. has one or more branches or side chains extending from a main polymer chain), the triazole moiety may be part of a side chain as well as the main chain of the polymer. However, the expression is intended to exclude polymer structures where triazole moieties are present only in the side chain.

Polymer-bioactive agent conjugates of the invention, which have a plurality of triazole moieties in its polymer backbone, can be prepared through the use of click chemistry. The term 'click chemistry' was coined by Professor K. Barry Sharpless in 2001 to describe a series of chemical reactions defined by their modular nature, high yield, stability of products in vivo, stereospecificity, high atom economy and high thermodynamic driving force. A number of 'click' reactions exist, with several of them involving a cycloaddition reaction between appropriate functional groups to generate a stable cyclic structure.

Using click chemistry, at least two co-monomers of appropriate complementary terminal functionality can covalently react to form the polymer-bioactive agent conjugate of the invention. At least one of the co-monomers carries a pendant bioactive agent. During polymerisation of the co-monomers to form the conjugate, the complementary terminal functional groups in the co-monomers react with one another and form a triazole moiety as a product of the covalent coupling. This results in the co-monomers being linked together via the triazole moiety. Therefore, the resulting polymer-bioactive agent conjugate comprises triazole moieties as a part of its polymer backbone structure.

As used herein, the terms "polymer" and "polymer backbone" encompasses all parts of the conjugate, with the exception of the bioactive agent, which in formulae shown herein below can be represented by the moieties D, $D^1$ or $D^2$. Thus, the polymer backbone would encompass the linking group Z, shown in formulae herein described, unless otherwise indicated.

Polymer-bioactive agent conjugates prepared with click chemistry have a number of significant advantages over those prepared by other methods. One advantage of click reactions is that it can be used to provide a simpler method for preparing polymer-bioactive conjugates containing bioactive agents that have multiple reactive nucleophilic functionality. In the case of prostaglandin analogues and β-blockers, these bioactive agents contain multiple nucleophilic functional groups. For instance, prostaglandin analogues can contain hydroxy and carboxy functional groups, while β-blockers contain hydroxy and amino functional groups. It would be appreciated that such nucleophilic functional groups might otherwise need to be protected in order to avoid the possibility of undesirable intra-chain incorporation of the bioactive agent during polymer synthesis. As the click reaction is almost completely orthogonal in terms of its reactivity to the reactivity exhibited by functional groups such as hydroxyl groups, amino groups and other nucleophilic centres, protecting group strategies are not required as unprotected reactive functional groups (such as hydroxyl groups and amino groups) present in a bioactive agent would take no part in any click reaction.

A further advantage of click reactions is that it can allow polymer synthesis to proceed under relatively mild conditions, for example, at lower temperatures than that used in a number of conventional step-growth polymerisation techniques.

1,2,3-Triazole moieties can be produced through the reaction of co-monomers having appropriate complementary terminal functional groups comprising alkyne and/or azide functionalities, under click reaction conditions. The terms "complementary terminal functionality" and "complementary terminal functional group" as used in the context of the present invention means a terminal chemical group that is capable of reacting with another chemical group to form a covalent intermolecular bond there between.

An appropriate click reaction for the formation of 1,2,3-triazoles is the Huisgen 1,3-dipolar cycloaddition of azides and alkynes (thermal) which gives a mixture of the 1,4 and 1,5 regioisomers of the 1,2,3-triazole. Click reactions suitable for forming triazole moieties may also be metal catalysed. For example, a Copper(I)-catalyzed Azide-Alkyne Cycloaddition (CuAAC) variant of the Huisgen cycloaddition of azides and terminal alkynes forms 1,2,3-triazoles. Use of a copper catalyst in the Huisgen cycloaddition reaction results in formation of a 1,4-substituted 1,2,3-triazole from azides and terminal alkynes, while use of a ruthenium catalyst enables use of terminal or internal alkynes and results in the formation of the alternate 1,5-regiosiomer. The use of a silver catalyst also results in the 1,4-substituted 1,2,3-triazole. Other metals that can be used include, but are not limited to, Ni, Pt, Pd, Rh, and Ir; the regiochemistry of the 1,2,3 triazole resulting from the use of these metal catalysts is less well defined Some exemplary click functional groups have been described by W. H. Binder and R. Sachsenhofer in Macromol. Rapid Commun., 2007, 28, 15-54, the disclosure of which is incorporated herein by reference.

In addition to the thermal and metal catalysed variants of the Huisgen cycloaddition of azides and alkynes, a more recent development centres on the development of a metal-free, strain promoted azide-alkyne cycloaddition (SPAAC). In this variant, no catalyst is required as the alkyne is activated and made more reactive by incorporation of the alkyne functionality into a strained ring and/or by theselective placement of electron withdrawing functionality and heteroatoms in the vicinity of the alkyne grup. The regiochemistry of this SPAAC is mixed with both 1,4 and 1,5 1,2,3 triazoles being formed.

The use of appropriately functionalised co-monomers to prepare the polymer-bioactive agent conjugate can advantageously enable the composition, structure and molecular weight of the conjugate to be controlled. In contrast, polymers prepared by step growth polymerisation may have less reproducible molecular weights and a broader molecular weight distribution. Control over the structure and/or composition of the polymer-bioactive agent conjugate may be advantageous for regulatory purposes.

In some embodiments, the polymer-bioactive conjugate comprises a moiety of formula (I):

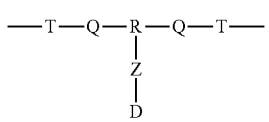
(I)

where:
T at each occurrence represents a triazole moiety;
Q is independently selected at each occurrence and may be present or absent and when present, represents a linking group;
R is an optionally substituted linear or branched hydrocarbon and may comprise optionally substituted aromatic hydrocarbon and or heteroaromatic hydrocarbon;
Z is a cleavable linking group; and
D is a releasable bioactive agent.

The polymer-bioactive agent conjugate typically comprises a plurality of moieties of formula (I), each group represented by Q, R, Z and D is independently selected and may be the same or different in each moiety.

In formula (I), the bioactive agent (represented by D) is selected from the group consisting of prostaglandin analogues and β-blockers. Examples of prostaglandin analogues and β-blockers are described herein.

Polymer-bioactive conjugates comprising a plurality of moieties of formula (I) may have moieties of formula (I) adjacent to each other or spaced apart within the polymer conjugate.

An important feature of the polymer-bioactive conjugates of the invention is that its polymer backbone comprises a plurality of triazole moieties. The triazole moieties in formula (I) are represented by the group T. Thus, the moiety of formula (I), which carries a pendant bioactive agent, is coupled to the remainder of the polymer backbone via triazole moieties.

In some embodiments, the polymer-bioactive agent conjugate comprises a polymer backbone comprising at least one triazole moiety selected from the group consisting of formula (II), (III) and (IX):

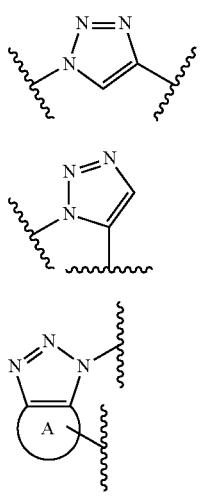

wherein in formula (IX), A represents an optionally substituted cyclic group, preferably said ring of from 7 to 9 constituent ring members.

In some embodiments, a polymer-bioactive agent conjugate comprising a triazole moiety of formula (II) may comprise a moiety selected from formula (IIa) and (IIb):

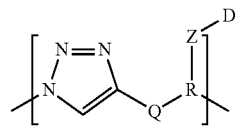
(IIa)

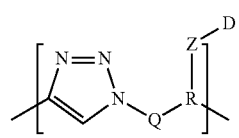
(IIb)

The moiety of formulae (II), (IIa) and (IIb) comprises a 1,4-substituted triazole moiety. Such a triazole moiety may be referred to herein as a 1,4-regioisomer.

In some embodiments, a polymer-bioactive agent conjugate comprising a triazole moiety of formula (III) may comprise a moiety selected from formula (IIIa) and (IIIb):

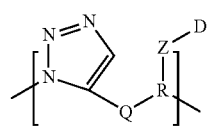
(IIIa)

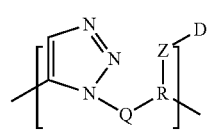
(IIIb)

The moiety of formulae (III), (IIIa) and (IIIb) comprises a 1,5-substituted triazole moiety. Such a triazole moiety may be referred to herein as a 1,5-regioisomer.

In some embodiments, a polymer-bioactive agent conjugate comprising a moiety of formula (IX) may comprise a moiety of formula (IXa) or (IXb):

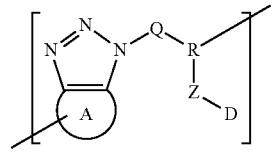
(IXa)

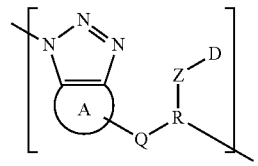
(IXb)

In formulae (IXa) and (IXb), A represents an optionally substituted cyclic group. Preferably the cyclic group comprises from 7 to 9 ring atoms. The ring atoms are each independently selected from the group consisting of C, N, O and S, preferably C, N and S. In one preference, A is C8 cycloalkyl. In one set of embodiments the ring "A" is said ring of from 7 to 9 constituent ring members described above.

In one set of embodiments of formulae (IXa) and (IXb), A is substituted with one or more substituents selected from the group consisting of hydroxy (—OH), —Oalkyl, alkyl, halo (preferably fluoro), cycloalkyl, heterocycloalkyl, aryl and heteroaryl. Cycloalkyl, heterocycloalkyl, aryl and heteroaryl substituent groups may comprise from 3 to 6 ring atoms and may be fused to A. The optional substitutents may be located on any ring atom of the cyclic group.

In the moieties of formula (IIa), (IIb), (IIIa), (IIIb), (IXa) and (IXb):

Q may be present or absent and when present represents a linking group;

R is an optionally substituted linear or branched hydrocarbon and may comprise optionally substituted aryl or heteroaryl Z is a cleavable linking group; and D is a releasable bioactive agent selected from the group consisting of prostaglandin analogues, β-blockers, and mixtures thereof.

A further discussion of the groups Q, R, Z and D is provided below.

The polymer-bioactive agent conjugates of the invention may comprise a plurality of triazole moieties of formula (II), (III) or (IX) as herein described. The triazole moieties may be independently selected at each occurrence.

The triazole moieties present in the polymer backbone may each of the same type, or they may be a mixture of different types. For example, the triazole moieties present in the polymer conjugates may each be the same and be selected from formulae (IIa), (IIb), (IIIa), (IIIb), (IXa) or (IXb). Alternatively, the polymer backbone of the polymer conjugate may comprise a mixture of these types of triazole moieties.

One skilled in the relevant art would understand that depending on the monomers employed in the synthesis of the polymer-bioactive conjugate and the reaction conditions, the resulting conjugate may comprise a single type of triazole moiety selected from those of formulae (IIa), (IIb), (IIIa), (IIIb), (IXa) or (IXb), or it may comprise a combination of such moieties.

In some embodiments, the conjugate may comprise a triazole moiety selected from those of formula (II) and (III), and preferably comprises at least one moiety selected from formulae (IIa), (IIb), (IIIa) and (IIIb). Thus the triazole moieties present in the polymer backbone of the conjugates may each be 1,4-substituted triazole moieties, 1,5-substituted triazole moieties, or a combination of these regioisomers.

In accordance with one embodiment of the polymer-bioactive agent conjugates of the invention, the triazole moieties may constitute at least 10 mol % of the polymer backbone. In some embodiments, the triazole moieties may constitute at least 20 mol % of the polymer backbone. In some embodiments, the triazole moieties may constitute at least 30 mol % of the polymer backbone.

As each triazole moiety is a reaction product from the covalent coupling of co-monomers, the proportion of triazole moieties in the polymer backbone may provide an indication of the degree of monomer incorporation in the polymer-bioactive agent conjugate.

The mol % of triazole moieties is determined on the basis of the proportion (on a molar basis) of such moieties within the polymer backbone in the conjugate.

As an example, the proportion of triazole moieties in polymer conjugates of the invention where a pendant bioactive moiety is coupled to the polymer backbone via a cleavable linking group (represented by Z in formulae described herein) may be determined by following equation:

$$\% \text{ triazole} = \left( \frac{67.05}{\left[ MW_{(monomer\text{-}bioactive\ agent\ conjugate)} + MW_{(co\text{-}monomer)} \right] - MW_{(bioactive\ agent\text{-}1)} + 17} \right) \times 100\%$$

The polymer backbone of the conjugates of the present invention have a molecular weight of about 250 Daltons to about 10 MM Daltons, preferably from 500 Daltons to 2M Daltons.

The conjugates of the invention comprise a plurality of releasable bioactive agents covalently bonded to and pendant from the polymer backbone.

In some embodiments, conjugates of the invention comprise at least about 5 mol %, at least 10 mol %, at least 15 mol %, at least 20 mol %, or at least 30 mol % bioactive agent. The mol % of bioactive agent may be determined relative to the total number of moles of monomer that form the polymer conjugate.

The conjugates of the present invention can accommodate high bioactive agent loadings, minimising the amount of material required to deliver a dose of bioactive agent. Bioactive agent loadings of at least 5% by weight, at least 10% by weight, at least 15% by weight, at least 20% by weight, or at least 30% by weight, relative to the total weight of the polymer conjugate may be achieved.

In some embodiments, conjugates of the invention comprise up to 60 mol %, up to 70 mol %, up to 80 mol %, up to 90 mol % and even up to 100 mol % of conjugated bioactive agent, relative to the total number of moles of monomer that form the polymer conjugate. Those skilled in the art would appreciate that the mol % of bioactive agent may be dependent on the relative molar ratio of monomers used to form the polymer conjugate.

In some embodiments, polymer-bioactive agent conjugates of the invention comprise a moiety of formula (Ib):

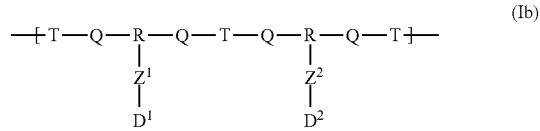

where:

T at each occurrence represents a triazole moiety;

Q is independently selected at each occurrence may be present or absent and when present represents a linking group;

R is an optionally substituted linear or branched hydrocarbon and may comprise optionally substituted aromatic hydrocarbon or heteroaromatic hydrocarbon;

$Z^1$ and $Z^2$ are each cleavable linking groups that may be the same or different; and $D^1$ and $D^2$ are each bioactive agents that may be the same or different.

A moiety of formula (Ib) may occur when two moieties of formula (I) are covalently coupled together in the polymer conjugate.

In the moiety of formula (Ib), each T may be independently selected from a triazole moiety of formula (II), (III)

or (IX). For instance, each T may be independently selected from triazole moiety of formula (IIa), (IIb), (IIIa), (IIIb), (IXa) and (IXb).

In one set of embodiments, in the moiety of formula (Ib), each T may be a 1,4-substituted triazole moiety or a 1,5-substituted triazole moiety. Alternatively, formula (Ib) may comprise a combination of such 1,4 and 1,5-regioisomers.

In the moiety of formula (Ib), each Q and R may be independently selected from any one of the moieties described herein for such groups.

The groups $Z^1$ and $Z^2$ in the moiety formula (Ib) are each cleavable linking groups, which may be the same or different at each occurrence. $Z^1$ and $Z^2$ may each be independently selected from any one of the groups described herein for the group Z. Where $Z^1$ and $Z^2$ are different, there exists the possibility that release of the bioactive agent can be further controlled.

The bioactive agents $D^1$ and $D^2$ are coupled to $Z^1$ and $Z^2$ respectively via a cleavable covalent bond. Examples of cleavable covalent bonds are described herein with reference to the linking group Z.

The groups $D^1$ and $D^2$ in the moiety of formula (Ib) are each bioactive agents, which may be the same or different at each occurrence. $D^1$ and $D^2$ may each be independently selected from any one of the bioactive agents as described herein for the group D. In accordance with the invention, $D^1$ and $D^2$ may each be independently selected from the group consisting of prostaglandin analogues and β-blockers.

In some embodiments, it may be desireable for $D^1$ and $D^2$ to be same. In such embodiments, the bioactive agents are therefore of a single type of drug (i.e. prostaglandin analogues or β-blockers only).

In some embodiments, it may be desireable for $D^1$ and $D^2$ to belong to the same class of drug, but be different bioactive agents within the same drug class. In such embodiments, the $D^1$ and $D^2$ may each be either prostaglandin analogues or β-blocker but be selected from different drugs within the class (e.g. a mixture of timolol and betaxolol of β-blocker drug class).

In some embodiments, it may be desirable for $D^1$ and $D^2$ to be different (i.e. a mixture of prostaglandin analogues and β-blockers). This may enable different therapeutic agents to be delivered to a subject by a single polymer conjugate. Without wishing to be limited by theory, it is believed that the use of a mixture of bioactive agents may advantageously provide an enhanced therapeutic effect (e.g. an additive or synergistic effect) in lowering intraocular pressure. Combination eye drops comprising a prostaglandin analogue in combination with a β-blocker have been shown to provide a greater reduction of ocular hypertension than either of the single agent eye drops (Higginbotham et al., *Arch Ophthalmol* 2002: 120, 915-922; Pfieffer et al. IOVS 2000: 41(4), s754; Sjoquist et al. IOVS 2000: 41(4), s572; Larsson et al. IOVS 2000: 41(4), s280; Martinez & Sanchez Eye 2009: 23, 810-818; PCT/SE2001/002499). Thus a mixture of different bioactive agents in the polymer conjugate may be more efficacious than a single type of bioactive agent alone.

A polymer-bioactive agent conjugate comprising a moiety of formula (Ib) may have a higher loading of bioactive agent. For example, a polymer-bioactive agent conjugate comprising formula (Ib) may comprise more than 50 mol % of bioactive agent. In some embodiments, the polymer-bioactive agent conjugate may comprise up to 60 mol %, up to 70 mol %, up to 80 mol % up to 90 mol % and even up to 100 mol % of conjugated bioactive agent, relative to the total number of moles of monomer that form the polymer conjugate.

The "bioactive agent" (also represented as "D" in certain formulae herein) employed in the polymer-bioactive agent conjugate of the invention is selected from the group consisting of prostaglandin analogues, β-blockers, and mixtures thereof. Prostaglandin analogues and β-blockers are each intraocular pressure lowering drugs.

Ophthalmic pharmaceuticals such as prostaglandin analogues and β-blockers are used to treat glaucoma and ocular hypertension. These drugs are used as therapeutic agents to treat or alleviate increased ocular pressure associated with eye disorders such as glaucoma by acting to reduce intraocular pressure. As discussed above, prostaglandin analogues exert an ocular hypotensive effect by increasing uveoscleral outflow of aqueous humour while β-blockers lower intraocular pressure by reducing the production of aqueous humour in the eye.

Prostaglandin analogues and β-blockers bound to the polymer backbone of the conjugate of the invention are in pendant form. By being "pendant", the bioactive agents do not form part of the polymer backbone structure and as such, can be released without causing a reduction in the chain length of the polymer backbone. The pendant configuration can also ensure efficient release of the drug.

A skilled person would appreciate that bioactive agents such as prostaglandin analogues and β-blockers possess functional groups. Functional groups in a bioactive agent may be used to promote covalent coupling of the agent to the polymer backbone.

In the case of prostaglandin analogues and β-blockers, these bioactive agents comprise carboxylic acid, hydroxy and amino (primary amino) functional groups. More specifically, prostaglandin analogues comprise carboxylic acid and hydroxy functional groups, while β-blockers comprise hydroxy and amino functional groups.

As discussed above, when a bioactive agent contains more than one such functional group, there is a potential for these functional groups to react with terminal functional groups in many monomers used in step growth polymerisation. For example, polyurethane conjugates may be formed with a diisocyanate monomer and a diol monomer. The isocyanate and hydroxyl groups in the co-monomers react to form a urethane linked polymer. The diol monomer may include a conjugated bioactive agent. In such instances, if the conjugated bioactive agent also comprises a free hydroxyl functional group, the free hydroxyl group on the bioactive agent may compete with the diol hydroxyl groups for reaction with an isocyanate group of the diisocyanate monomer. If this occurs, the bioactive agent may become incorporated in the polymer backbone of the conjugate, rather than being pendant.

As polymer-bioactive agent conjugates of the invention are prepared using click chemistry, it is an advantage of the invention that bioactive agents having multiple functional groups can be covalently coupled to the polymer backbone without the need to employ protecting group strategies, which might otherwise be used to protect certain functional groups from reaction to thereby ensure that a bioactive agent is covalently coupled to the polymer backbone in a preselected fashion.

In one aspect, a polymer-bioactive agent conjugate according to the invention comprises a releasable bioactive agent selected from prostaglandin analogues.

A "prostaglandin" is an endogenous substance typically derived from C20 prostanoic acid illustrated below:

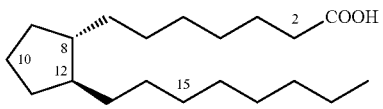 [SMILES: CCCCCCCC[C@H]1CCC[C@@H]1CCCCCCC(=O)O]

As used herein, the term "prostaglandin analogue" refers to a molecule that is designed to bind to a prostaglandin receptor. Prostaglandin analogues may be modified derivatives of endogenous prostaglandins or synthetic anologues of endogenous prostaglandins. Prostaglandin analogues can be in the form of a therapeutically active drug or a prodrug. Many prostaglandin analogues are prodrugs (for example, an ester derivative of a prostaglandin). However, such prostaglandin prodrugs are often referred to as prostaglandin analogues as they act on the prostaglandin F receptor, after the ester group is hydrolyzed to form a 1-carboxylic acid (free acid form of the drug).

The prostaglandin analogue, or a pharmaceutically acceptable salt thereof, is conjugated to the polymer backbone. The present invention enables the prostaglandin analogue, or pharmaceutically acceptable salt thereof to be delivered to a desired site in order to produce a therapeutic effect.

In one embodiment, the bioactive agent is an analogue of a prostaglandin belonging to the PGF2α class of prostaglandin. PGF2α prostaglandin analogues are designed to bind to the prostaglandin F2α receptor.

Prostaglandin analogues as described herein constitute an α-chain, an ω-chain and a 5-membered ring, numbered according to the C20 prostanoic acid as follows:

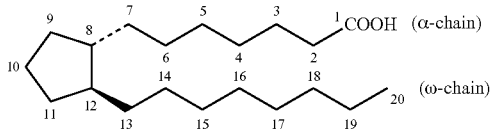

In one aspect, the present invention relates to a polymer-drug conjugate comprising a polymer backbone and a PGF2α class of prostaglandin analogue conjugated to the polymer backbone.

Prostaglandins analogues delivered by polymer-bioactive agent conjugates of the invention comprise at least one functional group selected from the group consisting of a carboxylic acid group at the 1 position, a hydroxy group at the 9 position, a hydroxy group at the 11 position, and a hydroxy group at the 15 position.

The carboxylic acid group at the 1 position, and the hydroxy groups at the 9, 11 and 15 position of the prostaglandin analogue can serve as reactive functional groups for conjugation of the prostaglandin drug to a polymer. In conjugating the drug to the polymer backbone, the prostaglandin analogue is conjugated to the polymer backbone via a selected group at the 1, 9, 11 or 15 position. The drug moiety (denoted D in formulae described herein) linked to the polymer is therefore an acid residue (in the case of conjugation at the 1 position) or an alcohol residue (in the case of conjugation at the 9, 11 or 15 positions) of the ester, anhydride or carbonate linking group conjugating the prostaglandin analogue to the polymer backbone. The moiety represented by D may therefore be a releasable prostaglandin analogue.

The prostaglandin analogue may be conjugated to the polymer backbone via an ester, anhydride or carbonate linking group. Ester, anhydride and carbonate linking groups have been found to be hydrolytically labile in biological environments and can help to ensure that a sufficient amount of the drug is effectively released from the polymer conjugate to achieve therapeutic levels in the immediate vicinity of the polymer conjugate material.

When the prostaglandin analogue is conjugated to the polymer backbone by an ester linking group, the ester linking group may link the drug at a position selected from the group consisting of the 1, 9, 11 and 15 position of the drug.

When the prostaglandin analogue is conjugated to the polymer backbone by a carbonate linking group, the carbonate linking group may link the drug at a position selected from the group consisting of the 9, 11 and 15 position of the drug.

When the prostaglandin analogue is conjugated to the polymer backbone by an anhydride linking group, the anhydride linking group may link the drug at the 1 position of the drug.

As used herein, the term "acid residue" is a reference to that part of an ester or anhydride linking group that is derived from a carboxylic acid functional group of a bioactive agent, after conjugation of the bioactive agent to the polymer backbone. The acid residue will generally have the structure —C(O)O—. In the case of a prostaglandin analogue, the carboxylic acid group is located at the 1 position.

As used herein the term "alcohol residue" is a reference to that part of an ester or carbonate linking group that is derived from a hydroxy functional group of a bioactive agent, after conjugation of the bioactive agent to the polymer backbone. The alcohol residue will generally have the structure —O—. In the case of a prostaglandin analogue, the hydroxy group may be selected by located at the 9, 11 or 15 position. In the case of a β-blocker, the hydroxy group is part of the beta-amino alcohol group of the drug molecule.

In one set of embodiments, the bioactive agent (D) is a prostaglandin analogue of formula (X):

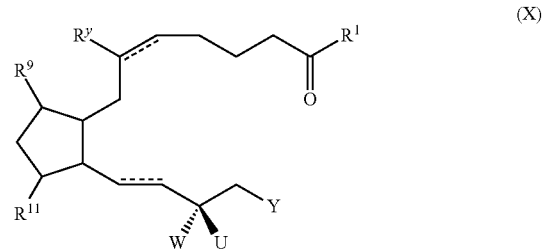

where:
▭▭▭▭ represents a double or single bond;
W and U are selected from the group consisting of where W and U together form oxo (═O), where W and U are each halo, and where W is R$^{15}$ and U is hydrogen;
R$^y$ is an optional substituent selected from the group consisting of oxo and hydroxy;
Y is optionally substituted C4 to C10 hydrocarbyl or optionally substituted $C_4$ to $C_{10}$ hydrocarbyloxy; and
one of R$^1$, R$^9$, R$^{11}$ and R$^{15}$ is linked to the polymer backbone and wherein:
R$^9$, R$^{11}$ and R$^{15}$ when linked to the polymer backbone are the alcohol residue of an ester or carbonate linking group and $R^1$ when linked to the polymer backbone forms the acid residue of an ester or anhydride linking group; and $R^1$ when not linked to the backbone is selected from the group consisting of —OH, —O($C_{1-6}$ alkyl), and —$NR^aR^b$ where $R^a$ and $R^b$ are each independently selected from the group consisting of H and $C_{1-6}$ alkyl;

$R^9$ and $R^{11}$ when not linked to the polymer backbone are both hydroxy and where one of $R^9$ and $R^{11}$ is linked to the backbone, the other is hydroxy; and when $R^{15}$ is not linked to the backbone then W is hydroxy and U is hydrogen, or W and U are each fluoro, or W and U together form oxo.

In some embodiments, the prostaglandin analogue of formula (X) is selected from the group consisting of:

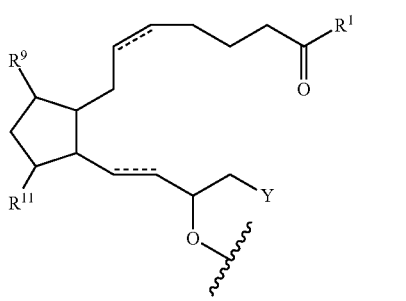

(Xa)

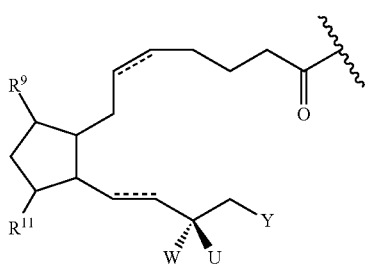

(Xb)

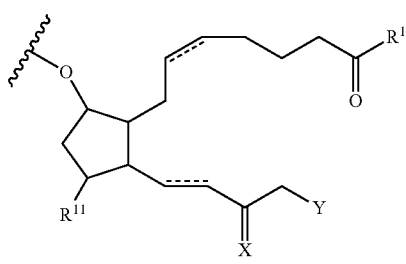

(Xc)

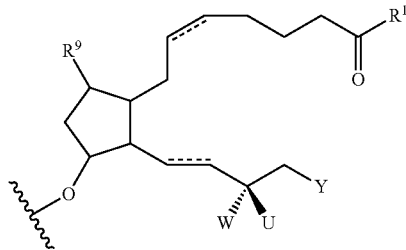

(Xd)

wherein:

〰〰 represents the point of attachment of the prostaglandin analogue to Z;

------ represents a double or single bond;

Y is optionally substituted C4 to C10 hydrocarbyl or optionally substituted C4 to C10 hydrocarbyloxy;

in formulae (Xa), (Xc) and (Xd) $R^1$ is hydroxy, $C_1$ to $C_6$ alkoxy or $C_1$ to $C_6$ alkylamino (preferably, isopropoxy or ethylamino);

in formulae (Xa) and (Xb) $R^9$ and $R^{11}$ are hydroxy;

in formula (Xc) $R^{11}$ is hydroxy and X is O or hydroxy;

in formula (Xd) $R^9$ is hydroxy; and in formulae (Xb) and (Xd) W is hydroxy and U is hydrogen, or W and U are both fluoro, or W and U together form oxo.

In prostaglandin analogues of formula (X), Y is optionally substituted $C_4$ to $C_{10}$ hydrocarbyl or optionally substituted $C_4$ to $C_{10}$ hydrocarbyloxy. The hydrocarbyl (including the hydrocarbyl portion of the hydrocarbyloxy) may comprise aliphatic, alicyclic or aromatic hydrocarbon groups or combinations thereof.

In some embodiments of formula (X), Y is optionally substituted with one or more substituents selected from halo and halo-$C_1$ to $C_4$ alkyl. Suitable halo may be fluoro, chloro, bromo or iodo. Preferred halo is fluoro. Halo-$C_1$ to $C_4$ alkyl may be perhalomethyl, such as for example, trifluoromethyl.

In some embodiments, Y is selected from the group consisting of $C_4$ to $C_{10}$ alkyl, $C_4$ to $C_{10}$ alkoxy, phenyl, phenyl substituted $C_1$ to $C_4$ alkyl, and phenyl substituted $C_1$ to $C_4$ alkoxy, wherein the groups are optionally substituted with one or more groups selected from halo and perhalomethyl. In some specific embodiments, Y is selected from the group consisting of —$(CH_2)_3CH_3$, —$OC_6H_4$(meta-$CF_3$), —$(CH_2)_5CH_3$, —$O(C_6H_5)$ and —$CH_2(C_6H_5)$.

In formula (X), W and U represent substituent groups present on the prostaglandin analogue. In some embodiments, W and U together form an oxo (=O) substituent group. In other embodiments, W and U are each halo substituent groups. Suitable halo may be fluoro, chloro, bromo or iodo. Preferred halo is fluoro. In other embodiments, W is $R^{15}$ and U is hydrogen.

In accordance with the invention, the prostaglandin analogue is linked to the polymer backbone by one of $R^1$, $R^9$, $R^{11}$ and $R^{15}$. Accordingly, when linked to the polymer backbone, $R^9$, $R^{11}$ and $R^{15}$ represent the alcohol residue (—O—) of an ester or carbonate linking group, and $R^1$ forms the acid residue (—C(O)O—) of an ester or anhydride linking group. In formulae described herein, the ester, carbonate or anhydride linking group is formed when the prostaglandin analogue (represented by D) is conjugated with the linking group Z. That is, the prostaglandin analogue of formula (X), together with Z, forms an ester, carbonate or anhydride linking group. Some specific examples of Z are described below.

In some embodiments, $R^1$ is linked to the polymer backbone via an ester linkage or an anhydride linkage. In such embodiments, $R^9$, $R^{11}$ and $R^{15}$ are not linked to the polymer backbone.

In some embodiments, $R^9$ is linked to the polymer backbone via an ester linkage or a carbonate linkage. In such embodiments, $R^1$, $R^{11}$ and $R^{15}$ are not linked to the polymer backbone.

In some embodiments, $R^{11}$ is linked to the polymer backbone via an ester linkage or a carbonate linkage. In such embodiments, $R^1$, $R^9$ and $R^{15}$ are not linked to the polymer backbone.

In some embodiments, $R^{15}$ is linked to the polymer backbone via an ester linkage or a carbonate linkage. In such embodiments, $R^1$, $R^9$ and $R^{11}$ are not linked to the polymer backbone.

One skilled in the art would understand that when $R^1$, $R^9$, $R^{11}$ and $R^{15}$ are not linked to the polymer backbone, then these groups may represent substituent groups.

$R^1$ when not linked to the polymer backbone may together with the carbonyl group (—O(O)—), be a carboxylic acid group, or an ester or amide derivative thereof. In some embodiments, $R^1$ when not linked to the polymer backbone is selected from the group consisting of —OH, —O($C_{1-6}$ alkyl), and —$NR^aR^b$ where $R^a$ and $R^b$ are each independently selected from the group consisting of H and $C_{1-6}$ alkyl. In specific embodiments, $R^1$ when not linked to the polymer backbone is selected from the group consisting of —OH, —O(iso-propyl) and —NHethyl.

$R^9$ and $R^{11}$ when not linked to the polymer backbone are each hydroxy groups.

When $R^{15}$ is not linked to the polymer backbone then W and U may each represent hydrogen or a substituent group, or W and U together may form a substituent group. In some embodiments, W is hydroxy and U is hydrogen. In other embodiments, W and U are each halo (preferably fluoro). In yet other embodiments, W and U together form oxo.

In one set of embodiments, the bioactive agent is a prostaglandin analogue of formula (Xe):

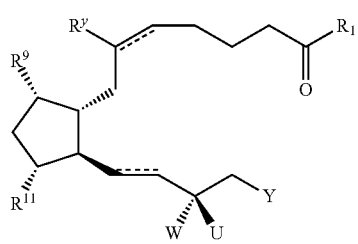

(Xe)

where:

═════ represents a double or single bond;

W and U are selected from the group consisting of where W and U together form oxo (═O), where W and U are each halo, and where W is $R^{15}$ and U is hydrogen;

$R^y$ is an optional substituent selected from the group consisting of oxo and hydroxy;

Y is optionally substituted $C_4$ to $C_{10}$ hydrocarbyl or optionally substituted $C_4$ to $C_{10}$ hydrocarbyloxy; and one of $R^1$, $R^9$, $R^{11}$ and $R^{15}$ is linked to the polymer backbone and wherein:

$R^9$, $R^{11}$ and $R^{15}$ when linked to the polymer backbone are the alcohol residue of an ester or carbonate linking group and $R^1$ when linked to the polymer backbone forms the acid residue of an ester or anhydride linking group; and $R^1$ when not linked to the backbone is selected from the group consisting of —OH, —O($C_{1-6}$ alkyl), and —$NR^aR^b$ where $R^a$ and $R^b$ are each independently selected from the group consisting of H and $C_{1-6}$ alkyl;

$R^9$ and $R^{11}$ when not linked to the polymer backbone are both hydroxy and where one of $R^9$ and $R^{11}$ is linked to the backbone, the other is hydroxy; and when $R^{15}$ is not linked to the backbone then W is hydroxy and U is hydrogen, or W and U are each fluoro, or W and U together form oxo.

In some embodiments, the prostaglandin analogue is selected from the group consisting of:

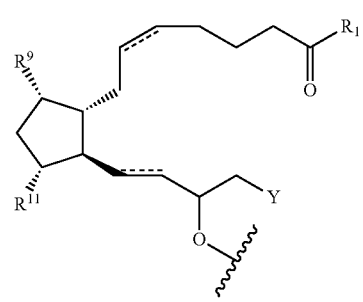

(Xf)

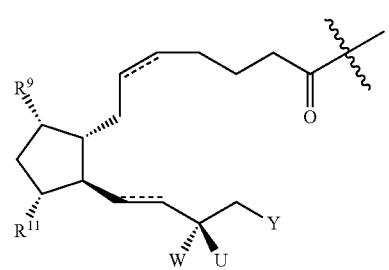

(Xg)

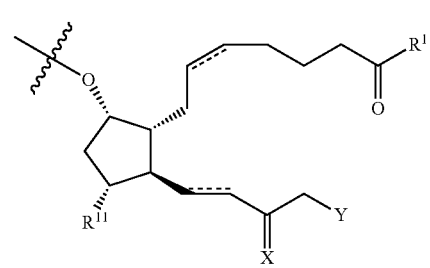

(Xh)

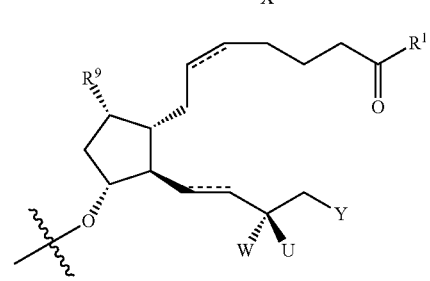

(Xi)

wherein:

∿∿∿ represents the point of attachment of the prostaglandin analogue to linking group Z;

═════ represents a double or single bond;

Y is optionally substituted C4 to C10 hydrocarbyl or optionally substituted $C_4$ to $C_{10}$ hydrocarbyloxy;

in formulae (Xf), (Xh) and (Xi) $R^1$ is hydroxy, $C_1$ to $C_6$ alkoxy or $C_1$ to $C_6$ alkylamino (preferably, isopropoxy or ethylamino);

in formulae (Xf) and (Xg) $R^9$ and $R^{11}$ are hydroxy;

in formula (Xh) $R^{11}$ is hydroxyl and X is O or hydroxy;

in formula (Xi) $R^9$ is hydroxy; and in formulae (Xg), (Xh) and (Xi) W is hydroxy and U is hydrogen, or W and U are both fluoro, or W and U together form oxo.

A skilled person would be able to ascertain the chemical structure of a variety of prostaglandin analogues. Prostaglandin analogues conjugated to polymer-drug conjugates of the invention may be in free acid form (including pharmaceutically acceptable salts thereof) or prodrug form.

By "free acid" form is meant that prostaglandin analogues as described herein may present as a "free" carboxylic acid (i.e. COOH) or be conjugated to the polymer backbone through that free carboxylic acid group at the 1 position of the prostaglandin analogue. The free carboxylic acid group is generally in the α-chain of the prostaglandin analogue. In such cases, the prostaglandin analogue is releasable, or can be released, in its free acid form. The free acid form may optionally be associated with a pharmaceutically acceptable salt.

Prostaglandin analogues in free acid form may also be conjugated through a hydroxy group at the 9, 11 or 15 position of the prostaglandin molecule. In such embodiments, the prostaglandin analogue is also releasable, or can be released, in its free acid form. The free acid form may optionally be associated with a pharmaceutically acceptable salt.

When the prostaglandin analogue is present as the prodrug, the prostaglandin analogue will generally be conjugated through a hydroxy group at the 9, 11 or 15 position. In such cases, the prostaglandin analogue is releasable, or can be released, in its prodrug form.

Prostaglandin analogues as described herein may present as a prodrug, wherein the carboxylic acid at the 1 position is substituted with a labile substituent group that is removable in vivo. In such cases, the prostaglandin analogue will be conjugated to the polymer backbone through a hydroxy group at the 9, 11 or 15 position. In such cases, the prostaglandin analogue is releasable, or can be released, in its prodrug form. A prodrug may be an ester or amide derivative of the free acid form of the bioactive agent. The prodrug can be converted into the free acid form in vivo. For example, latanoprost, travoprost, tafluprost and bimatoprost are prodrugs, and are converted to their free acid forms in vivo.

In the context of the present invention it may be convenient to refer to the prostaglandin analogues of general formula (X) as the free acid form of other prostaglandins. For example the free acid form of latanoprost is ((Z)-7-[(1R, 2R,3R,5S)-3,5-dihydroxy-2-[(3R)3-hydroxy-5-phenylpentyl]-cyclopentyl]hept-5-enoic acid.

Some examples of prostaglandin analogues that may be delivered by the polymer-bioactive agent conjugates are latanoprost, travoprost, bimatoprost and tafluprost, the free acid form of latanoprost, travoprost (known as fluprostenol), bimatoprost and tafluprost, as well as carboprost, unoprostone and dinoprost. These prostaglandin analogues are shown in Table 1. Such drugs (either in prodrug or free acid form) are conjugated to the polymer backbone of the polymer conjugates of the invention by one of the functional groups located at the 1, 9, 11 or 15 positions of the prostaglandin analogue, and may be delivered or released in free acid or prodrug form. Preferably, the prostaglandin analogue is selected from latanoprost and the free acid form of latanoprost.

TABLE 1

| Pro-drug form | Free-acid form |
|---|---|
| | 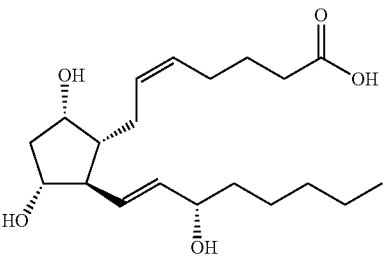 [SMILES: CCCCC[C@H](O)/C=C/[C@@H]1[C@@H](C/C=C\CCCC(=O)O)[C@@H](O)C[C@H]1O]<br>PGF2α (dinoprost) |
| | 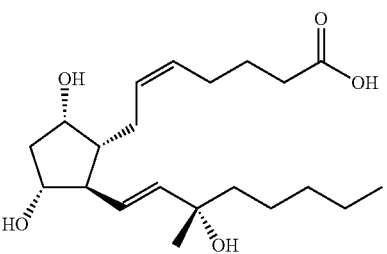 [SMILES: CCCCC[C@](C)(O)/C=C/[C@@H]1[C@@H](C/C=C\CCCC(=O)O)[C@@H](O)C[C@H]1O]<br>Carboprost |
| | 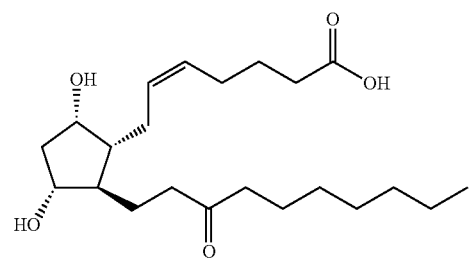 [SMILES: CCCCCCCC(=O)CC[C@@H]1[C@@H](C/C=C\CCCC(=O)O)[C@@H](O)C[C@H]1O]<br>Unoprostone |

TABLE 1-continued

| Pro-drug form | Free-acid form |
|---|---|
| Latanoprost | Free acid form of Latanoprost |
| Bimatoprost | Free acid form of Bimatoprost |
| Travoprost | Fluprostenol (free acid form of travoprost) |
| Tafluprost | Free acid form of tafluprost |

In some embodiments of the present invention, D as shown in formulae described herein is selected from the following group:

| Drug | 1-COOH | 9-OH |
|---|---|---|
| PGF$_{2\alpha}$ | | |
| Carboprost | | |
| Latanoprost | | |
| Bimatoprost | | |
| Travoprost | | |

-continued
| Drug | 11-OH | 15-OH |
|---|---|---|
| Tafluprost | 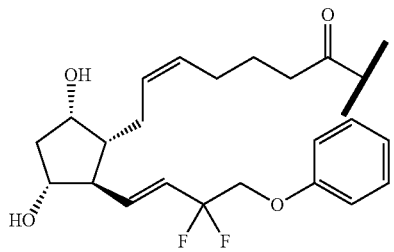 | 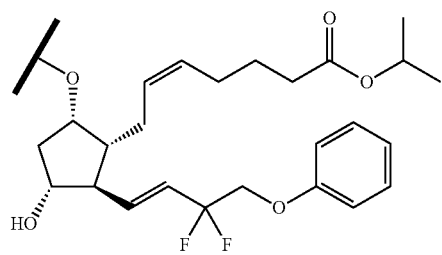 |
| Unoprostone | 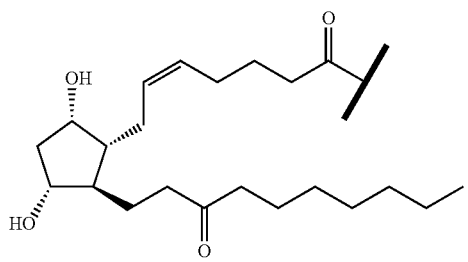 | 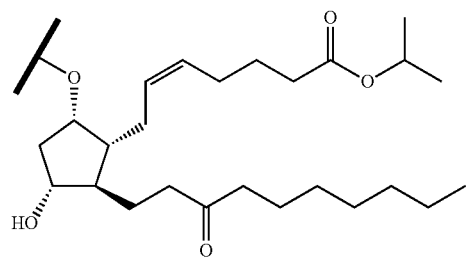 |
| PGF$_{2\alpha}$ | 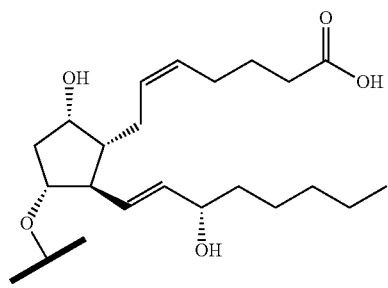 | 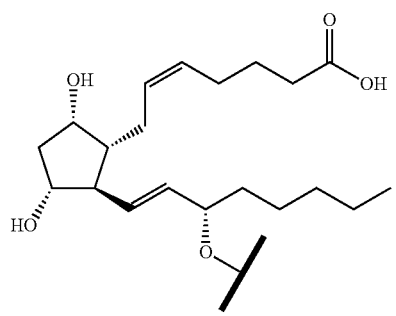 |
| Carboprost | 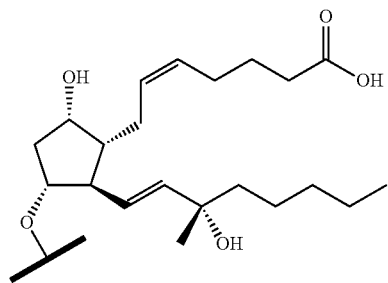 | 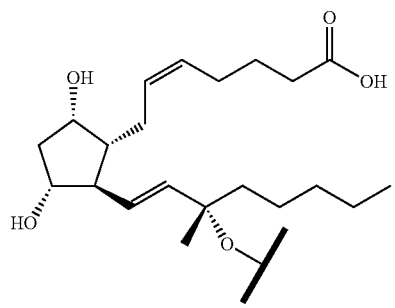 |
| Latanoprost | 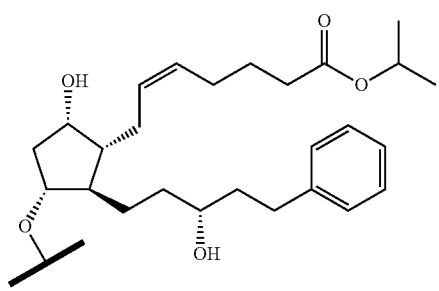 | 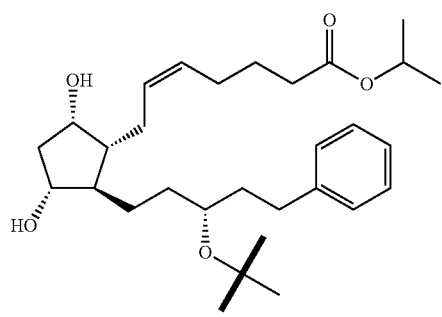 |

-continued

Bimatoprost

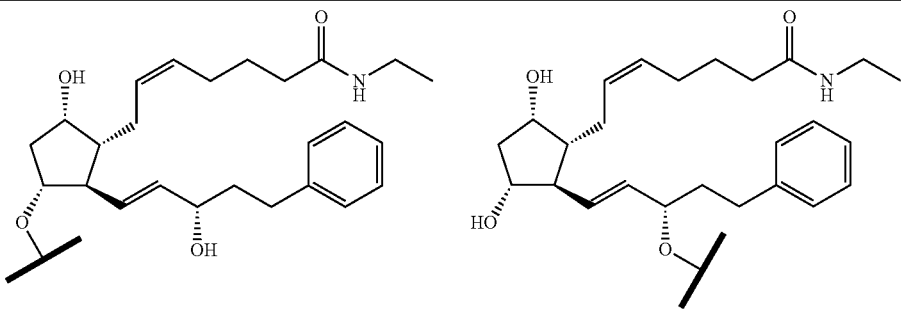

Travoprost

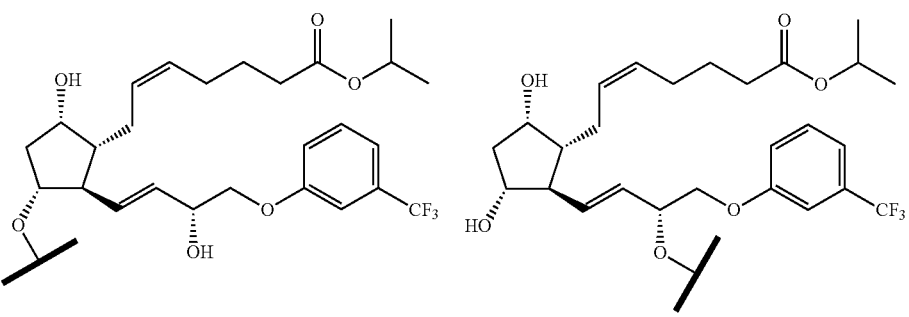

Tafluprost

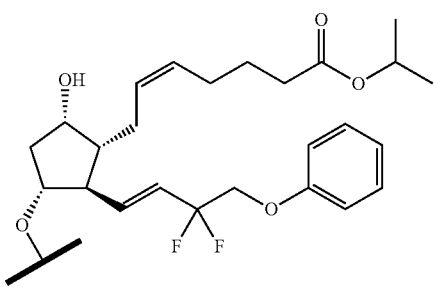

Unoprostone

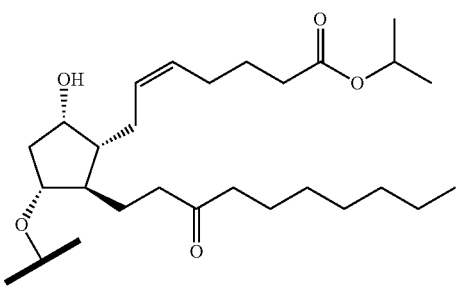

In another aspect, a polymer-bioactive agent conjugate according to the invention comprises a bioactive agent selected from β-blockers. A β-blocker is a drug that has pharmacological activity to block or antagonise β-adrenergic receptors. The β-blockers employed in the polymer conjugates of the invention are preferably beta-amino alcohol β-adrenergic antagonists.

Beta-amino alcohol β-adrenergic antagonists comprise an alcohol (—OH) and an amino (—NH$_2$, —NHR or —NR$_2$) functional group. The β-blocker is conjugated to the polymer backbone via an ester or carbonate linking group formed with the alcohol moiety of the β-amino alcohol group.

In one set of embodiments the bioactive agent (D) is a β-blocker of formula (XX);

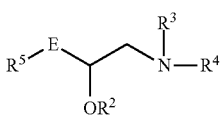

(XX)

wherein:
E is a bond or —OCH$_2$— (preferably —OCH$_2$—);
R$^2$ is linked to the polymer backbone and is the alcohol residue of an ester or carbonate linking group;
R$^2$ and R$^4$ are each independenly selected from the group consisting of H, and linear or branched C$_1$-C$_4$ alkyl optionally substituted by one or more substituents selected from the group consisting of hydroxy, optionally substituted alkoxy, optionally substituted aryloxy, optionally substituted amido, optionally substituted cycloalkyl, and optionally substituted aryl; (preferably R³ is H and R⁴ is isopropyl or tert-butyl); and R⁵ is an optionally substituted cycloalkyl or aryl moiety (including polycyclic moieties).

In one embodiment the group R⁵ may be a group of formula

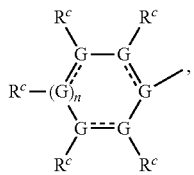

providing a bioactive agent (D) which is a β-blocker of formula (XXa):

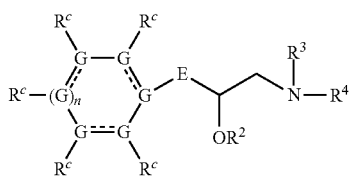

wherein:

R² is linked to the polymer backbone and is the alcohol residue of an ester or carbonate linking group;

------ represents a single bond or double bond;

E is a bond or —OCH₂—;

G at each occurrence is independently selected from the group consisting of carbon (C), nitrogen (N), oxygen (O) and sulphur (S), with the proviso that at least two G are carbon;

R³ and R⁴ are each independently selected from the group consisting of H, and linear or branched $C_1$-$C_4$ alkyl optionally substituted by one or more substituents selected from the group consisting of hydroxy, optionally substituted alkoxy, optionally substituted aryloxy, optionally substituted amido, optionally substituted cycloalkyl, and optionally substituted aryl (preferably R³ is H and R⁴ is isopropyl or tert-butyl);

$R^c$ at each occurrence is an optional substituent, or two $R^c$ can join together to form an optionally substituted cycloalkyl or aryl ring; and n is 0 or 1.

In one set of embodiments of formula (XX), R⁵ may be selected from the group consisting of 4-morpholin-4-yl-1,2,5-thiadiazol-3-yl, [2-(cyclopropylmethoxy)ethyl]-phenyl, 3,4-dihydronaphthalen-1(2H)-one, 4-phenyl-acetamide, 1-napthyl, and 4-(2-methoxyethyl)phenyl.

In some embodiments, the bioactive agent (D) is β-blocker of formula (XXb):

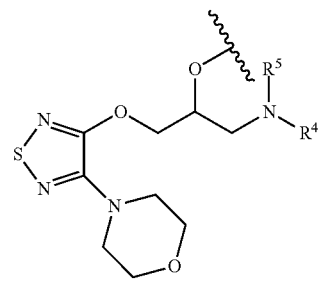

wherein:

------ represents the point of attachment of the β-blocker to Z;

R³ and R⁴ are each independently selected from the group consisting of H, and linear or branched $C_1$-$C_4$ alkyl optionally substituted by one or more substituents selected from the group consisting of hydroxy, optionally substituted alkoxy, optionally substituted aryloxy, optionally substituted amido, optionally substituted cycloalkyl, and optionally substituted aryl (preferably R³ is H and R⁴ is isopropyl or tert-butyl).

In some embodiments, the β-blocker is of formula (XXc):

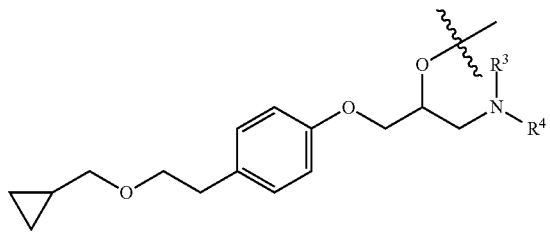

wherein:

------ represents the point of attachment of the β-blocker to the ester or carbonate linking group conjugating the drug to the polymer backbone;

R³ and R⁴ are each independently selected from the group consisting of H, and linear or branched $C_1$-$C_4$ alkyl optionally substituted by one or more substituents selected from the group consisting of hydroxy, optionally substituted alkoxy, optionally substituted aryloxy, optionally substituted amido, optionally substituted cycloalkyl, and optionally substituted aryl (preferably R³ is H and R⁴ is isopropyl or tert-butyl).

Some specific examples of releasable β-blockers of formulae described herein are betaxolol, carteolol, levobunolol, metripranolol, and timolol, preferably timolol. These β-blockers are shown in Table 2. The β-blockers are conjugated to the polymer backbone of the polymer-bioactive agent conjugate via the alcohol moiety of the beta-amino alcohol group of the drug.

TABLE 2

| Drug | Structure |
|---|---|
| betaxolol | 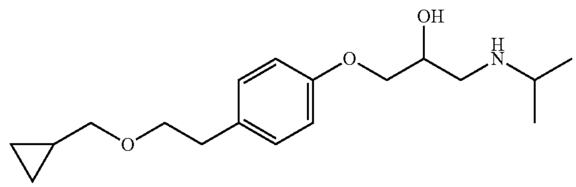 [SMILES: CC(C)NCC(O)COc1ccc(CCOCC2CC2)cc1] |
| carteolol | 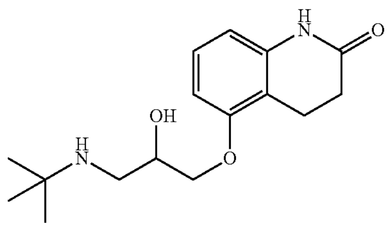 [SMILES: CC(C)(C)NCC(O)COc1cccc2c1CCC(=O)N2] |
| levobunolol | 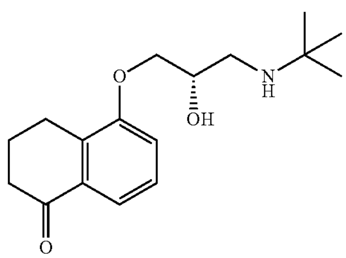 [SMILES: CC(C)(C)NC[C@H](O)COc1cccc2c1CCCC2=O] |
| metripranolol | 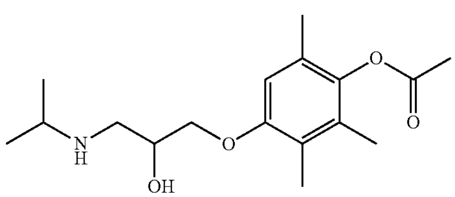 [SMILES: CC(=O)Oc1c(C)cc(OCC(O)CNC(C)C)c(C)c1C] |
| timolol | 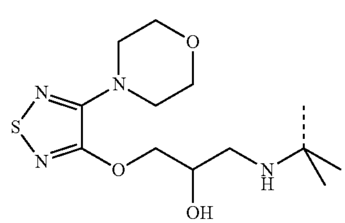 |

Although not necessarily depicted, those skilled in the art will appreciate that bioactive agents of general formulae described herein may have particular stereoisomeric structures and possibly, particular geometric isomeric structures. For avoidance of any doubt, the general formulae shown herein are intended to embrace all such structures. Stereoisomeric structures can include the (S)-enantiomer or the (R)-enantiomer of the bioactive agent, as well as racemic mixtures.

For example, the β-blocker timolol has (S) and (R) enantiomers of the following structures:

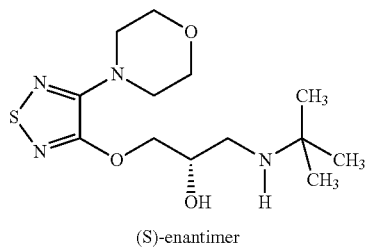

(S)-enantimer

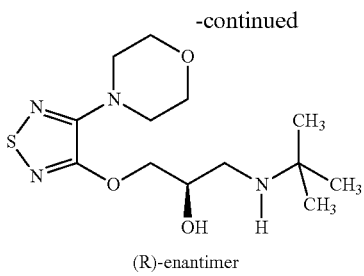

(R)-enantimer

When a bioactive agent can exist in different stereoisomers, the polymer-bioactive agent conjugate may be enriched in one stereoisomer. In one set of embodiments, the polymer-bioactive agent conjugate may comprise at least 70%, at least 80%, at least 90% or at least 95% of the drug as one enantiomer.

In one set of embodiments, where the polymer-bioactive agent conjugate comprises a β-blocker, it may comprise the (S)-enantiomer of the β-blocker, such as for example, the (S)-enantiomer of timolol.

Polymer-bioactive agent conjugates of the invention comprise at least one bioactive agent selected from the group consisting of prostaglandin analogues and β-blockers conjugated to the polymer backbone. More typically, polymer conjugates of the invention comprise a plurality of bioactive agents selected from prostaglandin analogues, β-blockers, and mixtures thereof.

In one set of embodiments, polymer-bioactive agent conjugates of the invention comprise a moiety of formula (I):

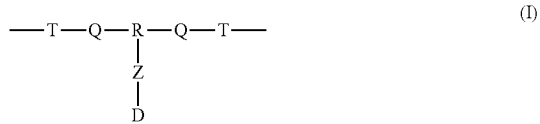

where:
T at each occurrence represents a triazole moiety;
Q is independently selected at each occurrence and may be present or absent and when present represents a linking group;
R is an optionally substituted linear or branched hydrocarbon and may comprise optionally substituted aromatic hydrocarbon or heteroaromatic hydrocarbon;
Z is a cleavable linking group; and
D is a releasable bioactive agent selected from a prostaglandin analogue of formula (X) and/or a β-blocker of formula (XX).

Prostaglandin analogues and β-blockers bound to polymer conjugates of the invention are releasable bioactive agents. The term "releasable" as used herein in connection with bioactive agents mean that the bioactive agents are capable of being covalently decoupled or cleaved from the polymer backbone so as to be released into an environment in a biologically active or physiologically active form. For example, the bioactive agents are capable of being released or cleaved from the Z group defined in general formulae (I), (Ib), (IIa), (IIb), (IIIa), (IIIb), (VIa) and (VIb) above. Release of the bioactive agents may be promoted by the conjugates being exposed to physiological conditions or a biological environment. Upon being released, the bioactive agent is bioactive or will be converted in vivo or in vitro to a bioactive form (e.g. as in the case of a prodrug bioactive agent).

The ability of the bioactive agents to be releasable will generally be a result of the bioactive agents each being coupled to the polymer backbone in pendant form via a cleavable linking group, which is represented by the moiety "Z" in formulae described herein. The cleavable linking group may couple the bioactive agent to the polymer backbone directly, or through a spacer moiety. Cleavage of the cleavable linking group will therefore promote release of the bioactive agent. Some specific examples of Z are described below.

In one embodiment, the prostaglandin analogues and β-blockers are released such that they do not include a residue derived from the polymer backbone or linking group Z. By this it is meant that each bioactive agent is released in their substantially original form (i.e. before being conjugated) and are essentially free from, for example, fragments of oligomer or polymer derived from the polymer backbone and/or group(s) linking the bioactive agent to the polymer backbone. Accordingly, in this respect, the linking group Z in formulae described herein is considered to be a part of the polymer backbone of the conjugate.

In the moieties of formulae (I), (Ib), (IIa), (IIb), (IIa), (IIIb), (VIa) and (VIb), the bioactive agent (D) is coupled to R through a cleavable linking group denoted by Z. As used herein "linking group" refers to a generally divalent substituent group that couples D to R. The substituent group is cleavable so that the bioactive agent is releasable.

In some embodiments, the cleavable linking group represented by Z is a cleavable covalent bond that directly couples the bioactive agent to the polymer backbone.

In other embodiments, the cleavable linking group represented by Z comprises a spacer moiety and a cleavable covalent bond. The spacer moiety is attached to the polymer backbone while the cleavable covalent bond couples the spacer moiety to the bioactive agent. In some embodiments of a polymer-bioactive conjugate of the invention, it is a proviso that Z does not include a triazole moiety. Thus, polymer conjugates of the invention do not include bioactive agents coupled to the polymer backbone via a product of a click chemistry reaction.

The covalent bond coupling the bioactive agent (D) with the linking group (Z) is not a carbon-carbon bond. Accordingly, the cleavable covalent bond will generally form part of a functional group selected from: esters; carbonates; and anhydrides. Of these functional groups, esters and carbonates are preferred. A skilled person would recognise that such groups are capable of being cleaved, for example hydrolytically, enzymatically, and/or by radical mechanisms, so as to release the bioactive agent.

The present invention preferably employs a group selected from ester, anhydride and carbonate linking groups to conjugate the bioactive agent to the polymer backbone as such linking groups have been found to be hydrolytically labile in biological environments. Such linking groups may also be generally more labile than other groups or moieties that may be present in the polymer-bioactive agent conjugate, such as for example, biodegradable moieties that may be present in the polymer backbone of polymer conjugates of some embodiments of the invention. Ester, anhydride and carbonate linking groups may further help to ensure that a sufficient amount of the drug is effectively released from the polymer conjugate to achieve therapeutic levels in the immediate vicinity of the polymer conjugate material.

As discussed above, prostaglandin analogues delivered by polymer-bioactive agent conjugates of the invention comprise at least one functional group selected from the group consisting of a carboxylic acid group at the 1 position, a hydroxy group at the 9 position, a hydroxy group at the 11 position, and a hydroxy group at the 15 position. When the bioactive agent is a prostaglandin analogue, the cleavable covalent bond forms part of an ester, carbonate or anhydride, depending on whether the drug is linked to the polymer backbone via the 1, 9, 11 or 15 position.

The β-blockers delivered by polymer-bioactive agent conjugates of the invention comprise a beta-amino alcohol group. When the bioactive agent is a β-blocker, the cleavable covalent bond forms part of an ester or carbonate group as the bioactive agent is conjugated to the polymer backbone via the alcohol (—OH) moiety of the beta-amino alcohol group.

When present, the prostaglandin analogues of formula (X) and the β-blockers of formula (XX) as shown above are each coupled to the polymer backbone by the group Z.

When the bioactive agent is a prostaglandin analogue of formula (Xb), the drug and Z form an ester or anhydride linking group. Accordingly, in formula (Xb), the prostaglandin drug is covalently linked to Z so as to form part of an ester linkage or an anhydride linkage. In such embodiments, the prostaglandin analogue will comprise the acid residue of the ester or anhydride linking group, while Z will comprise the alcohol residue of the ester or the acid residue of the anhydride linking group. Upon hydrolysis or cleavage of the ester or anhydride linking group, a carboxylic acid group will then form on the prostaglandin analogue, while an alcohol (—OH) group or carboxylic acid (—$CO_2H$) group will form on Z.

When the bioactive agent is a prostaglandin analogue of formula (Xa), (Xc) or (Xd), or a β-blocker of formula (XXa), (XXb) or (XXc), the bioactive agent and Z together form an ester or carbonate linking group. In formulae (Xa), (Xc), (Xd), (XXa), (XXb), or (XXc) the prostaglandin analogue or β-blocker is covalently linked to Z so as to form part of an ester linkage or a carbonate linkage. In such embodiments, the bioactive agent (i.e. prostaglandin analogue or β-blocker) will comprise the alcohol residue of the ester or carbonate linking group, while Z will comprise the acid residue of the ester or carbonate linking group. Upon hydrolysis or cleavage of the ester or carbonate linking group, an alcohol (—OH) group will then form on the prostaglandin analogue, while a carboxylic acid (—$CO_2H$) group or a carbonic acid ester (—O(O)COH) group will form on Z. It will be recognised by those skilled in the art that the carbonic acid residue will spontaneously decompose to generate an alcohol residue of the linking group and $CO_2$.

Breakdown of the cleavable covalent bond can be promoted hydrolytically (i.e. hydrolytic cleavage) and may take place in the presence of water and an acid or a base. In some embodiments the cleavage may take place in the presence of one or more hydrolytic enzymes or other endogenous biological compounds that catalyze or at least assist in the cleavage process. For example, an ester bond may be hydrolytically cleaved to produce a carboxylic acid and an alcohol.

At the very least the bioactive agent will be releasable from the conjugate per se. However, as further described below, the polymer backbone may also biodegrade in vivo or in vitro such that the polymer backbone breaks into lower molecular weight fragments, with the bioactive agent remaining tethered to such a fragment(s) via Z. In that case, the bioactive agent will nevertheless still be capable of being released or cleaved from Z, which may or may not still be associated with the polymer conjugate per se.

As indicated above, bioactive agents as described herein may be coupled to a spacer moiety, which in turn is attached to the polymer backbone. As used herein, the terms "spacer", "spacer group" or "spacer moiety" refer to an atom or any straight chain or branched, symmetric or asymmetric compound capable of linking or coupling the bioactive agent to a polymer backbone.

In some embodiments, the "spacer", "spacer group" or "spacer moiety" refers to a substituent which is generally divalent. As outlined above, the covalent bond between the spacer moiety and the bioactive agent is cleavable so that the bioactive agent is releasable.

Examples of suitable spacer moieties that may form part of Z include the divalent form of a group selected from oxy (—O—), alkyl, alkenyl, alkynyl, aryl, acyl (including —C(O)—), carbocyclyl, heterocyclyl, heteroaryl, alkyloxy, alkenyloxy, alkynyloxy, aryloxy, acyloxy, carbocyclyloxy, heterocyclyloxy, heteroaryloxy, alkylthio, alkenylthio, alkynylthio, arylthio, acylthio, carbocyclylthio, heterocyclylthio, heteroarylthio, alkylalkenyl, alkylalkynyl, alkylaryl, alkylacyl, alkylcarbocyclyl, alkylheterocyclyl, alkylheteroaryl, alkyloxyalkyl, alkenyloxyalkyl, alkynyloxyalkyl, aryloxyalkyl, alkylacyloxy, alkyloxyacylalkyl, alkylcarbocyclyloxy, alkylheterocyclyloxy, alkylheteroaryloxy, alkylthioalkyl, alkenylthioalkyl, alkynylthioalkyl, arylthioalkyl, alkylacylthio, alkylcarbocyclylthio, alkylheterocyclylthio, alkylheteroarylthio, alkylalkenylalkyl, alkylalkynylalkyl, alkylarylalkyl, alkylacylalkyl, arylalkylaryl, arylalkenylaryl, arylalkynylaryl, arylacylaryl, arylacyl, arylcarbocyclyl, arylheterocyclyl, arylheteroaryl, alkenyloxyaryl, alkynyloxyaryl, aryloxyaryl, arylacyloxy, arylcarbocyclyloxy, arylheterocyclyloxy, arylheteroaryloxy, alkylthioaryl, alkenylthioaryl, alkynylthioaryl, arylthioaryl, arylacylthio, arylcarbocyclylthio, arylheterocyclylthio, and arylheteroarylthio, wherein where present the or each —$CH_2$— group in any alkyl chain may be replaced by a divalent group independently selected from —O—, —OP(O)$_2$—, —OP(O)$_2$O—, —S—, —S(O)—, —S(O)$_2$O—, —OS(O)$_2$O—, —N≡N—, —OSi(OR$^a$)$_2$O—, —Si(OR$^a$)$_2$O—, —OB(OR$^a$)O—, —B(OR$^a$)O—, —NR$^a$—, —C(O)—, —C(O)O—, —OC(O)O—, —OC(O)NR$^a$— and —C(O)NR$^a$—, where the or each R$^a$ may be independently selected from hydrogen, alkyl, alkenyl, alkynyl, aryl, carbocyclyl, heteroaryl, heterocyclyl, arylalkyl, and acyl. The one or more R$^a$ groups may also be independently selected from hydrogen, $C_{1-18}$alkyl, $C_{1-18}$alkenyl, $C_{1-18}$alkynyl, $C_{6-18}$aryl, $C_{3-18}$carbocyclyl, $C_{3-18}$heteroaryl, $C_{3-18}$heterocyclyl, and $C_{7-18}$arylalkyl.

In some embodiments the spacer moiety may be branched. Where the spacer moiety is branched, two or more releasable bioactive agents may be appended to the spacer moiety.

In the lists above defining groups (generally divalent) from which each spacer moiety may be selected, each alkyl, alkenyl, alkynyl, aryl, carbocyclyl, heteroaryl, and heterocyclyl moiety may be optionally substituted. For avoidance of any doubt, where a given spacer moiety contains two or more of such moieties (e.g. alkylaryl), each of such moieties may be optionally substituted with one, two, three or more optional substituents as herein defined.

In the lists above defining groups (generally divalent) from which the or each spacer moiety may be selected, where a given spacer moiety contains two or more subgroups (e.g. [group A][group B]), the order of the subgroups is not intended to be limited to the order in which they are presented. Thus, a spacer moiety with two subgroups defined as [group A][group B] (e.g. alkylaryl) is intended to also be a reference to a spacer moiety with two subgroups defined as [group B][group A] (e.g. arylalkyl).

Some specific examples of spacer moieties that may form part of Z include: —O—; —C(O)—; —OC(O)— and optionally substituted: —OC(O)—$C_{1-18}$alkylene-C(O)—; —C(O)O—$C_1$-$C_{18}$alkylene-C(O)—; —O—Ar—C(O)O—; —O—Ar—C(O)—$NR^a$—; —O—Ar—; —O—Ar—; —C(O)O—Ar—C(O)O—; —C(O)O—Ar—C(O)—$NR^a$—; —C(O)O—Ar—; —C(O)O—Ar—; —$NR^a$C(O)—$C_1$-$C_{18}$alkylene-C(O)—; —C(O)O—$C_1$-$C_{18}$alkylene-O—; —O—$C_1$-$C_{18}$alkylene-O—; —O—$C_1$-$C_{18}$alkylene-$NR^a$—; —OC(O)—$C_1$-$C_{18}$alkylene-$NR^a$—; —C(O)—$C_1$-$C_{18}$alkylene-$NR^a$—; —OC(O)—$C_1$-$C_{18}$alkylene-O—; —C(O)—$C_1$-$C_{18}$alkylene-O—; and —C(O)$NR^a$—$C_1$-$C_{18}$alkylene-$NR^a$— where $R^a$ is as defined above.

In one form of the invention, exemplary spacer moieties include: —O—; —C(O)—; and —OC(O)—$C_{1-18}$alkylene-C(O)—, such as —OC(O)—$C_{2-3}$alkylene-C(O)—, —O—$C_{5-6}$Ar—C(O)O and —C(O)O—$C_{5-6}$Ar—C(O)O—.

The choice of spacer moieties will determine the spacing of the bioactive agents from the polymer backbone. The skilled artisan would be capable of selecting the appropriate spacer moiety based on an evaluation of steric constraints, phase chemistry and surface chemistry. For example, larger bioactive agents can be advantageously spaced from the monomer by the choice of a longer spacer moiety.

In some embodiments of a polymer conjugate of the invention, (a) the bioactive agent (D) is a prostaglandin analogue of formula (X), wherein $R^1$ is the acid residue (—C(O)O—) of an ester or anhydride linking group and Z is of a formula selected from the group consisting of:

(i) (R) —O— (D);
(ii) (R) -J-Ar—O— (D);
(iii) (R) -J-$C_1$-$C_{12}$alkylene-O— (D);
(iv) (R) -J-Ar-J-$C_1$-$C_{12}$alkylene-O— (D);
(v) (R) -J-$C_1$-$C_{12}$alkylene-J-Ar—O— (D);
(vi) (R) -J-$C_1$-$C_{12}$alkylene-J-Ar-Q-$C_1$-$C_{12}$alkylene-O— (D);
(vii) (R) —OC(O)— (D);
(Viii) (R) -J-Ar—OC(O)— (D); and
(ix) (R) -J-$C_1$-$C_{12}$alkylene-OC(O)— (D);
or (b) the bioactive agent (D) is a prostaglandin analogue of formula (X) wherein one of $R^9$, $R^{11}$ and $R^{15}$ is the hydroxy residue (—O—) of an ester or carbonate linking group and Z is of formula selected from the group consisting of (i) (R) —C(O) (D);
(ii) (R) -J-Ar—C(O)— (D);
(iii) (R) -J-$C_1$-$C_{12}$alkylene-C(O)— (D);
(iv) (R) -J-Ar-J-$C_1$-$C_{12}$alkylene-C(O)— (D);
(v) (R) -J-$C_1$-$C_{12}$alkylene-J-Ar—C(O) (D);
(vi) (R) -J-$C_1$-$C_{12}$alkylene-J-Ar-J-$C_1$-$C_{12}$alkylene-C(O)— (D);
(vii) (R) —OC(O)— (D);
(viii) (R) -J-Ar—OC(O)— (D);
(ix) (R) -J-$C_1$-$C_{12}$alkylene-OC(O)— (D); and
(x) (R) -J-Ar-J-$C_1$-$C_{12}$alkylene-OC(O)— (D).

wherein:

(R) indicates the end of the linking group bonded to the R group in the polymer backbone and (D) indicates the end of the linking group bonded to the prostaglandin drug;

Ar is optionally substituted aromatic or heteroaromatic hydrocarbon; and

J is selected from the group consisting of —O—, —C(O)—, —O—C(O)—, —C(O)—O—, —C(O)OC(O)—, —C(O)$NR^a$C(O)—, —OC(O)$NR^a$—, —$NR^a$C(O)O—, —$NR^a$—, —$NR^a$C(O)$NR^a$—, —$NR^a$C(O)—, —C(O)$NR^a$—, —S—, —O—C(S)—, —C(S)—O—, —S—C(O)—, —C(O)—S—, —$NR^a$C(S)—, and —C(S)$NR^a$—, where $R^a$ is hydrogen or $C_1$ to $C_6$ alkyl.

The terms "aromatic hydrocarbon" and "heteroaromatic hydrocarbon", including indefinition of R and Z (in connection with the group "Ar") denotes any ring system comprising at least one aromatic or heteroaromatic ring. The aromatic hydrocarbon or heteroaromatic hydrocarbon may be optionally substituted by one or more optional substituents as described herein.

The aromatic hydrocarbon or heteroaromatic hydrocarbon may comprise a suitable number of ring members. In some embodiments, the aromatic hydrocarbon or heteroaromatic hydrocarbon comprises from 5 to 12 ring members. The term "ring members" denotes the atoms forming part of the ring system. In an aryl group, the ring atoms are each carbon. In a heteroaromatic hydrocarbon group one or more of the rings atoms are heteroatoms. Examples of heteroatoms are O, N, S, P and Se, particularly O, N and S. When two or more heteroatoms are present in a heteroaromatic hydrocarbon group, the heteroatoms may be the same or different at each occurrence.

Suitable aromatic hydrocarbon may be selected from the group consisting of phenyl, biphenyl, naphthyl, tetrahydronaphthyl, idenyl, azulenyl, and the like.

Suitable heteroaromatic hydrocarbon may be selected from the group consisting of furanyl, thiophenyl, 2H-pyrrolyl, pyrrolinyl, oxazolinyl, thiazolinyl, indolinyl, imidazolidinyl, imidazolinyl, pyrazolyl, pyrazolinyl, isoxazolidinyl, isothiazolinyl, oxadiazolinyl, triazolinyl, thiadiazolinyl, tetrazolinyl, pyridinyl, pyridazinyl, pyrimidinyl, pyrazinyl, triazenyl, indolyl, isoindolinyl, benzimidazolyl, benzoxazolyl, quinolinyl, isoquinolinyl, and the like.

In some embodiments of the invention, Ar is an optionally substituted $C_{5-12}$ aromatic hydrocarbon. In some embodiments Ar is optionally substituted phenyl ($C_6$ aromatic hydrocarbon). In some specific embodiments, Ar is para or meta substituted phenyl. In some specific embodiments, Ar is optionally substituted pyridyl ($C_5$ heteroaromatic).

In some embodiments of a polymer-bioactive agent conjugate of the invention, when the bioactive agent (D) is a prostaglandin analogue linked via $R^1$ to the polymer backbone, then Z is of a formula selected from the group consisting of:

(R) —O— (D);
(R) —OC(O)—Ar—O— (D);
(R) —NHC(O)—Ar—O— (D);
(R) —C(O)O—$C_{1-12}$alkylene-O— (D);
(R) —OC(O)—$C_1$-$C_{12}$alkylene-O— (D).
(R) —OC(O)— (D);
(R) —OC(O)—Ar—OC(O)— (D);
(R) —NHC(O)—Ar—OC(O)— (D);
(R) —C(O)O—$C_1$-$C_{12}$alkylene-OC(O)— (D); and
(R) —OC(O)—$C_1$-$C_{12}$alkylene-OC(O)— (D).

In one embodiment, when the prostaglandin analogue (D) is linked via R1 to the polymer backbone, then Z is —O—; —OC(O)—; —O—$C_6$-aryl-C(O)O—; —O—$C_6$-aryl-C(O)NH—; —O-Pyridoxine-; and —O-Phloroglucinol-.

In some embodiments of a polymer-bioactive agent conjugate of the invention, when the bioactive agent (D) is a prostaglandin analogue linked via one of $R^9$, $R^{11}$ and $R^{15}$ to the polymer backbone, then Z is of a formula selected from the group consisting of:

(R) —C(O) (D);
(R) —OC(O)— (D);
(R) —OC(O)—$C_1$-$C_{12}$alkylene-C(O)— (D);
(R) —NHC(O)—$C_1$-$C_{12}$alkylene-C(O)— (D);
(R) —OC(O)—$C_1$-$C_{12}$alkylene-OC(O)— (ID);

(R) —NHC(O)—C$_1$-C$_{12}$alkylene-OC(O)— (D);
(R) —OC(O)—Ar—C(O)— (D);
(R) —NHC(O)—Ar—C(O)— (D);
(R) —OC(O)—Ar—OC(O)— (D); and
(R) —NHC(O)—Ar—OC(O)— (D).

In a specific embodiment, when the prostaglandin analogue is linked via one of R$^9$, R$^{11}$ and R$^{15}$ to the polymer backbone, then Z is —C(O)—; —C(O)—C$_1$-C$_5$alkylene-C(O)O—; )-; —C(O)—C$_1$-C$_5$alkylene-C(O)NH—; —C(O)O—; —C(O)O—C$_6$-aryl-C(O)O—; —C(O)O—C$_6$-aryl-C(O)NH—; —C(O)O-Pyridoxine-; and —C(O)O-Phloroglucinol-.

In some embodiments of a polymer conjugate of the invention, the bioactive agent (D) is a β-blocker of formula (XX), and Z is of a formula selected from the group consisting of:

(i) (R) —C(O)— (D);
(ii) (R) —OC(O)— (D);
(iii) (R) -J-Ar—C(O)— (D);
(iv) (R) -J-Ar—OC(O)— (D);
(v) (R) -J-C$_1$-C$_{12}$alkylene-C(O)— (D);
(vi) (R) -J-C$_1$-C$_{12}$alkylene-OC(O)— (D);
(vii) (R) -J-Ar-J-C$_1$-C$_{12}$alkylene-C(O)— (D);
(viii) (R) -J-Ar-J-C$_1$-C$_{12}$alkylene-OC(O)— (D);
(ix) (R) -J-C$_1$-C$_{12}$alkylene-J-Ar—C(O) (D);
(x) (R) -J-C$_1$-C$_{12}$alkylene-J-Ar—OC(O) (D);
(xi) (R) -J-C$_1$-C$_{12}$alkylene-J-Ar-J-C$_1$-C$_{12}$alkylene-C(O)— (D); and
(xii) (R) -J-C$_1$-C$_{12}$alkylene-J-Ar-J-C$_1$-C$_{12}$alkylene-OC(O)— (D), wherein:
(R) indicates the end of the linker bonded to the R group in the polymer backbone and (D) indicates the end of the linker bonded to the β-blocker drug;
Ar is optionally substituted aryl or heteroaryl;
J is selected from the group consisting of —O—, —C(O)—, —O—C(O)—, —C(O)—O—, —C(O)OC(O)—, —C(O)NR$^a$C(O)—, —OC(O)NR$^a$—, —NR$^a$C(O)O—, —NR$^a$—, —NR$^a$C(O)NR$^a$—, —NR$^a$C(O)—, —C(O)NR$^a$—, —S—, —O—C(S)—, —C(S)—O—, —S—C(O)—, —C(O)—S—, —NR$^a$C(S)—, and —C(S)NR$^a$—; and
R$^a$ is hydrogen or C$_1$ to C$_6$ alkyl (preferably H or C$_1$ to C$_4$ alkyl).

In some embodiments of a polymer-bioactive agent conjugate of the invention, when the bioactive agent (D) is a β-blocker of formula (XX), then Z is of a formula selected from the group consisting of:

(R) —C(O) (D);
(R) —OC(O)— (D);
(R) —OC(O)—C$_1$-C$_{12}$alkylene-C(O)— (D);
(R) —NHC(O)—C$_1$-C$_{12}$alkylene-C(O)— (D);
(R) —OC(O)—C$_1$-C$_{12}$alkylene-OC(O)— (D);
(R) —NHC(O)—C$_1$-C$_{12}$alkylene-OC(O)— (D);
(R) —OC(O)—Ar—C(O)— (D);
(R) —NHC(O)—Ar—C(O)— (D);
(R) —OC(O)—Ar—OC(O)— (D);
(R) —NHC(O)—Ar—OC(O)— (D).

In a specific embodiment, when the β-blocker is linked to the polymer backbone, then Z is —C(O)—; —C(O)—C$_{1-5}$alkylene-C(O)O—; —C(O)—C$_{1-5}$alkylene-C(O)NH—; —C(O)O—; —C(O)O—C$_6$-aryl-C(O)O—; —C(O)O—C$_6$-aryl-C(O)NH—; —C(O)O-Pyridoxine-; and —C(O)O-Phloroglucinol-.

Conjugates of the invention may, in addition to moieties of formula (I) or (Ib), comprise a linker segment as a part of its polymer backbone structure. The linker segment may be coupled to one or more moieties of formula (I) or (Ib). Each coupling to a moiety of formula (I) or (Ib) occurs via a triazole moiety. Thus, when present, the linker segment may be used to space apart moieties of formula (I) or (Ib) in the conjugates.

As used herein, the term "linker segment" refers to a segment that is generally a divalent.

The presence of a linker segment can be advantageous, as it enables the physical properties of the conjugates to be adjusted by selection of a desired linker segment, thus providing avenues for macromolecules tailored for use in particular applications. For example, hard segments and/or soft segments may be incorporated into the polymer backbone of the conjugates through the selection of an appropriate linker segment.

The linker segment may be introduced to the polymer backbone of the polymer-bioactive agent conjugate by polymerising a monomer comprising a pendant bioactive agent with a co-monomer comprising a linker moiety. In such embodiments the linker segment may be derived from the linker moiety of the co-monomer.

In some embodiments, the linker segment may be selected from the group consisting of optionally substituted linear or branched aliphatic hydrocarbon, optionally substituted carbocyclyl, optionally substituted heterocyclyl, optionally substituted aryl, optionally substituted heteroaryl, an optionally substituted polymeric linker segment, and combinations thereof.

Optionally substituted linear or branched aliphatic hydrocarbon linker segments may be selected from optionally substituted C$_1$ to C$_{20}$, C$_1$ to C$_{10}$ or C$_1$ to C$_6$ linear or branched aliphatic hydrocarbons. The aliphatic hydrocarbons may be saturated or unsaturated hydrocarbon. Optionally substituted aliphatic hydrocarbon linker segments may be derived from fatty acids (such as acetic acid, propionic acid, butyric acid, valeric acid and caproic acid), sugar alcohols (such as xylitol and mannitol), and amino acids (such as glutamic acid and lysine).

Optionally substituted carbocyclyl linker segments may comprise from 3 to 12, 3 to 8 or 5 to 6 carbon ring members.

Optionally substituted heterocyclyl linker segments may comprise from 3 to 12, 3 to 8 or 5 to 6 ring members and 1, 2, 3, 4 or more heteroatoms as a part of the ring. The heteroatoms may be independently selected from the group consisting of O, N and S.

Optionally substituted aryl linker segments may comprise from 3 to 12, 3 to 8 or 5 to 6 carbon ring members and at least one unsaturation.

Optionally substituted heteroaryl linker segments may comprise from 3 to 12, 3 to 8 or 5 to 6 ring members and 1, 2, 3, 4 or more heteroatoms as a part of the ring. The heteroatoms may be independently selected from the group consisting of O, N and S. The heteroaryl linker segment also comprises at least one unsaturation.

Optionally substituted polymeric linker segments may comprise any suitable polymer or copolymer. In some embodiments, it can be desirable for the polymer to be biocompatible and/or biodegradable. One skilled in the relevant art would be able to select suitable biocompatible and/or biodegradable polymers. Exemplary biocompatible polymers may be selected from polyethers, polyesters, polyamides, polyurethanes, and copolymers thereof. Copolymers may be for example, poly(ether-esters), poly(urethane-ethers), poly(urethane-esters), poly(ester-amides) and the like. Preferred biocompatible polymers are polyethers, polyesters, polyurethanes, and copolymers thereof.

Exemplary polyethers may be polymers of $C_2$ to $C_4$ alkylene diols, such as polyethylene glycol and polypropylene glycol, preferably polyethylene glycol.

Exemplary polyesters may be polycaprolactone, poly(lactic acid), poly(glycolic acid) and poly(lactic-co-glycolic acid).

In one form, the polymeric linker segment may comprise a biodegradable polymer. Suitable biodegradable polymers may comprise at least one biodegradable moiety selected from the group consisting of an ester, an amide, a urethane (carbamate), a urea and a disulfide moiety, preferably an ester or urethane moiety. Biodegradable polymers used in the polymeric linker segment may have a combination of such moieties.

The linker segment may modify the properties of the conjugate and influence bioactive agent release. For example, a polyether linker segment (e.g. polyethylene glycol) may make the conjugate more hydrophilic. Without wishing to be limited by theory, it is believed that a conjugate comprising a hydrophilic segment as part of its polymer backbone could promote release of the bioactive agent. This may be advantageous where more rapid release of the bioactive agent is desired. Conversely, a conjugate comprising a hydrophobic segment as part of its backbone might delay release of the bioactive agent. A hydrophobic segment could be introduced by incorporation of a hydrophobic polymeric linker (e.g. a polycarpolactone linking moiety) into the conjugate.

In one set of embodiments, the polymer-bioactive agent conjugate comprises a polyether segment as part of the polymer backbone. The polyether segment may be derived from polyethylene glycol (PEG). In some embodiments, the polyether segment is derived from a PEG having a molecular weight in the range of from about 200 to 10,000, preferably from about 200 to about 3000.

In some embodiments, the triazole moieties in the polymer backbone may provide hard segments, which influence the properties of the polymer-bioactive agent conjugates.

In some embodiments, it may be desirable for polymer-bioactive agent conjugates of one or more embodiments of the invention to be biodegradable.

By being "biodegradable" in the context of the invention is meant that the polymer undergoes with the passage of time substantial degradation under physiological conditions or in a biological environment. In other words, the polymer has a molecular structure that is susceptible to break down (i.e. a reduction in molecular weight) by chemical decomposition in a biological environment (e.g. within a subject or in contact with biological material such as blood, tissue etc), as opposed to physical degradation. Such chemical decomposition will typically be via the hydrolysis of labile or biodegradable moieties that form part of the molecular structure of the polymer.

The presence of a biodegradable polymeric linker segment in the polymer backbone may confer biodegradability to the polymer conjugates of the invention.

Labile or cleavable functional groups present in the polymer backbone may also be susceptible to degradation, leading to the production of lower molecular weight fragments upon erosion of the polymer conjugates.

Biodegradable polymer conjugates of the invention may comprise a combination of degradable groups. For example, the conjugates may comprise a biodegradable polymeric linker, as well as cleavable functional groups, as part of the polymer backbone.

In some embodiments, polymer-bioactive agent conjugates of the invention may be formed by reacting a monomer of formula (IV):

where:

X may be the same or different at each occurrence and represents a terminal functional group comprising an alkyne or an azide functionality;

Q is independently selected at each occurrence and may be present or absent and when present, represents a linking group;

R is an optionally substituted linear or branched hydrocarbon and may comprise optionally substituted aromatic hydrocarbon or heteroaromatic hydrocarbon;

Z is a cleavable linking group; and

D is a bioactive agent selected from the group consisting of prostaglandin analogues and β-blockers, with at least one monomer of complementary functionality.

In some embodiments, polymer-bioactive agent conjugates of the invention may be formed by reacting at least one monomer of formula (IV):

where X, Q, R, Z and D are as herein defined, with at least one monomer of complementary functionality.

In the monomer of formula (IV), the groups Q, R, Z and D may be selected from any one of the moieties as described herein for such groups.

In one set of embodiments, the monomer of complementary functionality may be a monomer of formula (V):

where:

A may be the same or different at each occurrence and represents a group comprising a terminal functional group selected from the group consisting of an alkyne and an azide, wherein said terminal functional group is complementary to the terminal functional group of X;

L is an optionally substituted linker group; and n is an integer and is at least 1.

In another set of embodiments, the monomer of complementary functionality may be a further monomer of formula (IV). In such embodiments at least two monomers of formula (IV) may react together, provided the monomers of formula (IV) have complementary terminal functionality.

In some embodiments monomers of formula (IV) having complementary terminal functionality may be homofunctional. That is, each of the co-monomers may comprise one type of terminal functional group. The terminal functional groups of the co-monomers would be complementary and capable of reacting with one another to form a triazole moiety. For example, one co-monomer of formula (IV) may comprise a terminal functional group comprising an alkyne functionality while the other co-monomer of formula (IV)

comprises a terminal functional group comprising an azide functionality. These co-monomers would be able to copolymerise under appropriate conditions to form a polymer conjugate having triazole moieties in the polymer backbone.

Examples of complementary monomers of formula (IV) that are capable of copolymerising to form a polymer-bioactive agent conjugate are shown in formula (IVa) and formula (IVb):

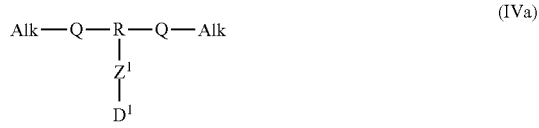

(IVa)

where:

Alk represents a terminal functional group comprising an alkyne functionality;

Q is independently selected at each occurrence and may be present or absent and when present, represents a linking group;

R is an optionally substituted linear or branched hydrocarbon and may comprise optionally substituted aromatic hydrocarbon or heteroaromatic hydrocarbon;

$Z^1$ is a cleavable linking group; and $D^1$ is a bioactive agent selected from the group consisting of prostaglandin analogues and β-blockers,

(IVb)

where:

Az represents a terminal functional group comprising an azide functionality;

Q is independently selected at each occurrence and may be present or absent and when present, represents a linking group;

R is an optionally substituted linear or branched hydrocarbon and may comprise optionally substituted aromatic hydrocarbon or heteroaromatic hydrocarbon;

$Z^2$ is a cleavable linking group; and $D^2$ is a bioactive agent selected from the group consisting of prostaglandin analogues and β-blockers.

One skilled in the art would appreciate that the terminal functional groups represented by Alk and Az in formulae (IVa) and (IVb) may be reversed. That is, the group Az may be present on formula (IVa) and the group Alk may be present on formula (IVb) in some embodiments.

The terminal functional groups represented by Alk and Az on the co-monomers of formula (IVa) and (IVb) can react to produce a triazole moiety. The triazole moiety may be of formula (II), (III) or (IX) as described herein.

A polymer-bioactive agent conjugate of the invention produced from the copolymerisation of monomers of formula (IVa) and (IVb) may comprise a moiety of formula (Ib) as described herein. The monomers of formula (IVa) and (Vb) may react with one another in a mole ratio of 1:1.

The terminal functional groups represented by Alk in formulae described herein may be straight chain aliphatic or cycloaliphatic groups comprising an alkyne functionality. Cycloaliphatic terminal functional groups may comprise from 4 to 12 ring members, preferably from 7 to 8 ring members. Cycloaliphatic alkyne containing terminal functional groups may be advantageous in strain-promoted catalyst free cycloadditions with azides to form triazole moieties.

A monomer-bioactive agent conjugate of formula (IVa) that may be used in preparing the polymer conjugates of the invention may have one of the following structures, (IVai) and (IVaii), where the alkyne functionality is part of a terminal functional group as a terminal alkyne or an internal alkyne:

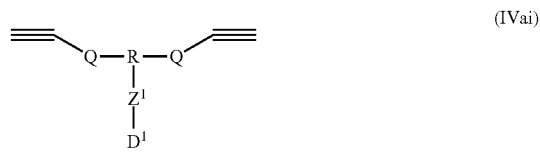

(IVai)

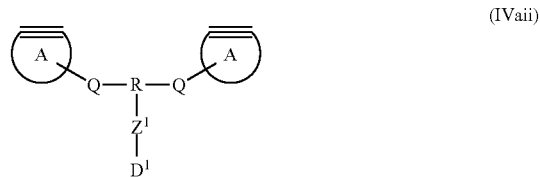

(IVaii)

A monomer-bioactive agent conjugate of formula (IVb) that may be used in preparing the polymer conjugates of the invention may have the following structure (IVbi):

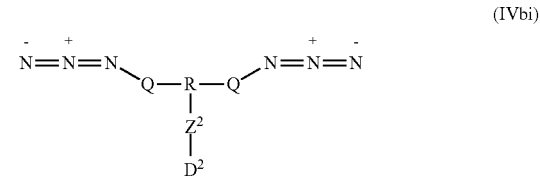

(IVbi)

In monomers of formula (IVa) and (IVb), the groups Q and R may be independently selected at each occurrence from any one of the moieties described herein for such groups.

The groups $Z^1$ and $Z^2$ in the monomers of formula (IVa) and (IVb) respectively are each cleavable linking groups, which may be the same or different. $Z^1$ and $Z^2$ may each be independently selected from any one of the groups described herein for Z.

The groups $D^1$ and $D^2$ in the monomers of formula (IVa) and (IVb) respectively are each bioactive agents, which may be the same or different. $D^1$ and $D^2$ may each be independently selected from any one of the groups described herein for D.

In some embodiments monomers of formula (IV) having complementary terminal functionality may be heterofunctional and comprise at least two different types of terminal functional groups. The terminal functional groups on the different monomers would be complementary and capable of reacting with one another to produce a triazole moiety. The trizole moiety may be selected from any of the formulae described herein for such moieties. A heterofunctional monomer may polymerise with itself (homopolymerise) or with another monomer of complementary functionality (copolymerise) under appropriate conditions to form a polymer-bioactive agent conjugate.

An example of a monomer of formula (IV) that can polymerise to form a polymer-bioactive agent conjugate is shown in formula (IVc):

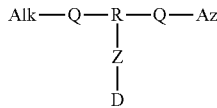
(IVc)

where:

Alk represents a terminal functional group comprising an alkyne functionality;

Az represents a terminal functional group comprising an azide functionality;

Q is independently selected at each occurrence and may be present or absent and when present, represents a linking group;

R is an optionally substituted linear or branched hydrocarbon and may comprise optionally substituted aromatic hydrocarbon or heteroaromatic hydrocarbon;

Z is a cleavable linking group; and

D is a bioactive agent selected from the group consisting of prostaglandin analogues and β-blockers.

Depending on the monomers used to prepare the polymer-bioactive agent conjugate, in some embodiments the polymer-bioactive conjugate of the invention may comprise a repeating unit of formula (VIa) or formula (VIb):

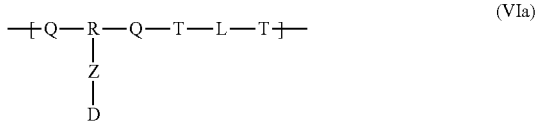
(VIa)

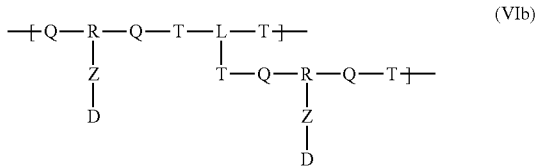
(VIb)

wherein in (VIa) and (VIb), T, Q, R, Z, D and L are as defined herein.

A repeating unit of formula (VIa) or (VIb) may occur when a monomer of formula (IV) reacts with a complementary monomer of formula (V).

In some embodiments, the polymer-bioactive conjugate of the invention may comprise a repeating unit of formula (VIc):

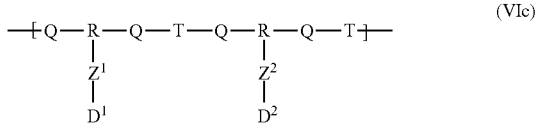
(VIc)

wherein T, Q, R, $Z^1$, $Z^2$, $D^1$ and $D^2$ are as defined herein.

A repeating unit of formula (VIc) may occur when two complementary monomers of formula (IV) react together.

A monomer which has a bioactive agent pendently attached thereto is referred to herein as a monomer-bioactive agent conjugate. An example of a monomer-bioactive agent conjugate is shown in formula (IV), as illustrated above.

In another aspect, the present invention provides a monomer-bioactive agent conjugate of formula (IV):

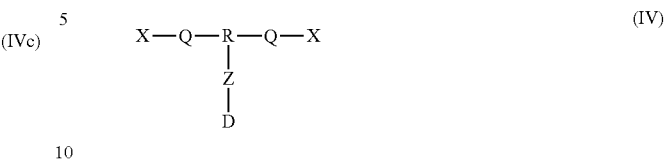
(IV)

where:

X may be the same or different at each occurrence and represents a terminal functional group comprising an alkyne or an azide functionality;

Q is independently selected at each occurrence and may be present or absent and when present, represents a linking group;

R is an optionally substituted linear or branched hydrocarbon and may comprise optionally substituted aromatic hydrocarbon or heteroaromatic hydrocarbon;

Z is a cleavable linking group; and

D is a bioactive agent selected from the group consisting of prostaglandin analogues and β-blockers.

In the monomer-bioactive agent conjugate of formula (IV) each X represents a group comprising a terminal functional group comprising an alkyne or azide functionality. The terminal functional group in X may be the same or different at each occurrence. Where the terminal functional groups (X) are the same, the monomer will generally be a diazide or dialkynyl monomer.

One skilled in the relevant art would understand that the terms "alkyne" and "azide" represent the following structures:

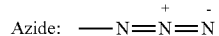

In one set of embodiments, the terminal functional group represented by X may comprise an optionally substituted straight chain aliphatic comprising an alkyne functionality. In such embodiments, X may comprise the alkyne functionality as a terminal alkyne. In one set of embodiments, group X comprises a terminal alkyne functionality. A terminal alkyne functionality may have a structure represented as follows:

In one set of embodiments, the terminal functional group represented by X comprises an optionally substituted cyclic group comprising an alkyne functionality. In such embodiments, the alkyne functionality may be regarded as an internal alkyne, as the alkyne functionality would be part of the ring structure of the cyclic group. An internal alkyne may have a structure represented as follows:

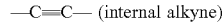

Internal alkynes contained in a cyclic group may be activated for participation in cycloaddition reactions by the presence of one or more substituent groups (e.g. electron withdrawing groups) present on the cyclic structure or by means of ring strain in the cyclic structure.

In one set of embodiments when X comprises an optionally substituted cyclic group comprising an alkyne functionality, the group may have a structure of formula (XV):

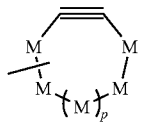
(XV)

where:
each M represents a ring atom and is independently selected from the group consisting of carbon (C), nitrogen (N), oxygen (O) and sulphur (S), with the proviso that at least 3 M is carbon; and
p is 1, 2 or 3, preferably p is 2.

In one embodiment, p is 1 and least one M is selected from the group consisting of N, O and S, preferably S.

In another embodiment, p is 2 and each M is carbon (C) or at least one M is selected from the group consisting of N, O and S, preferably S.

In another embodiment, p is 3 and each M is carbon (C).

Optional substituents that may be present in formula (XV) may be selected from the group consisting of hydroxy (—OH), —Oalkyl, alkyl, halo (preferably fluoro), cycloalkyl, heterocycloalkyl, aryl and heteroaryl. Cycloalkyl, heterocycloalkyl, aryl and heteroaryl substituent groups may each independently comprise from 3 to 6 ring atoms and may be fused to the cyclic group. The optional substituents may be located on any ring atom of the cyclic group. In one preference, one or more optional substituents are located at a ring atom ortho to the alkyne functionality.

In one set of embodiments X comprises a cycloalkyne of formula XVI

XVI wherein the cycloalkyne comprises from 7 to 9 constituent ring members selected from carbon and optionally including one or two heteroatom groups selected from sulfur and the group N—R$^t$ wherein R$^t$ is hydrogen, $C_1$ to $C_6$ alkyl or the group (Q) and wherein the ring is optionally substituted with at least one substituent selected from the group consisting of
hydroxy (preferably from 0 to 2 hydroxy);
oxo (i.e. =O) (preferably 0 or 1 oxo);
halo (preferably from 0 to 2 halo selected from chloro, bromo and fluoro and most preferably fluoro);
$C_1$ to $C_6$ alkoxy (preferably from 0 to 2 $C_1$ to $C_6$ alkoxy); and
rings fused with said ring of 7 to 9 constituent members wherein said fused rings include 0 to 3 rings each fused with said 7 to 9 membered ring and selected from benzene, cyclopropanone, and cyclopropane
wherein the fused benzene and cyclopropane rings are optionally further substituted with from one to three substituents selected from the group consisting of $C_1$ to $C_6$ alkyl, halo (preferably from 0 to 2 halo selected from chloro, bromo and fluoro and most preferably fluoro) and $C_1$ to $C_6$ alkoxy;
and wherein at least one ring member selected from nitrogen and carbon is bonded to Q.

The moiety "Q" present in formulae (I), (Ib), (IIa), (IIb), (IIIa), (IIIb), (IV), (IVa), (IVb), (IVc), (VIa), (VIb), (VIc), (IXa) and (IXb) defined herein may be present or absent at each occurrence. When present, Q represents a linking group, and is independently selected at each occurrence. Examples of Q that may be present in formulae (I), (Ib), (IIa), (IIb), (IIIa), (IIIb), (IV), (IVa), (IVb), (IVc), (VIa), (VIb), (VIc), (IXa) and (IXb) are described below.

In some embodiments of formulae (I), (Ib), (IIa), (IIb), (IIIa), (IIIb), (IV), (IVa), (IVb), (IVc), (VIa), (VIb), (VIc), (IXa) or (IXb), two Q are present and each Q is attached to the group "R". In other embodiments of formulae (I), (Ib), (IIa), (IIb), (IIIa), (IIIb), (IV), (IVa), (IVb), (IVc), (VIa), (VIb), (VIc), (IXa) or (IXb), one Q is present and one Q is absent.

in one set of embodiments, the linking group Q present in formulae defined herein may comprise a linking moiety. In some embodiments, the linking moiety may be an optionally substituted aliphatic moiety. A suitable aliphatic linking moiety may be selected from a saturated $C_1$ to $C_{20}$, $C_1$ to $C_{10}$ or $C_1$ to $C_6$ straight or branched aliphatic moiety. The aliphatic moiety may be optionally substituted by one or more substituents.

In monomer-bioactive agent conjugates described herein, the presence of a linking group Q connected to a terminal functional group comprising an alkyne or azide functionality may facilitate polymerisation of the monomer by reducing steric crowding around the terminal functional group.

In some embodiments, in the monomer of formula (IV), each Q-X is a group of formula (VII):

(VII)

where:
X is a terminal functional group comprising an alkyne or an azide functionality; and
m is an integer in the range of from 0 to 10.

In some embodiments of formula (VII), m is an integer in the range of from 1 to 5.

In some embodiments the linking group Q present in formulae defined herein may comprise a functional group. The functional group may be present in addition to the linking moiety. Thus, the linking moiety and the functional group together form the linking group Q.

In one set of embodiments Q comprises a functional group selected from the group consisting of an amide, ether, ester, urethane, urea, and carbonate ester functional group.

In some embodiments, the linking group Q may be represented by formula (VIII):

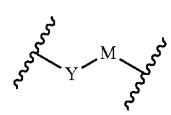
(VIII)

where:
Y represents a functional group; and
M represents a linking moiety.

In one embodiment, M may be an optionally substituted aliphatic linking moiety.

In monomers of formula (IV), when Q comprises a functional group, the group Q-X may be represented by formula (VIIIa):

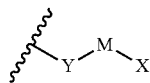

(VIIIa)

where:
Y is a functional group;
M is a linking moiety; and
X is a terminal functional group comprising an alkyne or an azide functionality.

In some embodiments. M is an optionally substituted saturated $C_1$ to $C_{20}$, $C_1$ to $C_{10}$ or $C_1$ to $C_6$ straight or branched aliphatic linking moiety.

In some embodiments the group Q-X in monomers of formula (IV) may be represented by formula (VIIIb):

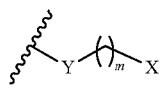

(VIIIb)

where:
Y is a functional group;
X is a terminal functional group comprising an alkyne or an azide functionality; and
m is an integer in the range of from 0 to 10.

In some embodiments of formula (VIIIb), m is an integer in the range of from 1 to 5.

The functional group represented by Y in formulae (VIII), (VIIIa) and (VIIIb) may be selected from the group consisting of an amide, ether, ester, urethane, urea, and carbonate ester functional group.

In some embodiments, in the monomer of formula (IV), Q is present and each Q-X is independently selected from the following group:

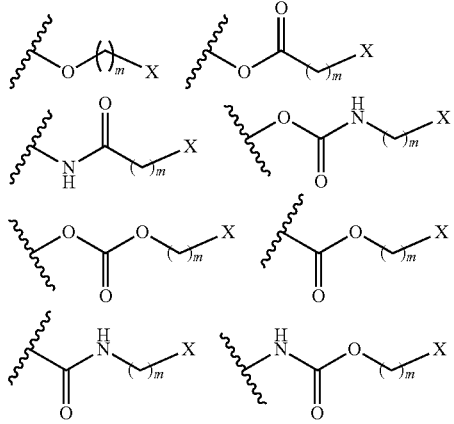

When a monomer-bioactive agent conjugate having a linking group Q is used to prepare polymer conjugates of the invention, the linking group Q becomes incorporated into the polymer backbone. Thus any linking moieties and functional groups present in Q become part of the backbone of the polymer conjugate.

When Q comprises a functional group (represented by Y in formulae defined herein) such as an amide, ether, ester, urethane, urea, and carbonate ester functional group, such functional groups will generally be cleavable functional groups and can provide points for erosion or degradation in the polymer backbone when a monomer-bioactive agent conjugate comprising such groups is used to form the polymer conjugate. The presence of cleavable groups derived from the functional groups in the polymer backbone can facilitate breakdown of the polymer conjugate, allowing formation of lower molecular weight polymer fragments.

The moiety "R" present in formulae (I), (Ib), (IIa), (IIb), (IIIa), (IIIb), (IV), (IVa), (IVb), (IVc), (VIa), (VIb), (VIc), (IXa) and (IXb) described herein represents an optionally substituted linear or branched hydrocarbon. In some embodiments the hydrocarbon may have between 1 and 12 carbon atoms, for example between 1 and 6 carbon atoms or 2 or 3 carbon atoms. The hydrocarbon may be partially or completely saturated or unsaturated (including moieties that are aromatic). Specific examples of R include a moiety having one of the following structures:

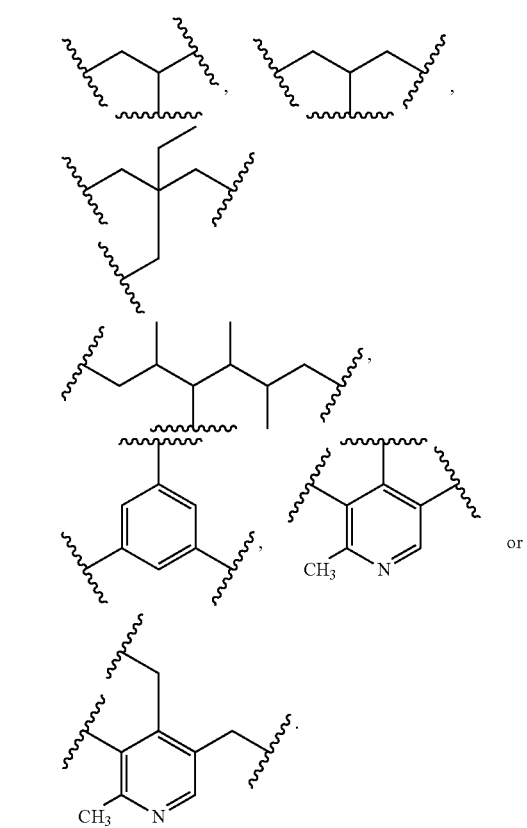

One skilled in the art would appreciate that when a monomer-bioactive agent conjugate comprising a moiety "R" is polymerised to form a polymer-bioactive agent conjugate, then R becomes part of the polymer backbone of the conjugate.

The moiety "Z" present in monomer-bioactive conjugates of formula (IV) represents a cleavable linking group as described herein.

The moiety "D" present in monomer-bioactive agent conjugates of formula (IV) represents a releasable bioactive agent as described herein. While the bioactive agent is releasable while conjugated to the monomer, it would be understood however that the bioactive agent is only intended to be released after the monomer-bioactive agent conjugate has reacted to form the polymer conjugate.

Examples of dialkynyl monomer conjugates with prostaglandin analogues as the pendant conjugated bioactive agent linked through the 1-carboxylic acid are shown below:

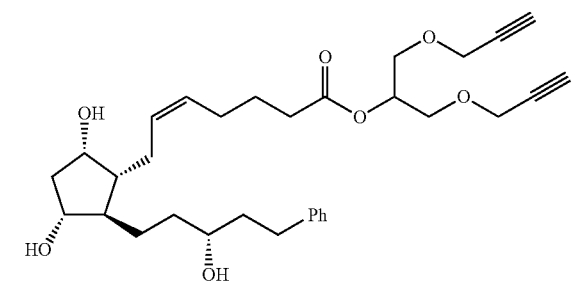

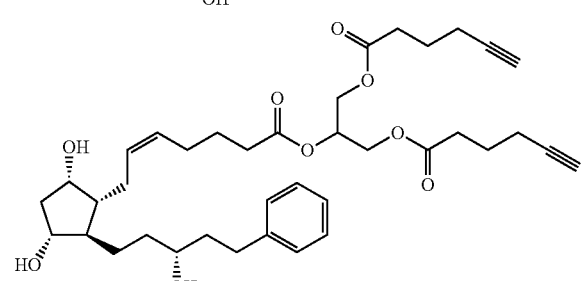

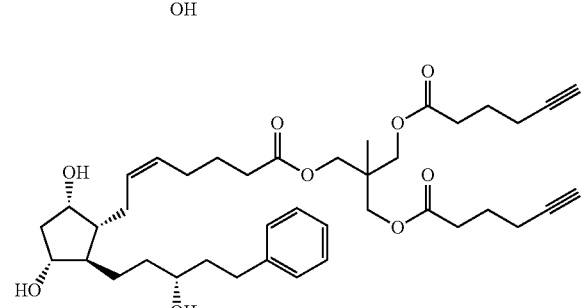

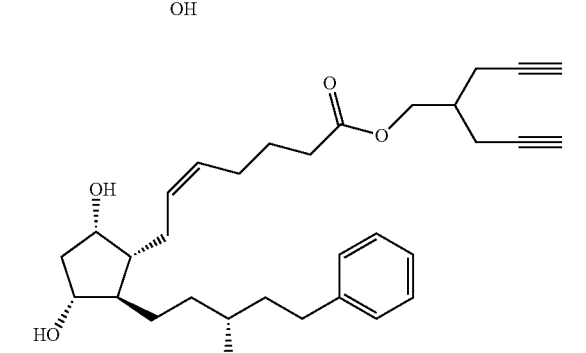

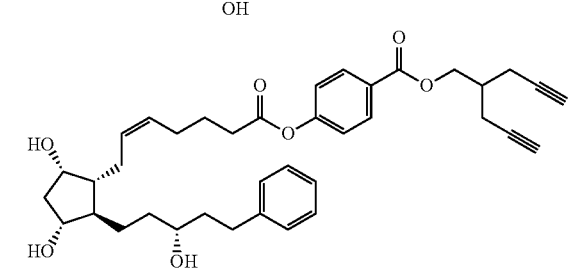

-continued

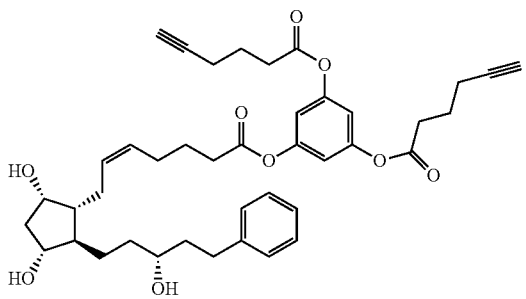

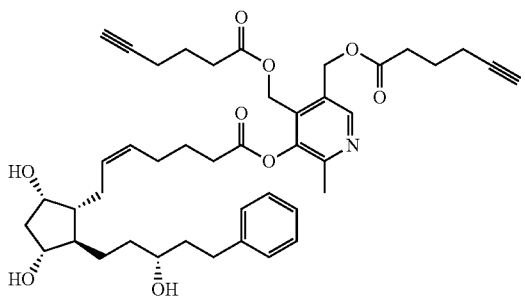

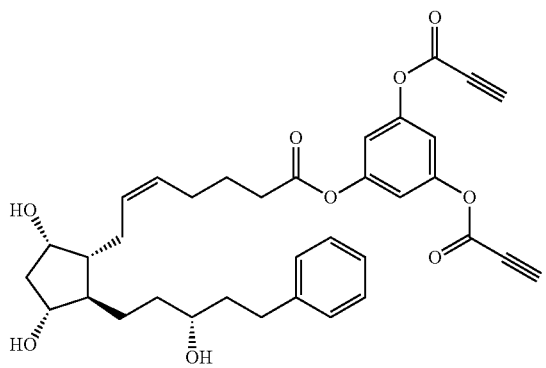

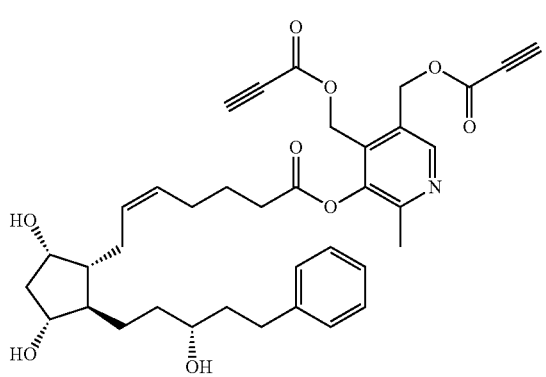

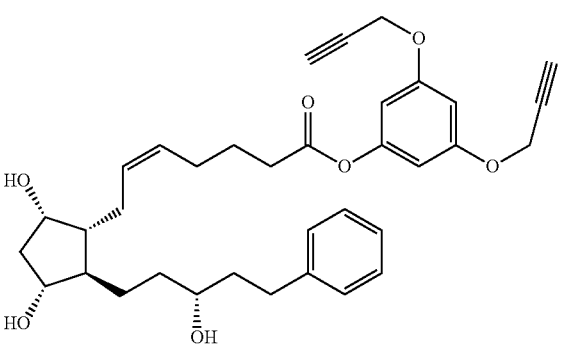

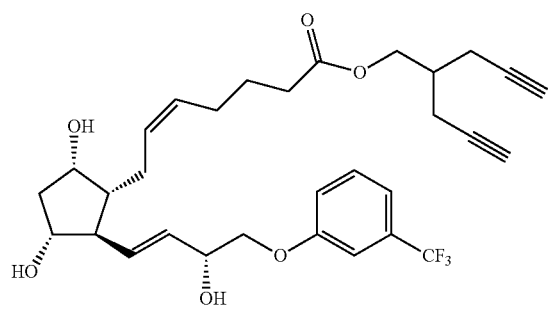
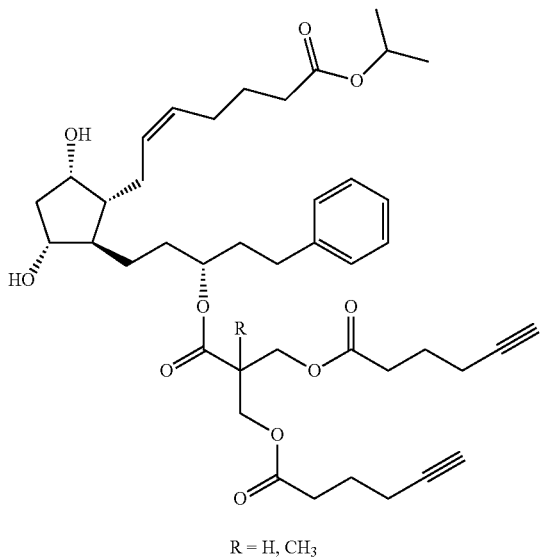
R = H, CH₃
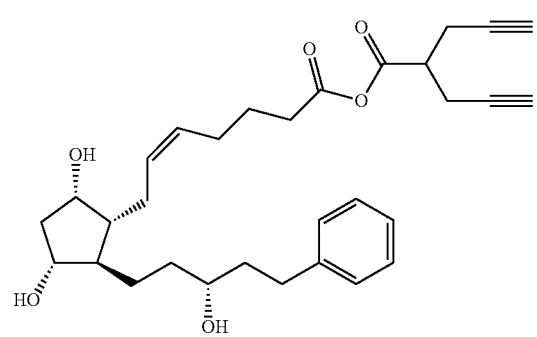
Examples of dialkynyl monomer conjugates with prostaglandin analogues as the pendant conjugated bioactive agent linked through the 15-hydroxy group are shown below:
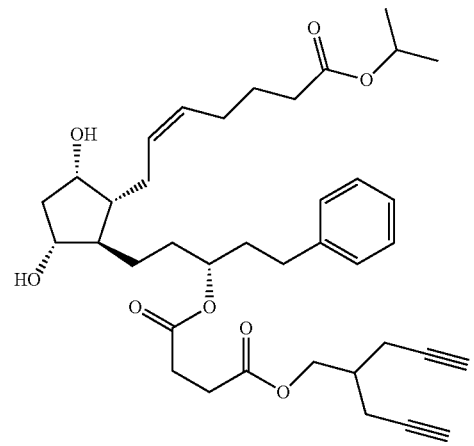
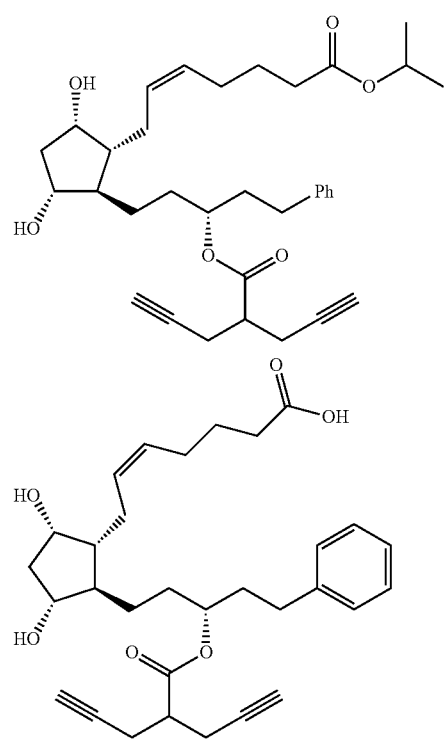
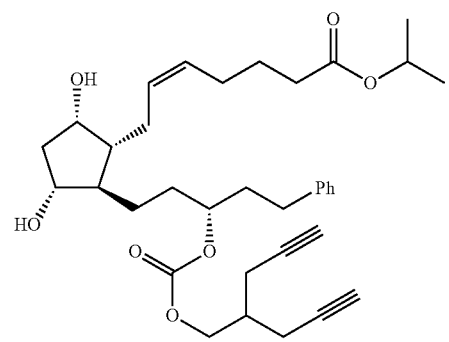

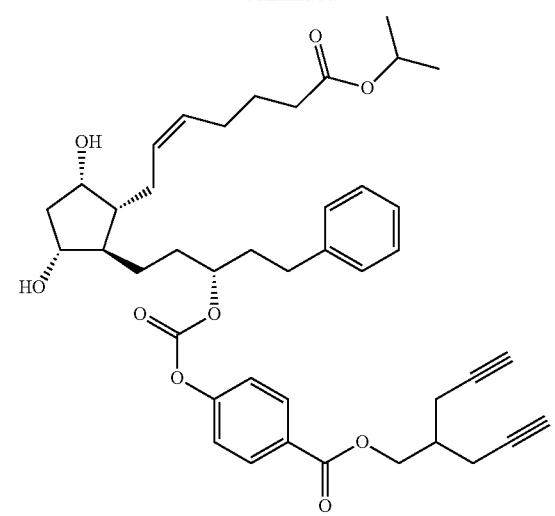
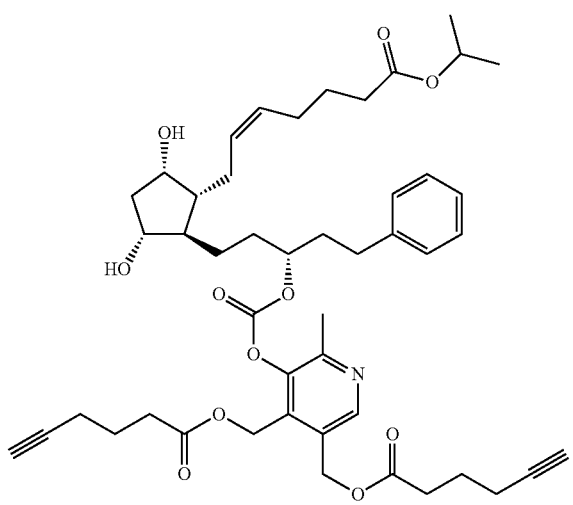
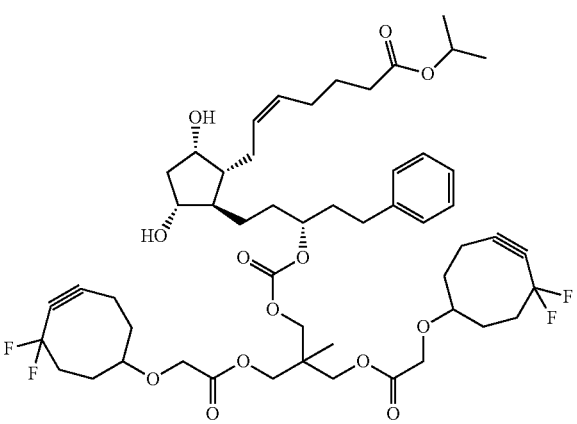
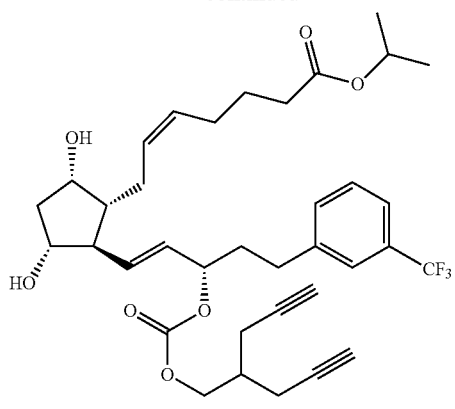
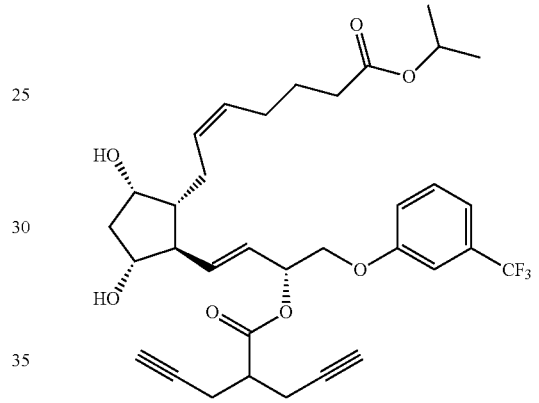
Examples of diazide monomer conjugates with prostaglandins as the pendant conjugated bioactive agent linked through the 1-carboxylic acid or the 15-OH group are shown below:
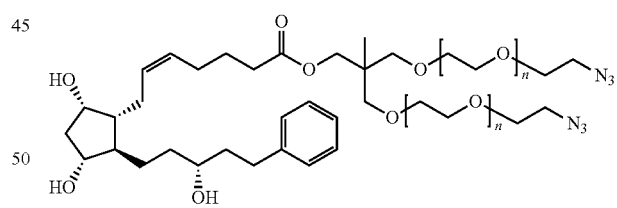
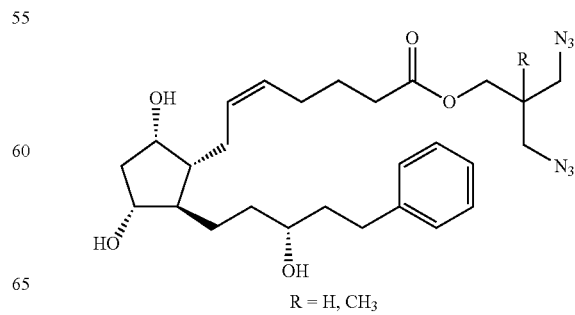
R = H, CH$_3$ 65
-continued
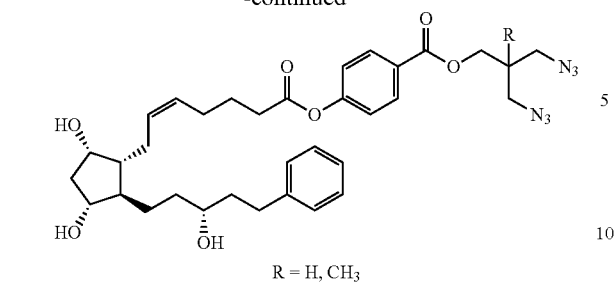
R = H, CH₃
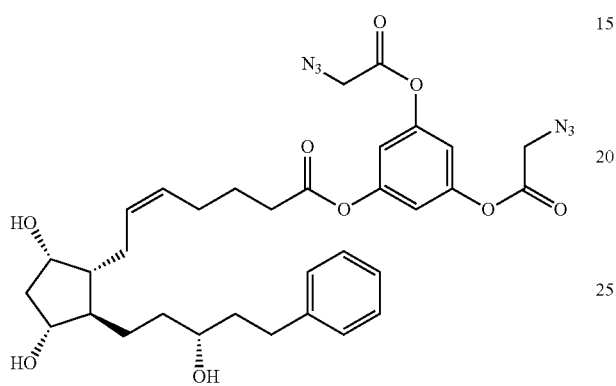
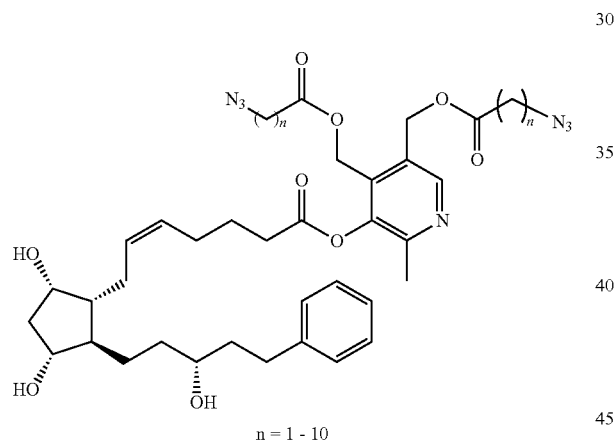
n = 1 - 10
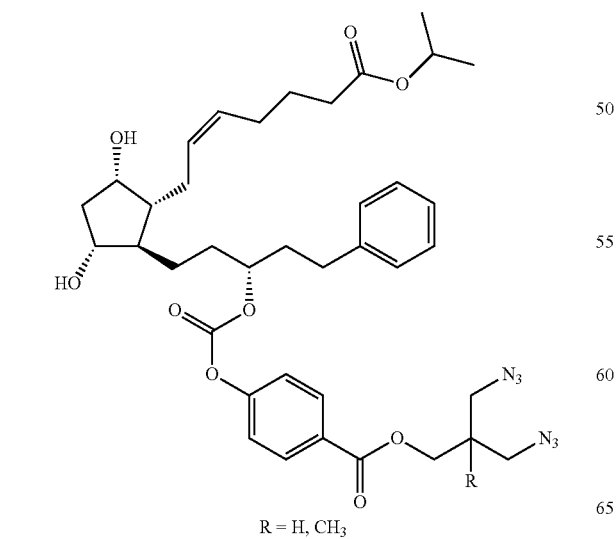
R = H, CH₃
66
-continued
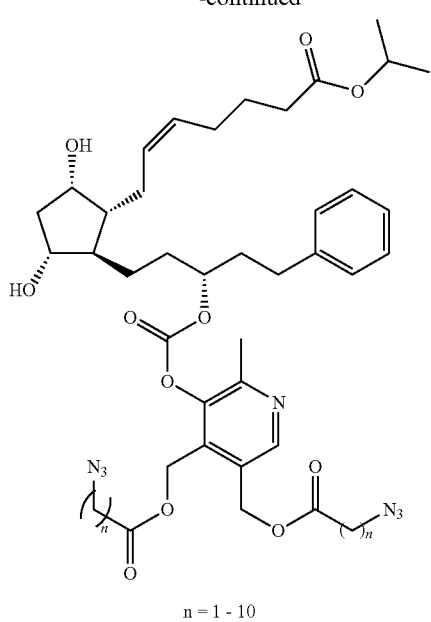
n = 1 - 10
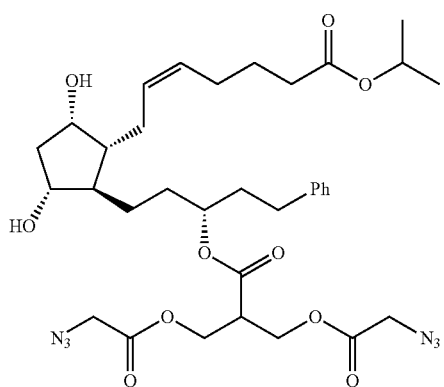
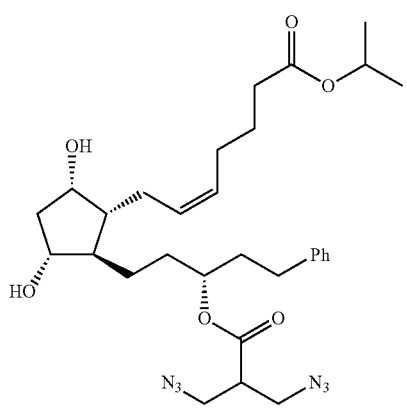

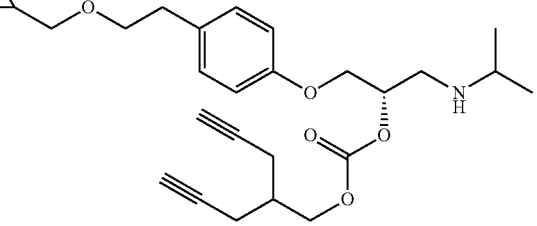
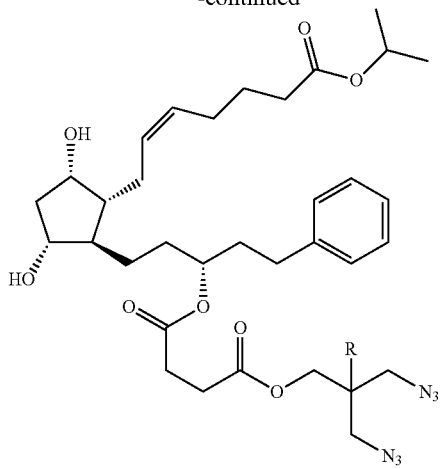
Examples of dialkyne, diazide and azide/alkyne monomer conjugates with β-blockers as the pendant conjugated bioactive agent linked through the hydroxy group are shown below:
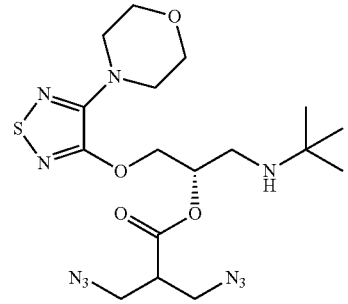
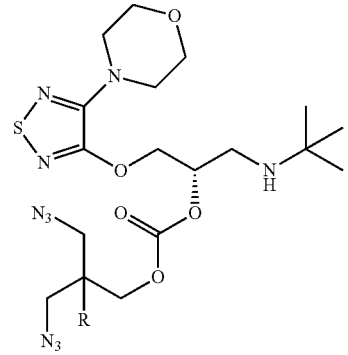
R = H, CH₃
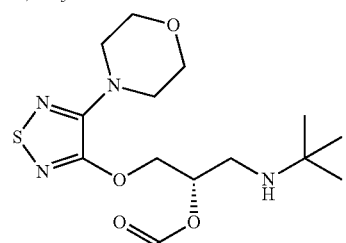
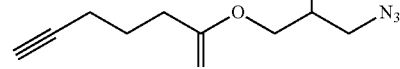
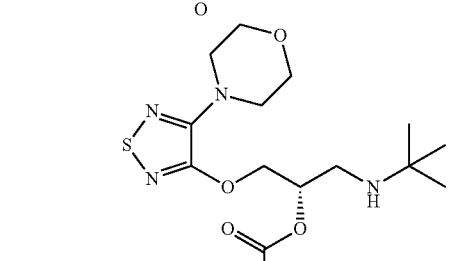
Monomer-bioactive agent conjugates of the invention may be prepared by covalently coupling a bioactive agent to a suitably functionalised alkyne or azide containing precursor compound. Some examples of alkyne precursor compounds that may be used to prepare monomer-bioactive agent conjugates of the invention are shown below:
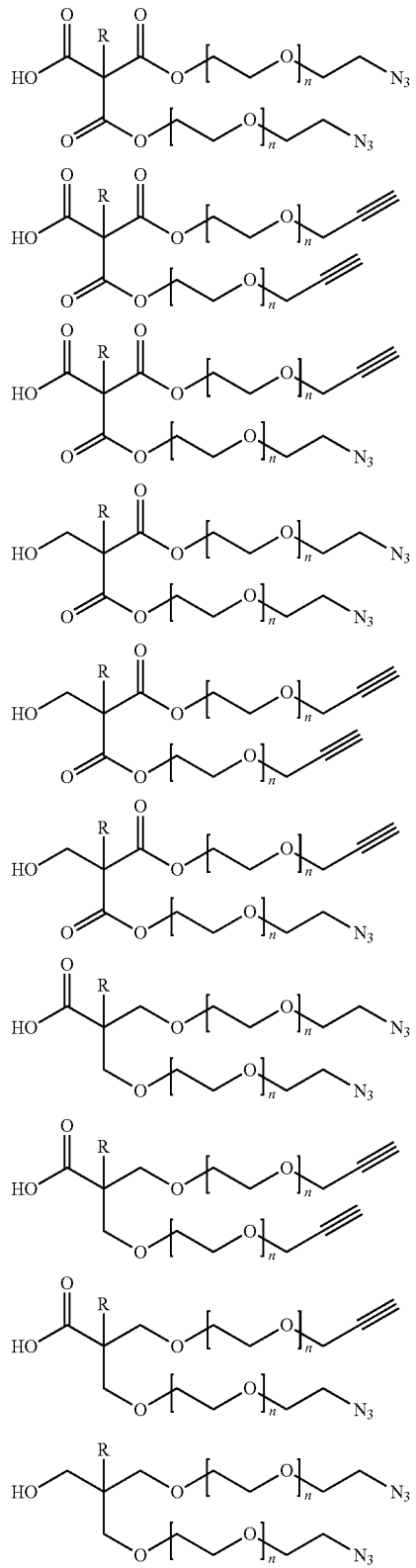
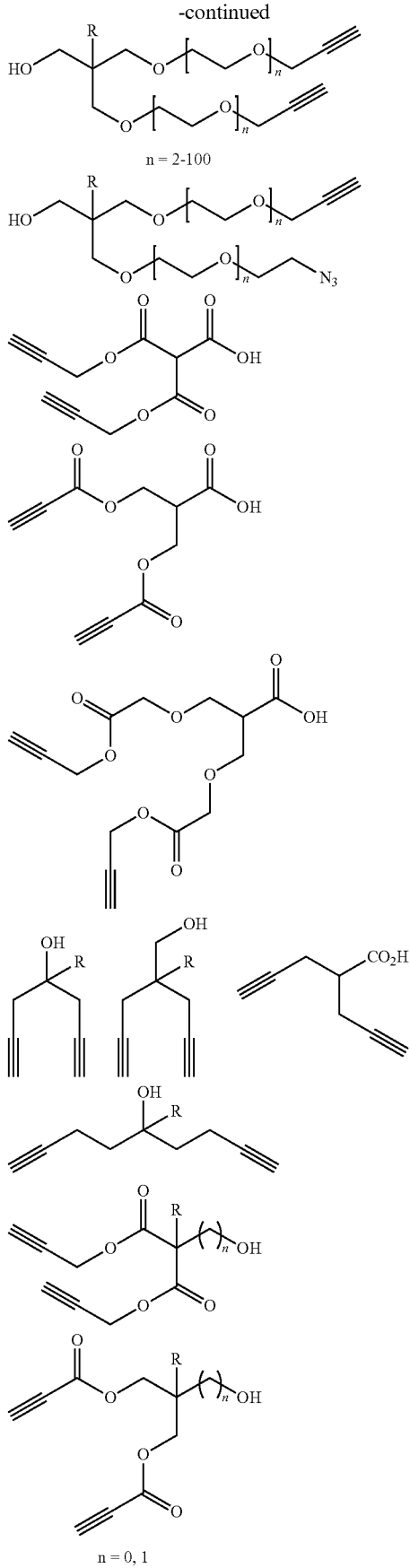

71

-continued

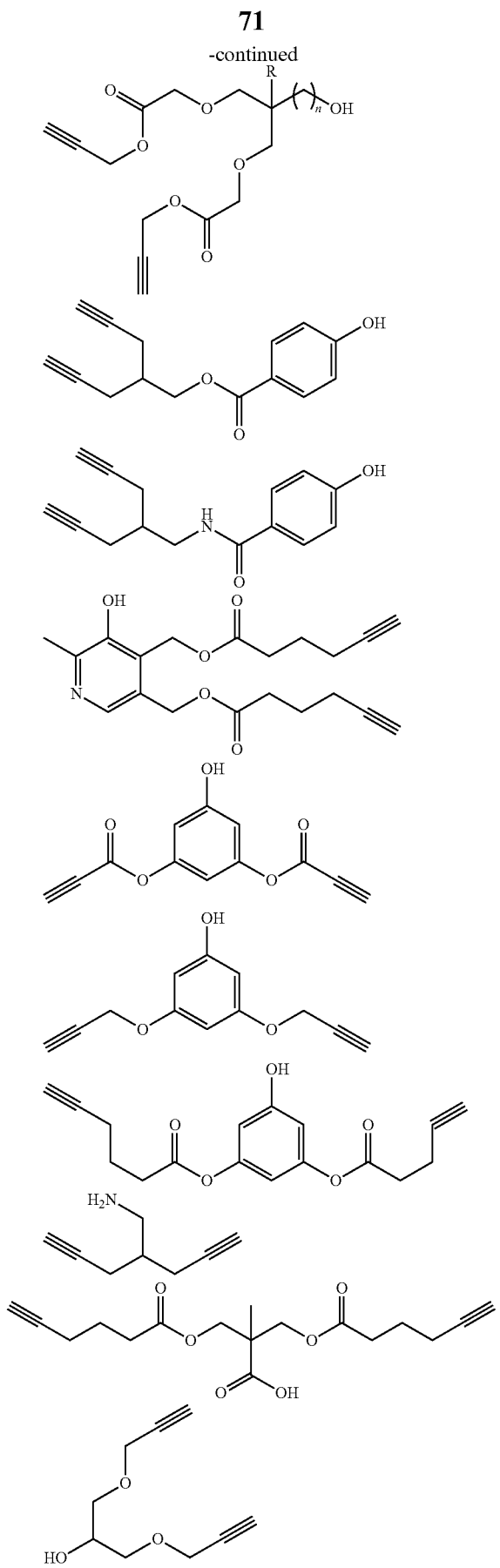

72

-continued

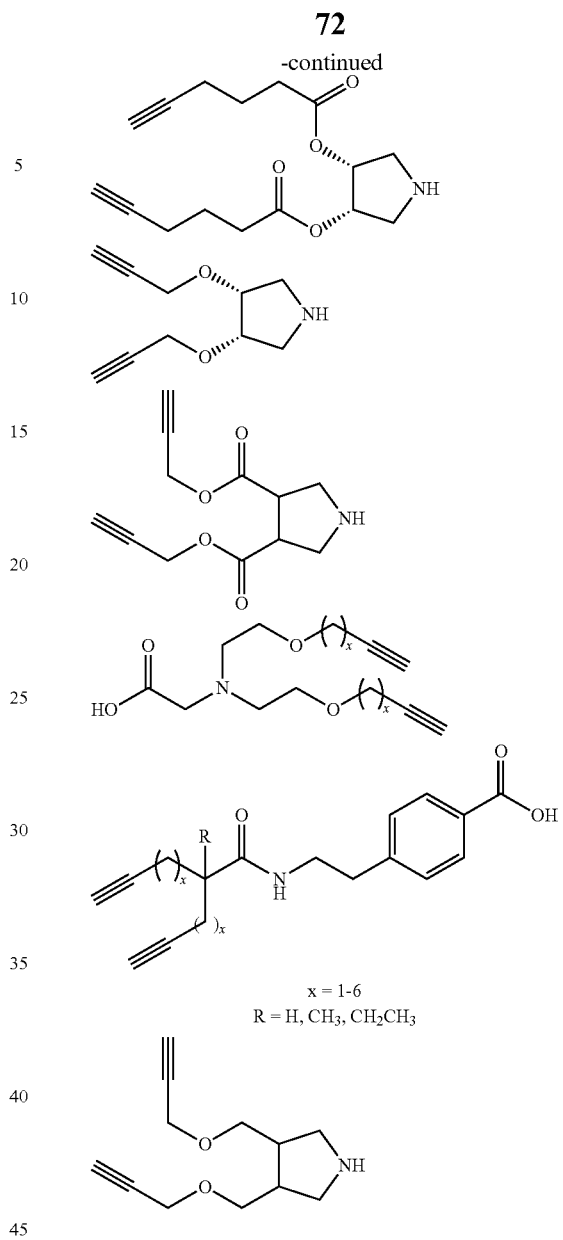

x = 1-6
R = H, CH$_3$, CH$_2$CH$_3$

In the above dialkyne compounds, the carboxylic acid or hydroxyl functional groups are capable of covalently reacting with a complementary functional group in a bioactive agent, to allow the bioactive agent to be coupled to the dialkyne compound to produce a monomer-bioactive agent conjugate that may participate in click chemistry reactions. One skilled in the relevant art would appreciate that one or more of the alkyne functionalities in the above compounds may be replaced by azide functional groups.

In one set of embodiments, the monomer-bioactive agent conjugate of formula (IV) is preferably a dialkyne monomer. Accordingly, the group X in formula (IV) are each terminal functional groups comprising alkyne functionality. Monomer-bioactive agent conjugates comprising terminal functional groups comprising alkyne functionality are preferred as such monomer-bioactive agents are safer to process than their diazide counterparts.

As discussed above, in some embodiments, the polymer-bioactive agent conjugate of the invention can be obtained by polymerising at least one monomer of formula (IV) with at least one monomer of formula (V) described above.

In some embodiments, the polymer-bioactive agent conjugate of the invention is a copolymer of at least one monomer of formula (IV):

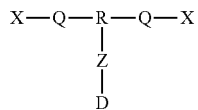

(IV)

where:

X may be the same or different at each occurrence and represents a terminal functional group comprising an alkyne or an azide functionality;

Q is independently selected at each occurrence and may be present or absent and when present, represents a linking group;

R is an optionally substituted linear or branched hydrocarbon which may include optionally substituted aromatic hydrocarbon and heteroaromatic hydrocarbon;

Z is a cleavable linking group; and

D is a bioactive agent selected from the group consisting of prostaglandin analogues and β-blockers;

and at least one monomer of formula (V):

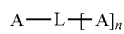

(V)

where:

A may be the same or different at each occurrence and represents a group comprising a terminal functional group comprising an alkyne or an azide functionality, wherein said terminal functional group is complementary to the terminal functional group of X;

L is an optionally substituted linker group; and n is an integer and is at least 1.

The groups A, L and n in formula (V) are further discussed below.

The covalent reaction between a terminal functional group (X) on the monomer of formula (IV) with a complementary terminal functional group on the monomer of formula (V) produces a triazole moiety. Triazole moiety may be of formulae (II), (III) or (IX) as described herein. Preferably, the triazole moiety is a 1,4-regioisomer as represented by formulae (II), (IIa) and (IIb), or a 1,5-regiosiomer as represented by formulae (III), (IIIa) and (IIIb), as described herein. It will be understood by those skilled in the art that the 1,4-regioisomer can be formed using a copper catalyst during the reaction of the monomers and the 1,5-regioisomer can be formed using a rhuthenium catalyst during the reaction of the monomers (J. Am. Chem. Soc., 2005, 127 (46), pp 15998-15999, Ruthenium-Catalyzed Cycloaddition of Alkynes and Organic Azides, Zhang et al, Boren et al J Am Chem Soc 2008; 130: 8923-8930).

The triazole may also be formed through the use of metal-free, strain promoted azide-alkyne cycloaddition (SPAAC) and does not require a catalyst. The regiochemistry of SPAAC is mixed with both 1,4 and 1,5 1,2,3 triazoles being formed. The preparation of cycloalkyne and heterocyclic alkyne compounds and their use in SPAAC click chemistry has been described in a number of publications, including:

Jewett et al. "Cu-free click cycloaddition in chemical biology", Chem. Soc. Rev., 2010, 39, 1272-1279;

Baskin et al. "Copper-Free Click Chemistry: Bioorthogonal Reagents for Tagging Azides" Aldrichimica Acta, Vol. 43, No. 1 2010, 15-23;

Recer et al. "Click Chemistry beyond Metal-Catalyzed Cycloaddition" Angew.Chem. Int. Ed., 2009, 48, 4900-4908.

Almeida et al. "Thiacycloalkanes for copper-free click chemistry", Angewandte Chemie Int. Ed. 2012, 51, 2443-2447; and Sletten et al., "Ahydrophilic Azacyclooctyne for Cu-Free Click Chemistry Org. Let. Vol. 10, No. 14, 2009, 3097-3099.

The methods and compounds described in these references may be used in preparation of the cycloalkyne of formula XVI having a wide range of substituents without undue experimentation. The method of the invention may be used to provide a wide range of polymers of formula IX with triazole units such as in formula IV. It is an advantage of this embodiment that the copolymerization reaction to form triazole groups may in many cases take place without the need for a catalyst.

The monomers of formula (IV) and (V) may react with one another in a mole ratio of 1:1. In some embodiments, it may be desirable to have a molar excess of a monomer comprising terminal functional groups having alkynyl functionality. Without wishing to be limited by theory, it is thought that azide containing functional groups may be toxic to a biological environment. As a result, the use of a molar excess of monomer comprising alkynyl functional groups to prepare the conjugates may help to ensure that residual unreacted azide functional groups do not remain in the structure of the conjugates.

In the monomer of formula (V), A represents a group comprising a terminal functional group comprising an alkyne or an azide functionality. The azide or alkyne functionality present in terminal functional group of moiety "A" is complementary to the azide or alkyne functionality present in the terminal functional group of X in formula (IV), such that upon reaction of the functional groups in A and X under click reaction conditions, a triazole moiety is formed.

In the monomer of formula (V) n is an integer and is at least 1. In some embodiments, n is an integer selected from the group consisting of 1, 2, 3, 4, 5, 6, 7 and 8. In one form, in the monomer of formula (V) n is 1 or 2. The monomer of formula (V) comprises at least two A moieties, which may be the same or different at each occurrence.

When n is 1, the monomer of formula (V) is difunctional and comprises two A moieties. When n is 2 or more, the monomer of formula (V) is multifunctional and comprises 3 or more A moieties. In such embodiments, the monomer of formula (V) may be a branched monomer. Three or more A moieties may be present when L is branched. Monomers of formula (V) comprising at least three terminal functional groups have the potential to provide branched architectures for the polymer conjugates of the invention.

As used herein, the term "group comprising a terminal functional group" encompasses embodiments where the group represents the terminal functional group per se, as well as embodiments where the terminal functional group is part of a larger chemical group.

The moiety "L" in formula (V) represents an optionally substituted linker group. In some embodiments L may be a divalent group. Alternatively, L may be multivalent and be a branched group. When a monomer of formula (IV) and (V) copolymerise, L forms a linker segment in the polymer backbone of the conjugate.

In some embodiments, L may comprise a linker moiety selected from the group consisting of optionally substituted linear or branched aliphatic hydrocarbon, optionally substituted carbocyclyl, optionally substituted heterocyclyl, optionally substituted aryl, optionally substituted heteroaryl, an optionally substituted polymeric segment, and combinations thereof.

Optionally substituted linear or branched aliphatic hydrocarbon linker moieties may be selected from optionally substituted $C_1$ to $C_{20}$, $C_1$ to $C_{10}$ or $C_1$ to $C_6$ linear or branched aliphatic hydrocarbons. The aliphatic hydrocarbons may be saturated or unsaturated hydrocarbon.

Optionally substituted carbocyclyl linker moieties may have from 3 to 12, 3 to 8 or 5 to 6 carbon ring members.

Optionally substituted heterocyclyl linker moieties may have from 3 to 12, 3 to 8 or 5 to 6 ring members and 1, 2, 3, 4 or more heteroatoms as a part of the ring. The heteroatoms may be independently selected from the group consisting of O, N and S.

Optionally substituted aryl linker moieties may have from 3 to 12, 3 to 8 or 5 to 6 carbon ring members and at least one unsaturation.

Optionally substituted heteroaryl linker moieties may have from 3 to 12, 3 to 8 or 5 to 6 ring members and 1, 2, 3, 4 or more heteroatoms as a part of the ring. The heteroatoms may be independently selected from the group consisting of O, N and S. The heteroaryl linker moiety also has at least one unsaturation.

Optionally substituted polymeric linker moieties may comprise any suitable polymer or copolymer. In some embodiments, it can be desirable for the polymeric moiety to comprise a biocompatible and/or biodegradable polymer. One skilled in the relevant art would be able to select suitable biocompatible and/or biodegradable polymers. Exemplary biocompatible polymers may include polyethers, polyesters, polyamides, polyurethanes, and copolymers thereof, such as poly(ether-esters), poly(urethane-ethers), poly(urethane-esters), poly(ester-amides) and the like. Preferred biocompatible polymers are polyethers, polyesters, polyurethanes, and copolymers thereof.

Exemplary polyethers include polymers of $C_2$ to C4 alkylene diols, such as polyethylene glycol and polypropylene glycol, preferably polyethylene glycol.

Exemplary polyesters include polycaprolactone, poly(lactic acid), poly(glycolic acid) and poly(lactic-co-glycolic acid).

In one form, the polymeric linker moiety may comprise a biodegradable polymer. In general, biodegradable polymers comprise at least one biodegradable moiety. The biodegradable moiety may be selected from the group consisting of an ester, an amide, a urethane and a disulfide moiety. The biodegradable polymers comprise a combination of such moieties. One skilled in the relevant art would understand that such biodegradable moieties are capable of undergoing degradation or cleavage in a biological or physiological environment.

Optionally substituted polymeric linker moieties may be of any suitable molecular weight, and the desired molecular weight may depend on the type of polymer and its properties. In some embodiments, L comprises a polymeric moiety having a molecular weight of not more than 1500.

In one set of embodiments, L comprises a polyether linker moiety derived from polyethylene glycol (PEG). The polyether segment may be derived from a PEG of suitable molecular weight. In some embodiments, the PEG has a molecular weight in the range of from about 200 to 10,000, preferably from about 200 to about 3000.

In one set of embodiments, L comprises a linker moiety derived from lysine, including the ethyl ester of lysine such as ethyl-2,6-bis(((3-azidopropoxy)carbonyl)amino)hexanoate (ELDN$_3$) the di(1-pentynol)urethane of the ethyl ester of lysine and the di(1-pentynol)urethane of the 1-pentynol ester of lysine.

In some embodiments, the group "L" in the formula (V) may comprise a functional group. The functional group may be selected from the group consisting of an amide, ether, ester, urethane, urea, and carbonate ester functional group. Such functional groups will generally be cleavable functional groups, which can degrade in a biological environment.

In one set of embodiments, L comprises a linker moiety and a functional group.

In some embodiments, the monomer of formula (V) may have a structure of formula (Va):

where:

A may be the same or different at each occurrence and represents a group comprising a terminal functional group comprising an alkyne or an azide functionality, wherein the alkyne or azide functionality in the terminal functional group is complementary to the alkyne or azide functionality in a terminal functional group X present on a monomer of formula (IV);

Y represents a functional group;

B may be present or absent and when present represents an optionally substituted linker moiety; and n is 1 or 2.

In some embodiments, the monomer of formula (V) may have a structure of formula (Vb):

where:

A may be the same or different at each occurrence and represents a group comprising a terminal functional group comprising an alkyne or an azide functionality, wherein the alkyne or azide functionality in the terminal functional group is complementary to the alkyne or azide functionality in a terminal functional group X present on a monomer of formula (IV);

Y may be the same or different at each occurrence and represents a functional group;

B represents an optionally substituted linker moiety; and n is at least 1, preferably n is 1 or 2.

In some embodiments of formula (Vb), B represents a branched linker moiety (such as branched aliphatic linker moiety) and n is at least 2. In such embodiments, B comprises three or more -Y-A substituent groups.

In some embodiments of formula (Vb), B represents a branched linker moiety (such as branched aliphatic linker moiety) and n is 2. In such embodiments, B comprises three -Y-A substituent groups In some embodiments of formula (Vb), B represents an optionally substituted polymeric linker moiety. The polymeric linker moiety may comprise a biocompatible and/or biodegradable polymer as described herein. In one set of embodiments B preferably comprises a polyether, polyester, polyamide, polyurethane, or copolymer thereof.

In one set of embodiments of formulae (Vb), B is a polymeric linker moiety derived from polyethylene glycol (PEG). The polyethylene glycol moiety preferably has a molecular weight in the range of from about 200 to 10,000, more preferably from about 200 to 3000.

The group Y in formulae (Va) and (Vb) may be independently selected from the group consisting of an amide, ether, ester, urethane, urea, and carbonate ester functional group, preferably a ester or urethane functional group.

In monomers of formulae (Va) and (Vb), the combination of the moieties B and Y together form the linker group L, as shown in formula (V).

Some specific examples of monomers of formula (V) that may be used to prepare polymer-bioactive agent conjugates of the invention is shown in Table 3:

TABLE 3

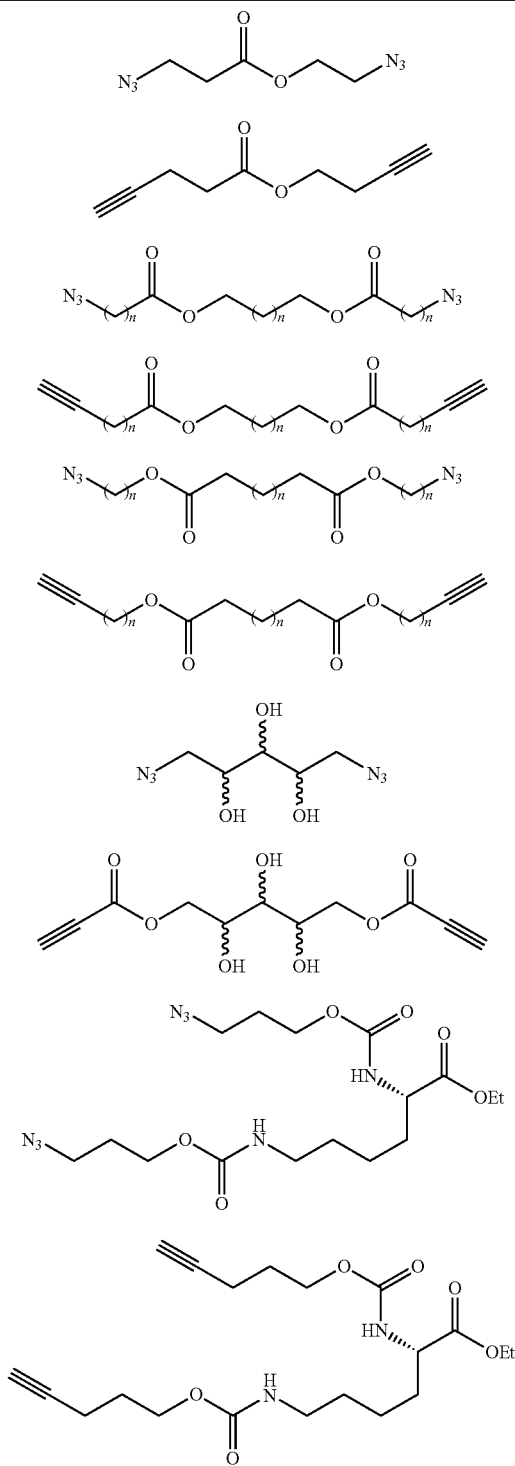

TABLE 3-continued
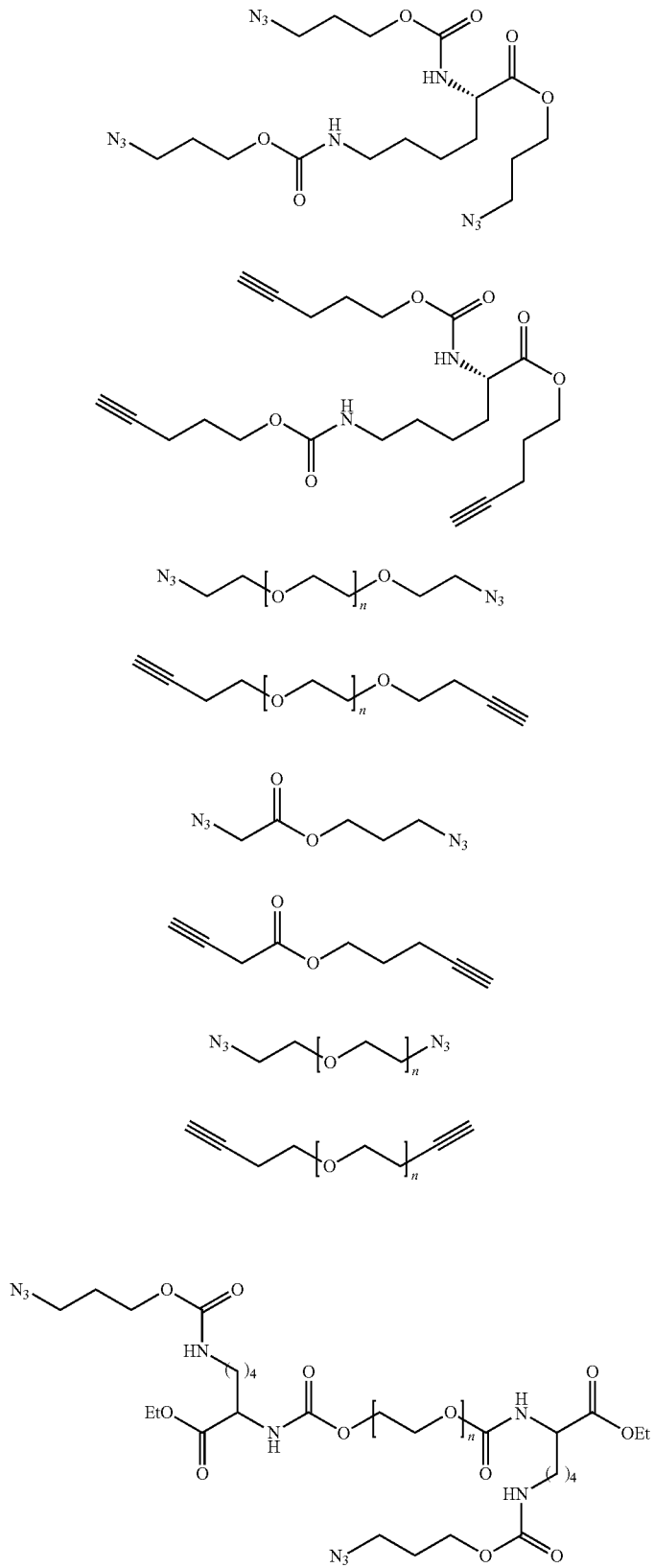

TABLE 3-continued
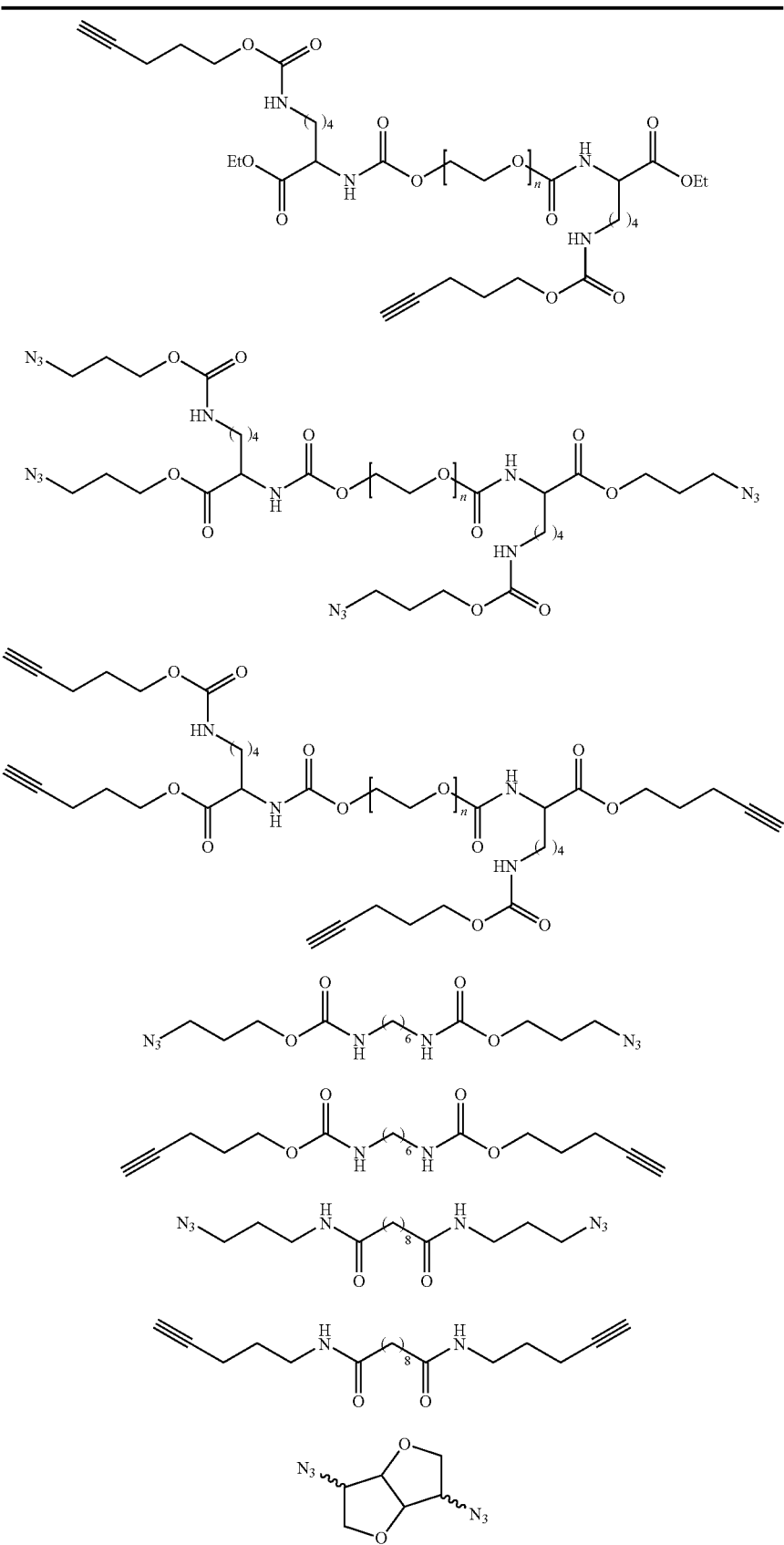

TABLE 3-continued

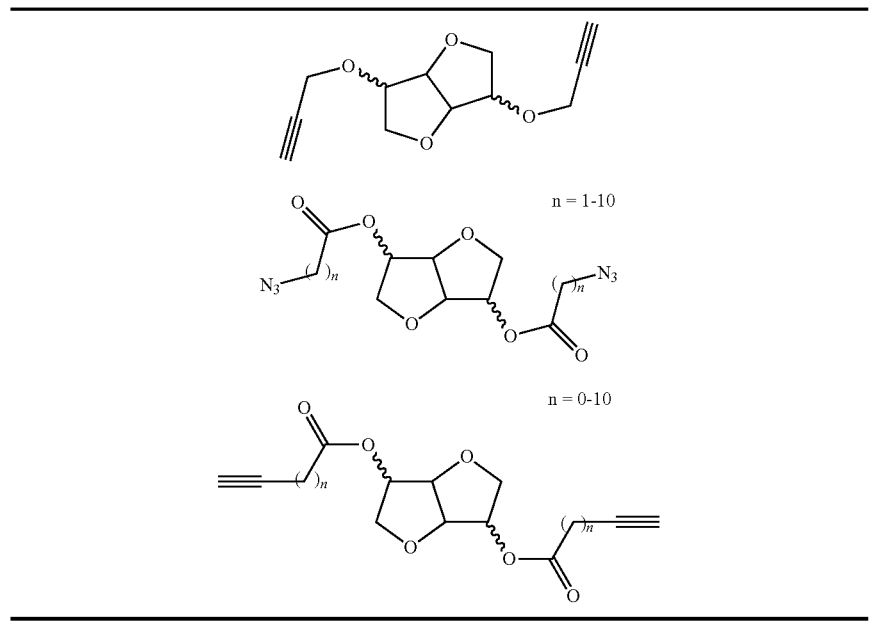

n = 1-10 n = 0-10

In some structures shown in Table 3, n represents the number of repeating units and is an integer that may be selected from 0 and at least 1.

An example of a polymer-bioactive agent conjugate of the invention formed with a dialkyne monomer of formula (IV) and a diazide monomer of formula (V) is shown in Scheme 1 below:

Scheme 1

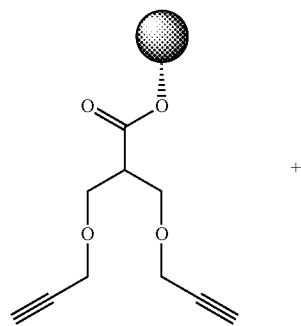

+

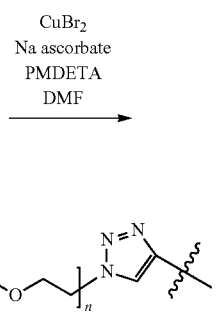

-continued

Another example of a polymer-bioactive agent conjugate of the invention formed with a dialkyne monomer of formula (IV) and a diazide monomer of formula (V) is shown in Scheme 2 below:

Scheme 2

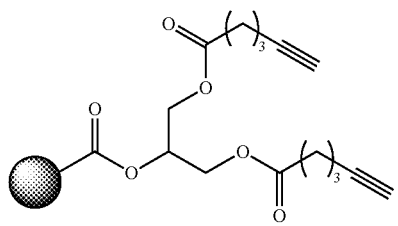

+

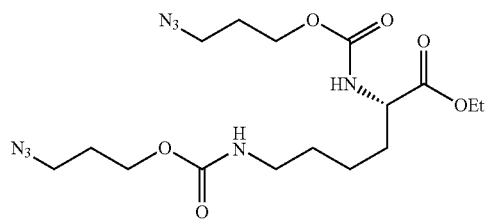

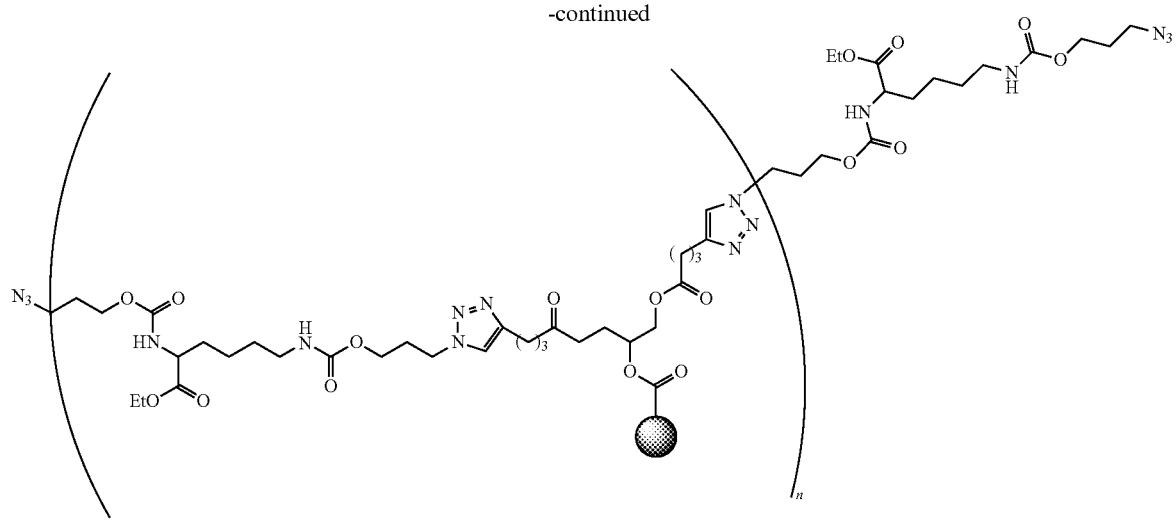

An example of a polymer-bioactive agent conjugate of the invention formed with a diazide monomer formula (IV) and a dialkyne monomer of formula (V) is shown in Scheme 3 below:

Scheme 3

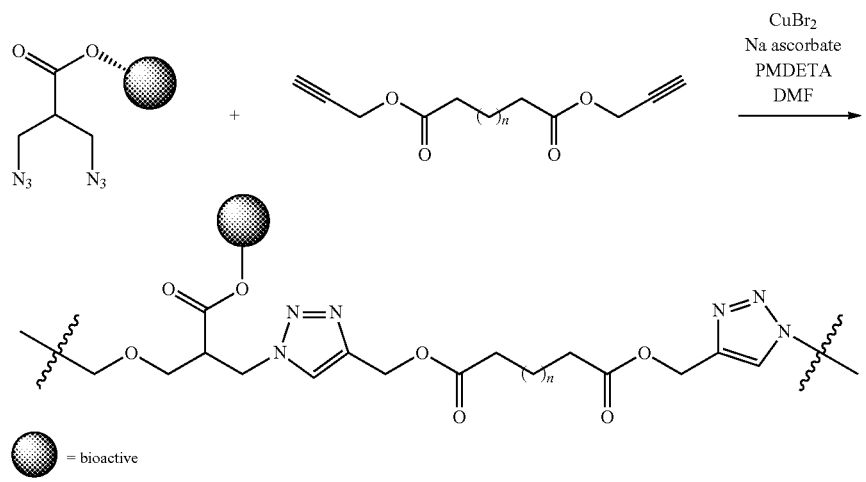

Scheme 4 illustrating general structures of polymer-bioactive agent conjugates in accordance with embodiments of the invention that are formed with co-monomers comprising different terminal functional groups and under different click chemistry reaction conditions.

Scheme 4

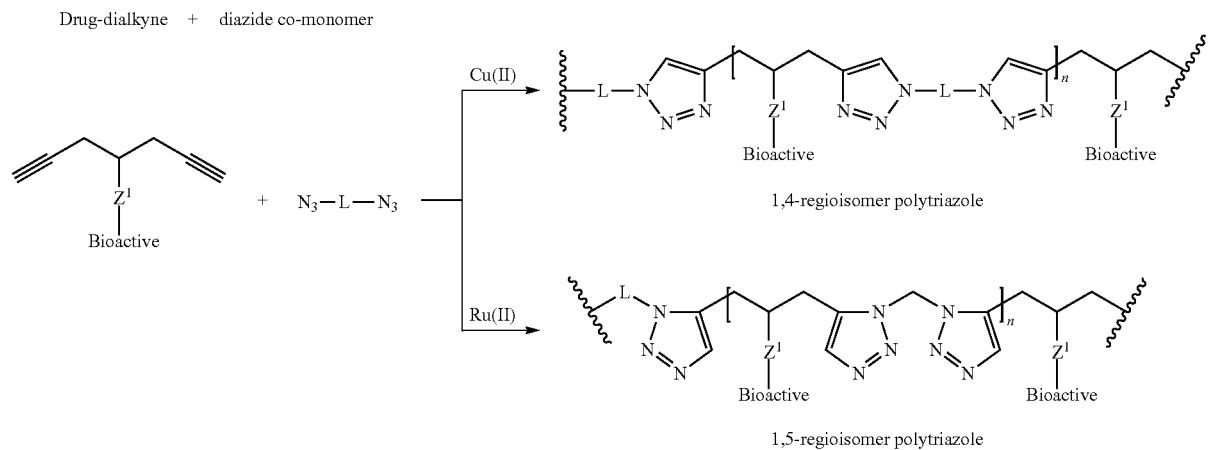

Drug-diazide + dialkyne co-monomer

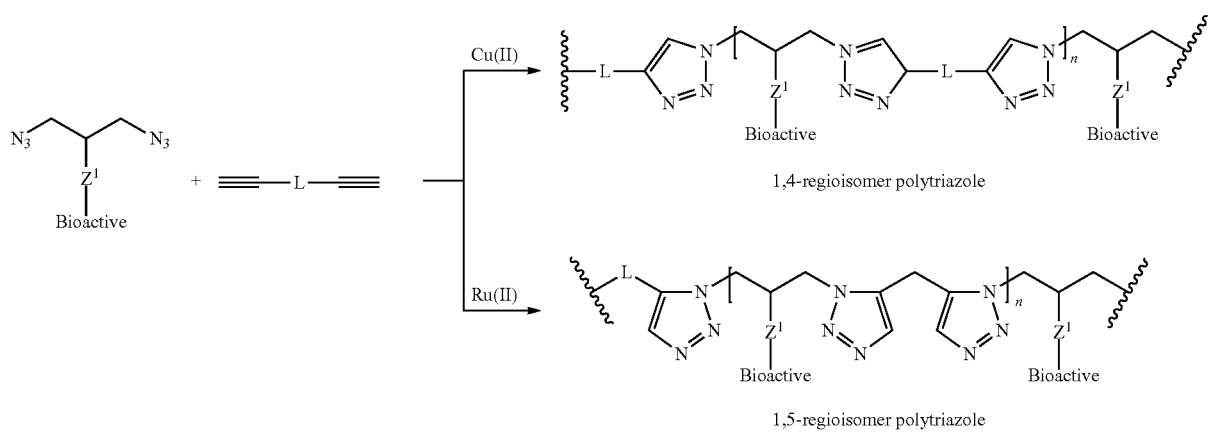

1,4-regioisomer polytriazole 1,5-regioisomer polytriazole

Drug-bifunctional alkyne/azide
+
bifunctional alkyne/azide co-monomer

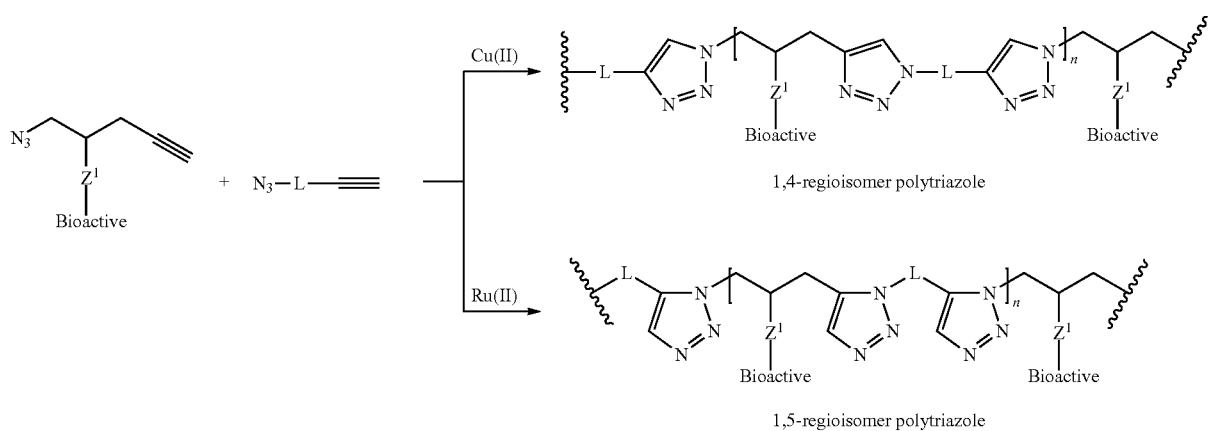

1,4-regioisomer polytriazole 1,5-regioisomer polytriazole

One skilled in the relevant art would understand that the constituent components of each monomer, for example the cleavable linking group of the monomer of formula (IV) or the linker group of the monomer of formula (V), can be varied to allow the properties of the polymer-bioactive agent conjugate to be tailored to suit particular applications.

Polymer conjugates of the invention may contain more than one type of bioactive agent.

Polymer conjugates of the invention may contain more than one type of linker segment in the polymer backbone.

Some specific examples of monomer-bioactive agent conjugates, and co-monomers that may be used in the preparation of polymer-bioactive agent conjugates of the invention are shown below:

Monomer-bioactive agent conjugates

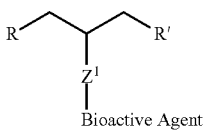

R = R' = interchangeably a group including an aklyne or azide

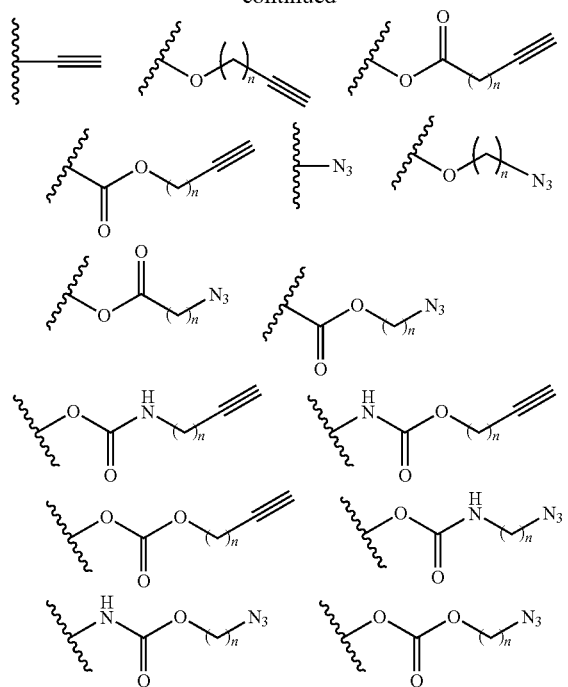

Co-monomers

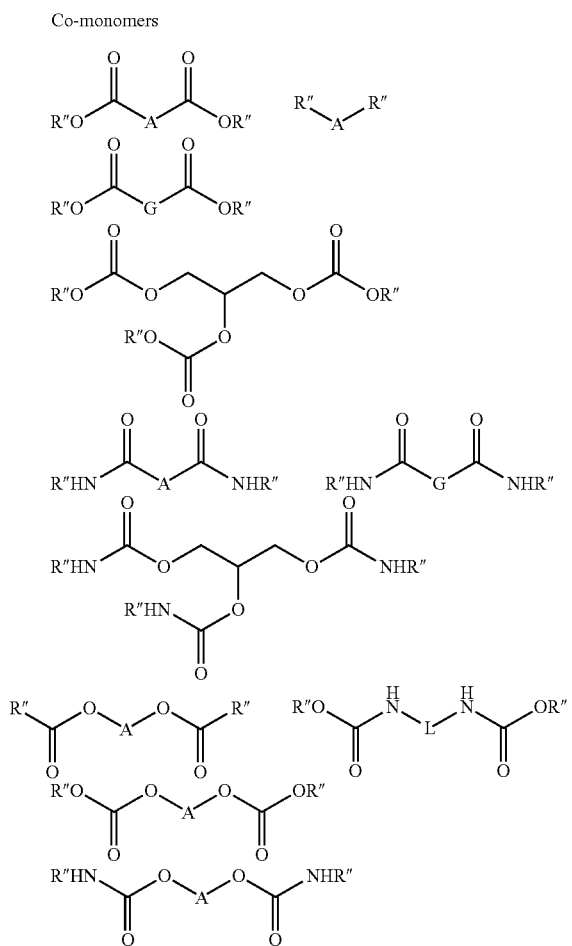

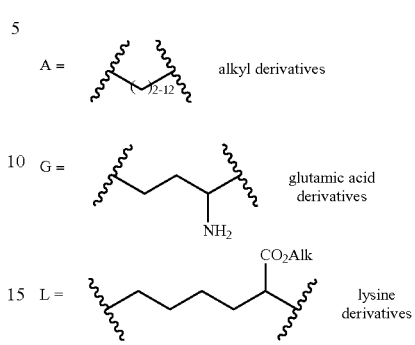

As discussed above, polymer-bioactive agent conjugates of the invention may comprise a moiety of formulae (VIa), (VIb) or (VIc). Moieties of formulae (VIa), (VIb) and (VIc) may be formed when a monomer of formula (IV) polymerises with a monomer of complementary functionality. The monomer of complementary functionality may be a monomer of formula (V), or it may be a further monomer of formula (IV). As illustrated above, moieties of formulae (VIa), (VIb) and (VIc) comprise Q and in the case of formulae (VIa) and (VIb), also comprise L.

Polymer-bioactive agent conjugates of the invention may be a copolymer of a mixture of monomers, such as for example, a mixture of two or more monomer conjugates of formula (IV), optionally, or additionally, with a mixture of two or more complementary monomers of formula (V). The ability to use a monomer composition comprising a mixture of different types of monomer can allow the properties of the polymer conjugates to be tailored for different applications. For example, the copolymerisation of at least two different monomer conjugates of formula (IV), where the monomer conjugates comprise prostaglandin analogues and β-blockers as the bioactive agent D, can allow a single polymer conjugate comprising a mixture of prostaglandin analogues and β-blockers as pendant bioactive agents to be obtained.

When Q and L comprise functional groups, conjugates of the invention may comprise a polymer backbone having a plurality of cleavable functional groups. The cleavable functional groups will generally form part of the polymer backbone and may be located on either one side or both sides of a triazole moiety. Cleavage of the functional groups in the polymer backbone may therefore release a triazole containing fragment when polymer conjugates of the invention biodegrade. For example, when Q and/or L comprises ester functional groups, a triazole fragment produced as a by-product of polymer degradation could be a dihydroxy triazole, a diacid triazole or hydroxyl-acid triazole, depending on the direction of the ester.

The invention also provides a method for preparing a polymer-bioactive agent conjugate comprising as part of its polymer backbone a moiety of general formula (I):

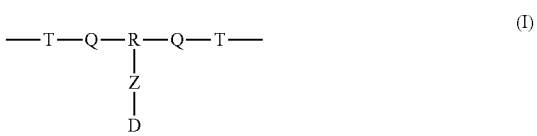

by reacting at least one monomer of formula (IV):

with at least one complementary monomer of formula (V):

under click cycloaddition reaction conditions.

In embodiments of the invention, click cycloaddition reactions may be catalyzed by a metal. Exemplary metals include copper (e.g. Cu(I)) which may be generated in situ from Cu(II) and ascorbic acid), and ruthenium (e.g. Ru(II)). Other metals that can be used include, but are not limited to, Ag, Ni, Pt, Pd, Rh, and Ir. In addition a metal free, strain promoted azide-alkyne cycloaddition (SPAAC). In this embodiment, no metal catalyst is required as the alkyne is activated by means of incorporation of the alkyne functionality into a strained ring.

In some embodiments, one or more further monomers may be employed in the synthesis of the polymer-bioactive conjugates of the invention. When used, the one or more further monomers may act as chain extenders, to increase the molecular weight or to tailor the properties of the polymer backbone, for example, by introducing flexibility or hard or soft segments into the polymer backbone. In order to be incorporated into the polymer backbone, the one or more further monomers will be required to have terminal functional groups selected from alkyne and azide functional groups. Depending on the nature of the terminal functional group, the one or more further monomers will be capable of reacting with at least one co-monomer selected from the group consisting of a formula (IV) and a monomer of formula (V).

It is possible to some extent to control the molecular weight of the polymer-bioactive agent conjugate, its degree of branching (through control of monomer functionality) and its end group functionality by adjusting the molar ratio and the functionality of the monomers employed in the conjugate synthesis.

Irrespective of the manner in which the polymer-bioactive agent conjugates are prepared, all repeat units that make up the polymer backbone will be coupled via a triazole moiety.

In one embodiment, the methods of the invention allow the formation of biodegradable moieties with multiple bioactive agents, known loadings, evenly distributed bioactive agents in the polymer chain, predetermined relative proportions and predetermined relative positions.

Polymer-bioactive agent conjugates in accordance with the invention can advantageously be prepared such that they are suitable for administration to a subject (i.e. suitable for in vivo applications).

According to one embodiment there is provided a method of delivering a bioactive agent to a subject, the method comprising administering to the subject a polymer-bioactive agent conjugate in accordance with the invention.

By the polymer conjugate being "suitable" for administration to a subject is meant that administration of the conjugate to a subject will not result in unacceptable toxicity, including allergenic responses and disease states. By the term "subject" is meant either an animal or human subject.

By "administration" of the conjugate to a subject is meant that the composition is transferred to the subject such that the bioactive agent will be released. The prostaglandin analogues and β-blockers are intended to use in the treatment of eye disorders associated with increased intraocular pressure, such as glaucoma, it is preferred that the polymer conjugate is administered to an affected eye of a subject. Administration to the eye may be by way of intracameral or subconjunctival administration.

The polymer conjugates may be provided in particulate form and blended with a pharmacologically acceptable carrier to facilitate administration. By "pharmacologically acceptable" is meant that the carrier is suitable for administration to a subject in its own right. In other words, administration of the carrier to a subject will not result in unacceptable toxicity, including allergenic responses and disease states. The term "carrier" refers to the vehicle with which the conjugate is contained prior to being administered.

As a guide only, a person skilled in the art may consider "pharmacologically acceptable" as an entity approved by a regulatory agency of a federal or state government or listed in the US Pharmacopeia or other generally recognised pharmacopeia for use in animals, and more particularly humans. Suitable pharmacologically acceptable carriers are described in Martin, Remington's Pharmaceutical Sciences, 18th Ed., Mack Publishing Co., Easton, Pa., (1990).

The polymer bioactive agent conjugates may also form part of or be formed into an article or device, or be applied as a coating on an article or device, and implanted in a subject. By being "implanted" is meant that the article or device is totally or partly introduced medically into a subject's body and which is intended to remain there after the procedure.

Suitable dosage amounts of the bioactive agents and dosing regimens of the polymer conjugates can be determined by a physician and may depend on the particular condition being treated, the rate of release of the agent form the polymer backbone, the severity of the condition as well the general age, health and weight of the subject.

The form of the polymer-bioactive agent conjugate may be adjusted to be suited to the required application such as a coating, film, pellet, capsule, fibres, laminate, foam etc. The difference in the form of the conjugate provides a means to alter the release profile of the bioactive agent. For example the amount of polymer and bioactive agent may be the same in two different structures however the differences in the surface area to volume, rates of hydration and diffusion paths from the different physical forms or structures can result in different rates of bioactive agent release from essentially the same polymer.

The adjustment of the form of the polymer conjugate to suit the application and further to adjust the form to further control bioactive agent release provides an additional advantage over purely compositional and polymer structural means to control the release profile of the bioactive agent.

Some of the compositional/structural means to control the release of the bioactive agent include: controlling the loading of the bioactive; composition of the other comonomers to adjust criteria such as hydrophobicity, flexibility, susceptibility to degradation, ability of the fragments to autocatalyse the polymer degradation, thermal stability of the polymer, mouldability, polymer solubility to assist casting etc.

In one set of embodiments, the bioactive agent may be released from the polymer conjugate such that it provides for a sustained bioactive delivery system. Such a delivery system may in its simplest form be the polymer conjugate provided in a desired shape, for example a pellet or more intricate shape. To promote surface area contact of the polymer conjugate under physiological conditions or with a biological environment, it may also be provided in the form of a foamed product or a coating on substrate.

By "sustained bioactive moiety delivery" is meant that the bioactive agent is released from the conjugate over a period of time, for example over a period of 10 or more minutes, 30 or more minutes, 60 or more minutes, 2 or more hours, 4 or more hours, 12 or more hours, 24 or more hours, 2 or more days, 5 or more days, 10 or more days, 30 or more days, 2 or more months, 4 or more months or over 6 or more months.

Polymer-bioactive agent conjugates of the present invention may be incorporated into drug delivery systems, therapeutic articles, devices or preparations, and pharmaceutical products for the treatment of ocular hypertension.

The polymer-bioactive agent conjugates of the present invention may be blended with one or more other polymers (for example, biodegradable polymers).

The present invention also provides a sustained drug delivery system comprising a polymer-bioactive agent conjugate of the invention. In one embodiment, the sustained drug delivery system may be in the form of an implant. The sustained drug delivery system may enable the prostaglandin analogues and/or β-blockers to be administered over a sustained period of time, such as for example, for at least 15 days, for at least 30 days, for at least 45 days, for at least 60 days, or for at least 90 days. A sustained release drug delivery system may be a more convenient way to administer the prostaglandin analogues and/or β-blockers, as it enables therapeutic levels of the drug to be continuously administered over an extended period time and allows the drug therapy schedule to be matched with a patient's visitation schedule to a medical or health practitioner.

Polymer-bioactive agent conjugates in accordance with the invention can be formed into an article or device. The article or device may be fabricated in a range of forms. Suitably, the article or device is a medical device, preferably an ocular implant. The polymer conjugates in accordance with the invention can also be incorporated or made into coatings for target in vitro and in vivo applications.

The polymer-bioactive agent conjugates in accordance with the invention can be formed into an article or device that is suitable for administration to the eye.

In some embodiments, a polymer-bioactive agent conjugate may be in the form of a solid article (such as a particle, rod or pellet), a semi-solid, a deformable solid, a gel, or a liquid, for placement in the eye of the subject.

In another aspect, the present invention provides an ocular implant for the treatment of glaucoma comprising a polymer-bioactive agent conjugate of any one of the embodiments described herein.

In one form, the implant is a rod-shaped and is able to be housed within the lumen of a needle, such as a 20 to 23 gauge needle. The outer diameter of the implant would be less than 0.5 mm, preferably about 0.4 mm and more preferably 0.3 mm. The length of the implant can be selected to deliver the required dose of drug.

The implant can be of a number of different structural forms. The ocular implant could be a solid, a semi-solid or even a gel. A solid implant would comprise material with a glass transition temperature (as measured by differential scanning calorimetry) above 37° C., a semi-solid would have a glass transition temperature at or just below 25-37° C. A gel could be formed by appropriate formulation of the polymer conjugate with an appropriate plasticiser. In one set of embodiments, the implant could be a hydrogel.

In yet another aspect the present invention provides an injectable article for placement in an eye of the subject, wherein the injectable article comprises a polymer-bioactive agent conjugate of any one of the embodiments described herein. In one form, the injectable article is an injectable gel.

It is contemplated that an ocular implant may be a bi-component polymer structure where the polymer-bioactive agent conjugate can either be incorporated in the outer or inner layers of the bi-component structure. Incorporating the polymer-bioactive agent conjugate in the outer layer could be done to give a measured dose. Additionally the inner polymer layer could be to provide structural integrity to allow the delivery via the needle. Additionally the inner polymer could be designed to degrade either faster or slower than the polymer conjugate layer. This could be to alter the rate of bioerosion or the implant.

Possible means for producing rod-shaped implants include:

- Melt extrusion of the polymer-bioactive agent conjugate or a material containing the polymer-bioactive agent conjugate through a shaped die.
- Simultaneous bi-component extrusion of the polymer-bioactive agent conjugate and other materials forming the outer or inner layers through an appropriate die.
- Sequential overcoating extrusion of one polymer later with another. For example a core polymer fibre of PLGA could be melt overcoated with a polymer containing the polymer-bioactive agent conjugate.
- It is also possible to solution coat an appropriate inner polymer carrier material (e.g. PLGA) with a solution containing the polymer-bioactive agent conjugate.

In another aspect, the present invention provides an ocular implant for the treatment of glaucoma in a subject comprising a polymer-drug conjugate of any one of the embodiments described herein. In some embodiments, the implant is in the form of a solid, semi-solid, gel or liquid suitable for placement in the eye of the subject.

In yet another aspect the present invention provides a pharmaceutical product for the treatment of a glaucoma in a subject, said pharmaceutical product comprising a polymer-bioactive agent conjugate of any one of the embodiments described herein. The pharmaceutical product may be an ocular implant or drug delivery system for the treatment of glaucoma. In one form, the pharmaceutical product is an implant in the form of a solid article, semi-solid, deformable solid, gel (including hydrogel), or liquid for placement in the eye of a subject.

In yet another aspect the present invention provides an injectable article for placement in an eye of the subject, wherein the injectable article comprises a polymer-bioactive agent conjugate of any one of the embodiments described herein. In one form, the injectable article is in the form of a gel.

In another aspect, there is provided a method for the treatment of glaucoma in a subject suffering glaucoma in one or both eyes, the method comprising administering a polymer-bioactive agent conjugate of any one of the embodiments described herein to an eye afflicted with glaucoma.

In one set of embodiments, the polymer-bioactive agent conjugate is contained in a solid article and method comprises implanting the article in an affected eye of a subject. In one set of embodiments, the method comprises depositing the solid article in the lumen of a needle and injecting the article into the eye from the needle.

In another aspect, there is provided use of a polymer-bioactive agent conjugate of any one of the embodiments described herein in the manufacture of a pharmaceutical product for the treatment of glaucoma. In one set of embodiments, the pharmaceutical product is in the form of an ocular implant. The ocular implant is a solid article and may be injectable.

In this specification "optionally substituted" is taken to mean that a group may or may not be substituted or fused (so as to form a condensed polycyclic group) with one, two, three or more of organic and inorganic groups (i.e. the optional substituent) including those selected from: alkyl, alkenyl, alkynyl, carbocyclyl, aryl, heterocyclyl, heteroaryl, acyl, aralkyl, alkaryl, alkheterocyclyl, alkheteroaryl, alkcarbocyclyl, halo, haloalkyl, haloalkenyl, haloalkynyl, haloaryl, halocarbocyclyl, haloheterocyclyl, haloheteroaryl, haloacyl, haloaryalkyl, hydroxy, hydroxyalkyl, hydroxyalkenyl, hydroxyalkynyl, hydroxycarbocyclyl, hydroxyaryl, hydroxyheterocyclyl, hydroxyheteroaryl, hydroxyacyl, hydroxyaralkyl, alkoxyalkyl, alkoxyalkenyl, alkoxyalkynyl, alkoxycarbocyclyl, alkoxyaryl, alkoxyheterocyclyl, alkoxyheteroaryl, alkoxyacyl, alkoxyaralkyl, alkoxy, alkenyloxy, alkynyloxy, aryloxy, carbocyclyloxy, aralkyloxy, heteroaryloxy, heterocyclyloxy, acyloxy, haloalkoxy, haloalkenyloxy, haloalkynyloxy, haloaryloxy, halocarbocyclyloxy, haloaralkyloxy, haloheteroaryloxy, haloheterocyclyloxy, haloacyloxy, nitro, nitroalkyl, nitroalkenyl, nitroalkynyl, nitroaryl, nitroheterocyclyl, nitroheteroayl, nitrocarbocyclyl, nitroacyl, nitroaralkyl, amino ($NH_2$), alkylamino, dialkylamino, alkenylamino, alkynylamino, arylamino, diarylamino, aralkylamino, diaralkylamino, acylamino, diacylamino, heterocyclamino, heteroarylamino, carboxy, carboxyester, amido, alkylsulphonyloxy, arylsulphenyloxy, alkylsulphenyl, arylsulphenyl, thio, alkylthio, alkenylthio, alkynylthio, arylthio, aralkylthio, carbocyclylthio, heterocyclylthio, heteroarylthio, acylthio, sulfoxide, sulfonyl, sulfonamide, aminoalkyl, aminoalkenyl, aminoalkynyl, aminocarbocyclyl, aminoaryl, aminoheterocyclyl, aminoheteroaryl, aminoacyl, aminoaralkyl, thioalkyl, thioalkenyl, thioalkynyl, thiocarbocyclyl, thioaryl, thioheterocyclyl, thioheteroaryl, thioacyl, thioaralkyl, carboxyalkyl, carboxyalkenyl, carboxyalkynyl, carboxycarbocyclyl, carboxyaryl, carboxyheterocyclyl, carboxyheteroaryl, carboxyacyl, carboxyaralkyl, carboxyesteralkyl, carboxyesteralkenyl, carboxyesteralkynyl, carboxyestercarbocyclyl, carboxyesteraryl, carboxyesterheterocyclyl, carboxyesterheteroaryl, carboxyesteracyl, carboxyesteraralkyl, amidoalkyl, amidoalkenyl, amidoalkynyl, amidocarbocyclyl, amidoaryl, amidoheterocyclyl, amidoheteroaryl, amidoacyl, amidoaralkyl, formylalkyl, formylalkenyl, formylalkynyl, formylcarbocyclyl, formylaryl, formylheterocyclyl, formylheteroaryl, formylacyl, formylaralkyl, acylalkyl, acylalkenyl, acylalkynyl, acylcarbocyclyl, acylaryl, acylheterocyclyl, acylheteroaryl, acylacyl, acylaralkyl, sulfoxidealkyl, sulfoxidealkenyl, sulfoxidealkynyl, sulfoxidecarbocyclyl, sulfoxidearyl, sulfoxideheterocyclyl, sulfoxideheteroaryl, sulfoxideacyl, sulfoxidearalkyl, sulfonylalkyl, sulfonylalkenyl, sulfonylalkynyl, sulfonylcarbocyclyl, sulfonylaryl, sulfonylheterocyclyl, sulfonylheteroaryl, sulfonylacyl, sulfonylaralkyl, sulfonamidoalkyl, sulfonamidoalkenyl, sulfonamidoalkynyl, sulfonamidocarbocyclyl, sulfonamidoaryl, sulfonamidoheterocyclyl, sulfonamidoheteroaryl, sulfonamidoacyl, sulfonamidoaralkyl, nitroalkyl, nitroalkenyl, nitroalkynyl, nitrocarbocyclyl, nitroaryl, nitroheterocyclyl, nitroheteroaryl, nitroacyl, nitroaralkyl, cyano, sulfate and phosphate groups.

Preferred optional substituents include the aforementioned reactive functional groups or moieties, polymer chains and alkyl, (e.g. $C_{1-6}$ alkyl such as methyl, ethyl, propyl, butyl, cyclopropyl, cyclobutyl, cyclopentyl or cyclohexyl), hydroxyalkyl (e.g. hydroxymethyl, hydroxyethyl, hydroxypropyl), alkoxyalkyl (e.g. methoxymethyl, methoxyethyl, methoxypropyl, ethoxymethyl, ethoxyethyl, ethoxypropyl etc) alkoxy (e.g. $C_{1-6}$ alkoxy such as methoxy, ethoxy, propoxy, butoxy, cyclopropoxy, cyclobutoxy), halo, trifluoromethyl, trichloromethyl, tribromomethyl, hydroxy, phenyl (which itself may be further substituted e.g., by $C_{1-6}$ alkyl, halo, hydroxy, hydroxy$C_{1-6}$ alkyl, $C_{1-6}$ alkoxy, halo$C_{1-6}$alkyl, cyano, nitro OC(O)$C_{1-6}$ alkyl, and amino), benzyl (wherein benzyl itself may be further substituted e.g., by $C_{1-6}$ alkyl, halo, hydroxy, hydroxy$C_{1-6}$alkyl, $C_{1-6}$ alkoxy, halo$C_{1-6}$ alkyl, cyano, nitro OC(O)$C_{1-6}$ alkyl, and amino), phenoxy (wherein phenyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro OC(O)$C_{1-6}$ alkyl, and amino), benzyloxy (wherein benzyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro OC(O)$C_{1-6}$ alkyl, and amino), amino, alkylamino (e.g. $C_{1-6}$ alkyl, such as methylamino, ethylamino, propylamino etc), dialkylamino (e.g. $C_{1-6}$ alkyl, such as dimethylamino, diethylamino, dipropylamino), acylamino (e.g. NHC(O)$CH_3$), phenylamino (wherein phenyl itself may be further substituted e.g., by $C_{1-6}$ alkyl, halo, hydroxy hydroxy$C_{1-6}$ alkyl, $C_{1-6}$ alkoxy, halo$C_{1-6}$ alkyl, cyano, nitro OC(O)$C_{1-6}$ alkyl, and amino), nitro, formyl, —C(O)-alkyl (e.g. $C_{1-6}$ alkyl, such as acetyl), O—C(O)-alkyl (e.g. $C_{1-6}$alkyl, such as acetyloxy), benzoyl (wherein the phenyl group itself may be further substituted e.g., by $C_{1-6}$ alkyl, halo, hydroxy hydroxy$C_{1-6}$ alkyl, $C_{1-6}$ alkoxy, halo$C_{1-6}$ alkyl, cyano, nitro OC(O)$C_{1-6}$alkyl, and amino), replacement of $CH_2$ with C=O, $CO_2H$, $CO_2$alkyl (e.g. $C_{1-6}$ alkyl such as methyl ester, ethyl ester, propyl ester, butyl ester), $CO_2$phenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro OC(O)$C_{1-6}$ alkyl, and amino), $CONH_2$, CONHphenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro OC(O)$C_{1-6}$ alkyl, and amino), CONHbenzyl (wherein benzyl itself may be further substituted e.g., by $C_{1-6}$ alkyl, halo, hydroxy hydroxyl $C_{1-6}$ alkyl, $C_{1-6}$ alkoxy, halo $C_{1-6}$ alkyl, cyano, nitro OC(O)$C_{1-6}$ alkyl, and amino), CONHalkyl (e.g. $C_{1-6}$ alkyl such as methyl amide, ethyl amide, propyl amide, butyl amide) CONHdialkyl (e.g. $C_{1-6}$ alkyl)aminoalkyl (e.g., HN $C_{1-6}$ alkyl-, $C_{1-6}$alkylHN-$C_{1-6}$ alkyl- and ($C_{1-6}$ alkyl)$_2$N—$C_{1-6}$ alkyl-), thioalkyl (e.g., HS $C_{1-6}$ alkyl-), carboxyalkyl (e.g., $HO_2CC_{1-6}$ alkyl-), carboxyesteralkyl (e.g., $C_{1-6}$ alkyl$O_2CC_{1-6}$ alkyl-), amidoalkyl (e.g., $H_2N(O)CC_{1-6}$ alkyl-, H($C_{1-6}$ alkyl)N(O)C$C_{1-6}$ alkyl-), formylalkyl (e.g., OHC$C_{1-6}$alkyl-), acylalkyl (e.g., $C_{1-6}$ alkyl(O)C$C_{1-6}$ alkyl-), nitroalkyl (e.g., $O_2NC_{1-6}$ alkyl-), sulfoxidealkyl (e.g., $R^3$(O)S$C_{1-6}$ alkyl, such as $C_{1-6}$ alkyl(O)S$C_{1-6}$ alkyl-), sulfonylalkyl (e.g., $R^3(O)_2SC_{1-6}$ alkyl- such as $C_{1-6}$ alkyl(O)$_2$S$C_{1-6}$ alkyl-), sulfonamidoalkyl (e.g., 2HRN(O)S$C_{1-6}$ alkyl, H($C_{1-6}$ alkyl)N(O)S$C_{1-6}$ alkyl-).

It is understood that the compounds of the present invention (including monomers and polymers) may exist in one or more stereoisomeric forms (eg enantiomers, diastereomers). The present invention includes within its scope all of these stereoisomeric forms either isolated (in for example enantiomeric isolation), or in combination (including racemic mixtures).

The following examples are intended to illustrate the scope of the invention and to enable reproduction and comparison. They are not intended to limit the scope of the disclosure in any way.

EXAMPLES

Brief Description of the Drawings

Examples of the invention are described with reference to the attached drawings.

In the drawings.

GENERAL EXPERIMENTAL PROCEDURES

Monomer Synthesis

Figure 1:
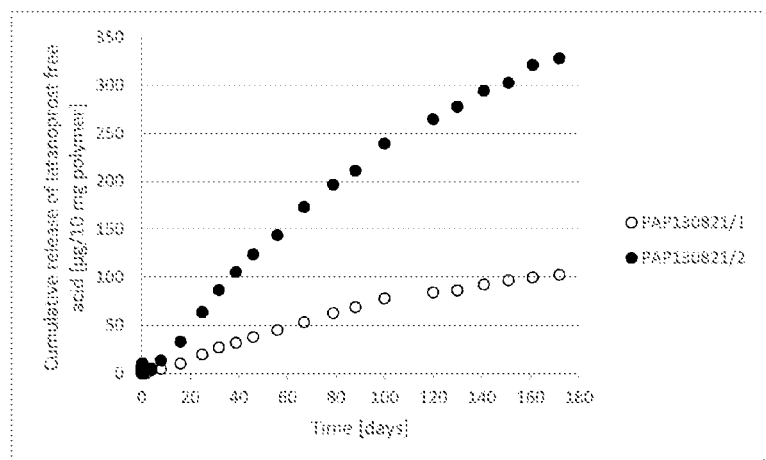
FIG. 1 is a graph showing the cumulative release of latanoprost free acid from the polymers of Example 54 and Example 55 in isotonic phosphate buffer pH 7.4.
Figure 2:
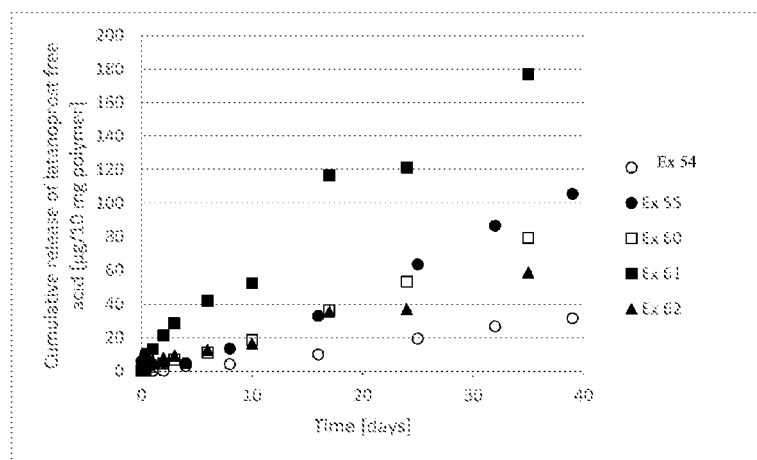
FIG. 2 is a graph showing the cumulative release of latanoprost free acid from the polymers of Example 54, Example 55, Example 60, Example 61 and Example 62 in isotonic phosphate buffer pH 7.4.
Figure 3:
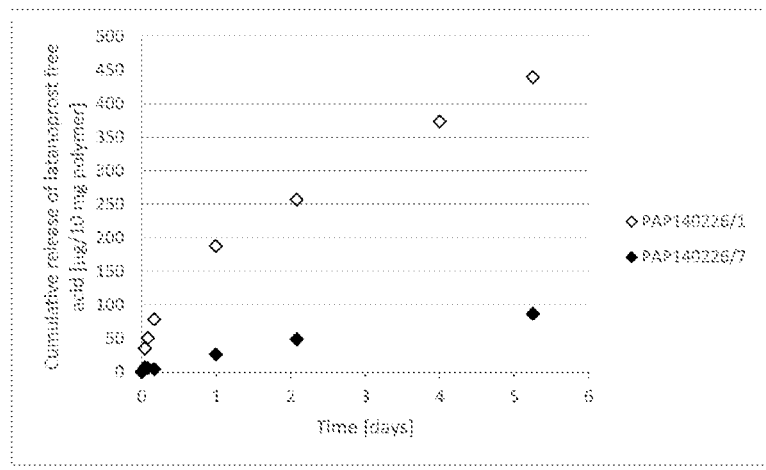
FIG. 3 is a graph showing the cumulative release of latanoprost free acid from the polymers of Example 64 and Example 70 in isotonic phosphate buffer pH 7.4.
Figure 4:
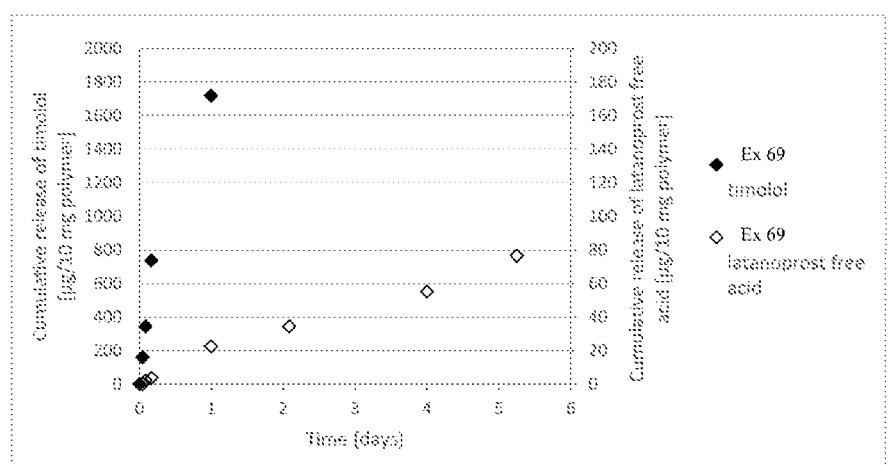
FIG. 4 is a graph showing the cumulative release of latanoprost free acid and timolol from the polymer of Example 69 in isotonic phosphate buffer pH 7.4.

Method 1a: Carbodiimide Mediated Ester Formation.

To a solution of the carboxylic acid substrate (≥1.5 mol eq. to the hydroxyl group), the alcohol derivative (1.0 eq) and DMAP (0.1 mol, eq. of the carboxylic acid group) in anhydrous DCM, N,N'-dicyclohexylcarbodiimide (DCC) (1 mol. eq. to the carboxylic acid group) is added at 0° C. The mixture is stirred at room temperature for 16 h or until the reaction is complete. The reaction mixture is filtered through a thin bed of Celite, concentrated and dried in vacuo. Column chromatography is used to isolate the pure product.

Method 1b: Carbodiimide Mediated Ester Formation. Acid Preactivation.

A solution of alcohol (1.0 eq.) in anhydrous DCM is added dropwise to a solution of the carboxylic acid substrate (~1.0 eq.), DCC (~1.0 eq.) and DMAP (0.1 eq.) in anhydrous DCM at 0° C. The mixture is stirred at room temperature for 16 h or until the reaction is complete. The reaction mixture is filtered through a thin bed of celite, concentrated and dried in vacuo.

Method 2: HBTU Mediated Ester Formation

A solution of the carboxylic acid substrate (1.0 eq.) in anhydrous THF is added dropwise into a stirring solution of HBTU (~1.2 eq.), the alcohol derivative (~1.6 eq.) and triethylamine (~4.3 eq.) in anhydrous THF under nitrogen atmosphere. The mixture is stirred at room temperature for 3 days, with the exclusion of light, or until the reaction is complete. The reaction is quenched with 1M aqueous citric acid and extracted with ethyl acetate. The organic phase is then washed with saturated aqueous sodium hydrogen carbonate, followed by brine. The organic phase is then dried over $Na_2SO_4$, filtered, concentrated and dried in vacuo.

Method 3: BOP-Cl Mediated Ester Formation

To a stirred solution of the alcohol derivative (1.0 eq.), the carboxylic acid substrate (1.0 eq.) and triethylamine (2.0 eq.) in anhydrous DCM, BOP-Cl (1.0 eq.) is added. The reaction mixture is stirred at room temperature for 16 h or until the reaction is complete. The reaction mixture is washed with saturated aqueous sodium hydrogen carbonate, water, and brine. The organic phase is then dried over $Na_2SO_4$, filtered, concentrated and dried in vacuo.

Method 4: Formation of Chloroformate

To a solution of the alcohol derivative (1.0 eq) and triphosgene (0.5 eq.) in anhydrous DCM, pyridine (1.3 eq) is added dropwise at −40° C. The reaction mixture is stirred at −40° C. for 2 h, then slowly warm to room temperature and stirred for 4 h or until the reaction is complete. The reaction mixture is filtered through a thin layer of silica gel, concentrated and dried in vacuo.

Method 5: Carbonate Formation

To a solution of requisite alcohol (1.0 eq) in anhydrous pyridine, chloroformate derivative (2-3 eq) is added at 0° C. The reaction mixture is stirred at room temperature for 16 h or until the reaction is complete. The residue is to extract in ethyl acetate and washed with water and brine. The organic phase is dried over $Na_2SO_4$, filtered, concentrated and dried in vacuo.

Preparation of Monomer-Bioactive Agent Conjugates Precursors

Example 1

2-(Prop-2-yn-1-yl)pent-4-yn-1-ol

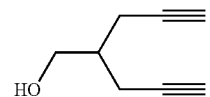

Prepared following the procedure of Carney et al. *Org. Lett.* 2008, 10, 3903.

Example 2

2-Hydroxypropane-1,3-diyl bis(hex-5-ynoate)

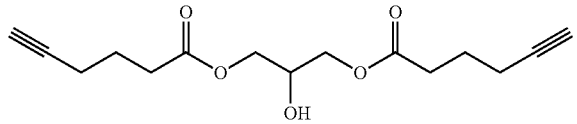 [SMILES: C#CCCCC(=O)OCC(O)COC(=O)CCCC#C]

5-Hexynoic acid (3.2 mL, 3.25 g 28.9 mmol), dihydroxyacetone dimer (1.0238 g, 5.68 mmol), DMAP (0.0348 g, 0.28 mmol) and DCC (4.7382 g, 22.9 mmol) in anhydrous DCM (50 mL) were reacted according to Method 1a outlined above. The crude residue was purified on a thin bed of silica gel, using 50% EtOAc in pet. spirit as eluent to give 2-oxopropane-1,3-diyl bis(hex-5-ynoate) as a white solid (quantitative yield). $^1$H NMR (400 MHz, CDCl$_3$) δ 4.76 (s, 4H), 2.58 (t, J=7.4 Hz, 4H), 2.29 (td, J=6.9, 2.7 Hz, 4H), 1.98 (t, J=2.7 Hz, 2H), 1.88 (p, J=7.1 Hz, 4H).

To a solution of 2-oxopropane-1,3-diyl bis(hex-5-ynoate) (376 mg, 1.35 mmol) in anhydrous THF (10 mL), sodium cyanoborohydride (94 mg, 1.51 mmol) was added. Glacial acetic acid was immediately added dropwise until the solution was at pH 4. The reaction mixture was stirred at room temperature for 30 mins. The mixture was quenched with water and extracted with DCM. The organic phase was dried over anhydrous $Na_2SO_4$, filtered, concentrated and dried in vacuo to give the title compound as a clear colourless oil (338.5 mg, 89% yield). $^1$H NMR (400 MHz, CDCl$_3$) δ

4.20-3.99 (m, 5H), 2.45 (t, J=7.4 Hz, 4H), 2.21 (td, J=6.9, 2.7 Hz, 4H), 1.92 (t, J=2.7 Hz, 2H), 1.79 (p, J=7.1 Hz, 4H). $^{13}$C NMR (101 MHz, CDCl$_3$) δ 173.12, 83.07, 69.34, 68.20, 65.14, 32.64, 23.45, 17.77.

Example 3

2-(Prop-2-yn-1-yl)pent-4-yn-1-yl 4-hydroxybenzoate

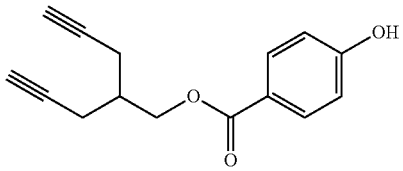 [SMILES: C#CCC(CC#C)COC(=O)c1ccc(O)cc1]

To a solution of 2-(prop-2-yn-1-yl)pent-4-yn-1-ol (*J. Org. Chem.* 2002, 67, 2778) (380 mg, 3.11 mmol), 4-acetoxybenzoic acid (619 mg, 3.43 mmol) and DMAP (36.9 mg, 0.30 mmol) in DCM at 0° C. was added EDC.HCl (663 mg, 3.46 mmol) and the resulting solution stirred at 0° C. for 1 h before allowing to warm to rt. The mixture was stirred for an additional 21 h before further EDC.HCl (652 mg, 3.40 mmol) was added. The resultant mixture was stirred at rt for an additional 24 h before Et$_2$O and H$_2$O were added. The product was extracted (Et$_2$O), washed (H$_2$O, then brine), dried (Na$_2$SO$_4$), filtered and concentrated under reduced pressure. Flash chromatography (0-100% EtOAc/petrol gradient elution) gave 2-(prop-2-yn-1-yl)pent-4-yn-1-yl 4-acetoxybenzoate (427 mg, 1.50 mmol, 48%) as a colourless oil. 2-(prop-2-yn-1-yl)pent-4-yn-1-yl 4-acetoxybenzoate (423.3 mg, 1.49 mmol) was dissolved in a 3:1 mixture of MeOH:H$_2$O (16 mL) before NH$_4$OAc (583.6 mg, 7.57 mmol) was added. The resultant mixture was stirred at rt for 76 h before EtOAc and H$_2$O were added. The product was extracted (EtOAc), washed (H$_2$O, then brine), dried (Na$_2$SO$_4$), filtered and concentrated under reduced pressure. Flash chromatography (0-100% EtOAc/petrol gradient elution) gave the title compound (295.1 mg, 1.22 mmol, 82%) as a white solid. ESI-MS: m/z 243 ([M+H]$^+$). $^1$H NMR (400 MHz CDCl$_3$): δ 7.95 (m, 2H), 6.86 (m, 2H), 4.38 (d, J=6.1 Hz, 2H), 2.47 (dd, J=6.2, 2.7 Hz, 4H), 2.28 (m, 1H), 2.03 (t, J=2.7 Hz, 2H).

Example 4

4-Hydroxy-N-(2-(prop-2-yn-1-yl)pent-4-yn-1-yl)benzamide

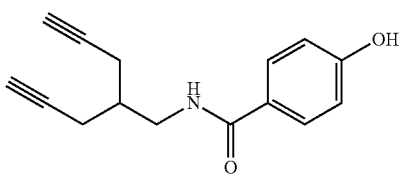 [SMILES: C#CCC(CC#C)CNC(=O)c1ccc(O)cc1]

In a similar manner to Example 3: 2-(Prop-2-yn-1-yl)pent-4-yn-1-yl 4-hydroxybenzoate described above 2-(prop-2-yn-1-yl)pent-4-yn-1-amine may be reacted with 4-acetoxybenzoic acid followed by NH$_4$.OAc mediated deacetylation to give the title compound.

Example 5

(5-Hydroxy-6-methylpyridine-3,4-diyl)bis(methylene) bis(hex-5-ynoate)

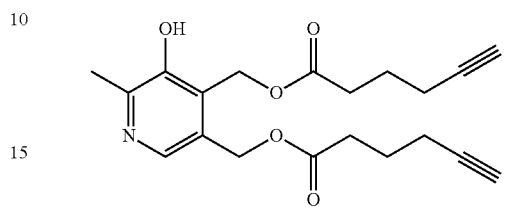

NaH (60% dispersion in mineral oil, 1.10 g, 27.5 mmol) was washed with dry petroleum spirit and dried under N$_2$. The solid was then suspended in DMF (100 mL) and cooled to 0° C. before pyridoxine.HCl (2.50 g, 12.2 mmol) was added and the mixture stirred at 0° C. for 30 min, before allowing to warm to rt for 15 min. The mixture was recooled to 0° C. and PMBCl (1.84 mL, 13.6 mmol) was added and the resulting mixture allowed to gradually warm to rt over 42 h. MeOH was added to quench before the solvent was removed under reduced pressure. Flash chromatography (0-30% MeOH/DCM gradient elution) gave (5-((4-methoxybenzyl)oxy)-6-methylpyridine-3,4-diyl)dimethanol (920 mg, 3.18 mmol, 26%) as a yellow-orange solid.

(5-((4-Methoxybenzyl)oxy)-6-methylpyridine-3,4-diyl)dimethanol (166 mg, 0.574 mmol), 5-hexynoic acid (160 μL, 1.45 mmol), DCC (284.3 mg, 1.38 mmol) and DMAP (10.5 mg, 0.085 mmol) in DCM were reacted for 4 h according to the procedure outlined in Method 1a, above. Flash chromatography (0-100% EtOAc/petrol gradient elution) gave (5-((4-methoxybenzyl)oxy)-6-methylpyridine-3,4-diyl)bis(methylene) bis(hex-5-ynoate) (236.2 mg, 0.495 mmol, 86%) as a colourless crystalline solid. To a solution of (5-((4-methoxybenzyl)oxy)-6-methylpyridine-3,4-diyl)bis(methylene) bis(hex-5-ynoate) (110.9 mg, 0.232 mmol) in DCM was added Et$_3$SiH (39 μL, 0.244 mmol) and the resulting mixture stirred at rt for 10 min. Trifluoroacetic acid (100 μL, 1.31 mmol) was added and the mixture stirred for a further 19 h before the solvent was removed under reduced pressure. Flash chromatography (0-30% MeOH/DCM gradient elution) yielded the title compound (83.1 mg, 0.232 mmol, quant.). ESI-MS: m/z 358 ([M+H]$^+$). $^1$H NMR (400 MHz): δ 8.32 (s, 1H), 5.29 (s, 2H), 5.26 (s, 2H), 2.69 (s, 3H), 2.56 (dt, J=11.5, 7.4 Hz, 4H), 2.27 (ddd, J=11.9, 6.9, 2.6 Hz, 4H), 1.99 (t, J=2.6 Hz, 1H), 1.96 (t, J=2.6 Hz, 1H), 1.86 (m, 4H). $^{13}$C NMR (100 MHz): δ 175.9, 172.6, 152.4, 148.1, 135.4, 132.6, 132.5, 83.0, 82.7, 69.9, 69.7, 60.5, 57.6, 32.7, 32.5, 23.4, 23.3, 17.9, 17.8, 16.6.

Example 6

2-(Prop-2-yn-1-yl)pent-4-ynoic acid

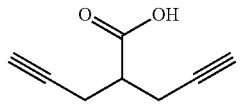

2M NaOH (2.6 mL, 5.2 mmol) was added to methyl 2-(prop-2-yn-1-yl)pent-4-ynoate (*Org. Lett.* 2008, 10(17), 3903) (383 mg, 2.55 mmol) before EtOH (19 mL) was added and the resulting solution heated to reflux for 22 h. The mixture was allowed to cool to rt and stirred for a further 42 h before the EtOH was removed under reduced pressure. The crude mixture was then diluted (Et$_2$O and H$_2$O) and the Et$_2$O fraction was extracted with H$_2$O before discarding. The aqueous fractions were combined and acidified with 2M HCl to pH~1 before the product was extracted with Et$_2$O. The organic fractions were dried (Na$_2$SO$_4$), filtered and concentrated under reduced pressure to provide the title compound (330 mg, 2.42 mmol, 95%) as a colourless solid which was used without further purification. $^1$H NMR (400 MHz CDCl$_3$): δ 2.83 (m, 1H), 2.68 (m, 4H), 2.05 (t, J=2.6 Hz, 2H). $^{13}$C NMR (100 MHz): δ 177.7, 80.2, 71.0, 42.9, 19.8.

Example 7

3-(Hex-5-ynoyloxy)-2-((hex-5-ynoyloxy)methyl)-2-methylpropanoic acid

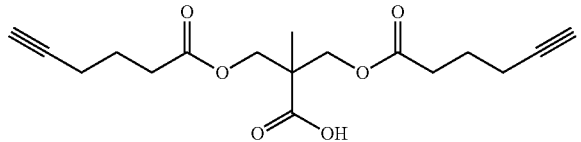 [SMILES: C#CCCCC(=O)OCC(C)(COC(=O)CCCC#C)C(=O)O]

5-Hexynoic acid (5.01 g, 44.9 mmol) was dissolved in DMF (42 mL) and cooled to 0° C. Oxalyl chloride (3.3 mL, 38.5 mmol) was added dropwise (gas evolution) and the resulting mixture stirred at 0° C. for 40 min. The solution was then added via cannula to a chilled (0° C.) solution of 2,2-dihydroxymethyl-propanoic acid (1.51 g, 11.3 mmol), NEt$_3$ (23.4 mL, 169 mmol) and DMAP (693 mg, 5.67 mmol) in DMF (50 mL) and the resulting mixture allowed to gradually warm to rt and stirred for 74 h. The mixture was acidified using 1M HCl to pH~2, before the product was extracted (EtOAc), washed (H$_2$O, then brine), dried (Na$_2$SO$_4$), filtered and concentrated under reduced pressure. Flash chromatography (20-60% EtOAc/petrol gradient elution) gave 4.6 g of a mixture of product and impurity, which was resubjected to flash chromatography (20-100% EtOAc/petrol gradient elution) to give the title compound as a colourless oil (3.11 g, 9.65 mmol, 85%). ESI-MS: m/z 345 ([M+Na]$^+$). $^1$H NMR (400 MHz CDCl$_3$): δ 1.30 (s, 3H), 1.84 (p, J=7.1 Hz, 4H), 1.98 (t, J=2.7 Hz, 2H), 2.26 (td, J=6.9, 2.6 Hz, 4H), 2.48 (t, J=7.4 Hz, 4H), 4.24 (d, J=11.1 Hz, 2H), 4.28 (d, J=11.1 Hz, 2H). $^{13}$C NMR (100 MHz): δ 178.2, 172.7, 83.2, 69.5, 65.2, 46.2, 32.8, 23.6, 17.93, 17.90.

Example 8

1,3-Bis(prop-2-yn-1-yloxy)propan-2-ol

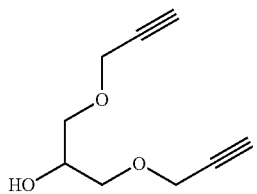

1,3-Dihydroxypropan-2-yl acetate (0.700 g, 5.22 mmol) was reacted with propargyl bromide (2.48 g, 20.9 mmol) in the presence of sodium hydride (0.835 g, 37.2 mmol) in 15 mL of anhydrous THF for 72 hours to give 1,3-bis(prop-2-yn-1-yloxy)propan-2-yl acetate. Saponification with LiOH (1 eq) in MeOH:THF:Water (3:1:1) is followed by acidification with citric acid and extraction into ethyl acetate. The organic phase is dried, filtered and the solvent removed to give the title compound.

Example 9

(Z)-Isopropyl 7-((1R,5S,6R,7R)-3-butyl-7-((R)-3-hydroxy-5-phenylpentyl)-2,4-dioxa-3-borabicyclo[3.2.1]octan-6-yl)hept-5-enoate

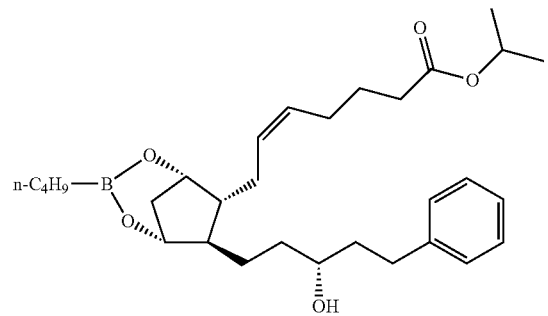

To latanoprost (222.0 mg, 0.51 mmol) in anhydrous DCM (10 mL) was added n-butylboronic acid (60.1 mg, 0.59 mmol). The mixture was heated at 45° C. for 1 h under nitrogen atmosphere. Solvent was then removed and dried in vacuo for 2 h. Additional anhydrous DCM was added and dried in vacuo for further 3 h. The residue was again heated in anhydrous DCM (10 mL) at 45° C. for 16 h. Solvent was removed under reduced pressure, obtaining a clear colourless oil and used directly in the next step without further purification. $^1$H NMR (400 MHz, CDCl$_3$) δ (ppm): 7.28-7.17 (m, 2H), 7.17-7.03 (m, 3H), 5.49-5.27 (m, 2H), 4.93 (ddd, J=15.2, 7.6, 4.9 Hz, 1H), 4.28-4.13 (m, 1H), 4.07-3.90 (m, 1H), 3.65-3.46 (m, 1H), 2.78-2.67 (m, 1H), 2.67-2.41 (m, 1H), 2.28-2.11 (m, 4H), 2.09-1.98 (m, 2H), 1.91-1.79 (m, 1H), 1.79-1.53 (m, 7H), 1.53-1.38 (m, 3H), 1.38-1.07 (m, 12H), 0.89-0.75 (m, 3H), 0.64-0.52 (m, 2H).

Also made using the same method are Examples 10 and 11:

Example 10

(Z)-7-((1R,5S,6R,7R)-3-Butyl-7-((R)-3-hydroxy-5-phenylpentyl)-2,4-dioxa-3-borabicyclo[3.2.1]octan-6-yl)hept-5-enoic acid

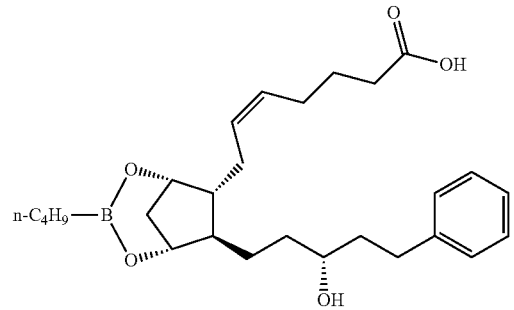

¹H NMR (400 MHz, CDCl₃) δ 7.33-7.25 (m, 2H), 7.23-7.10 (m, 3H), 5.62-5.44 (m, 1H), 5.44-5.34 (m, 1H), 4.31 (s, 1H), 4.04 (s, 1H), 3.73 (s, 1H), 2.89-2.47 (m, 2H), 2.47-1.99 (m, 6H), 1.99-1.87 (m, 1H), 1.87-1.07 (m, 15H), 0.93-0.82 (m, 4H), 0.82-0.71 (m, 1H), 0.71-0.52 (m, 2H).

Example 11

(Z)-Isopropyl 7-((1R,5S,6R,7R)-3-butyl-7-((R,E)-3-hydroxy-4-(3-(trifluoromethyl)phenoxy)but-1-en-1-yl)-2,4-dioxa-3-borabicyclo[3.2.1]octan-6-yl)hept-5-enoate

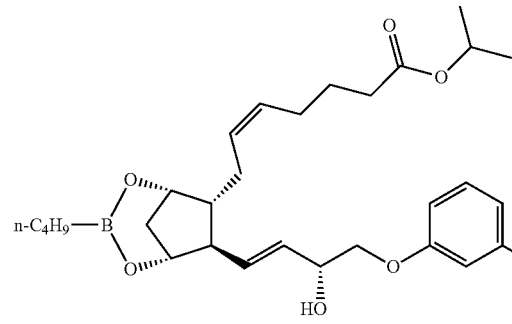

¹H NMR (400 MHz, CDCl₃) δ 7.44-7.35 (m, 1H), 7.30-7.19 (m, 1H), 7.17-7.11 (m, 1H), 7.11-7.03 (m, 1H), 5.77-5.66 (m, 1H), 5.66-5.56 (m, 1H), 5.52-5.30 (m, 2H), 5.09-4.90 (m, 1H), 4.60-4.44 (m, 1H), 4.34 (s, 1H), 4.20-4.10 (m, 1H), 4.06-3.77 (m, 2H), 2.53-2.37 (m, 1H), 2.34-2.20 (m, 4H), 2.16-2.04 (m, 2H), 2.03-1.93 (m, 1H), 1.92-1.73 (m, 2H), 1.73-1.59 (m, 2H), 1.43-1.24 (m, 6H), 1.23 (s, 3H), 1.21 (s, 3H), 0.95-0.83 (m, 4H), 0.72-0.55 (m, 2H).

Example 12

(Z)-2-(Prop-2-yn-1-yl)pent-4-yn-1-yl 7-((1R,2R,3R,5S)-3,5-dihydroxy-2-((R)-3-hydroxy-5-phenylpentyl)cyclopentyl)hept-5-enoate

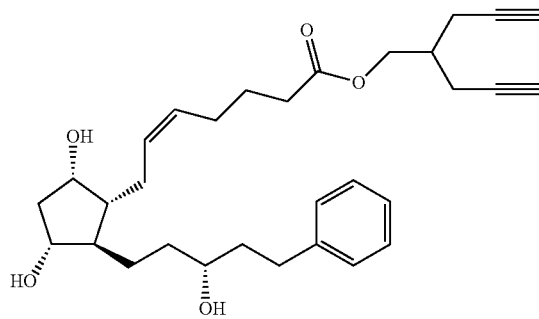 [SMILES: C#CCC(CC#C)COC(=O)CCC/C=C\C[C@@H]1[C@@H](CC[C@@H](O)CCc2ccccc2)[C@H](O)C[C@@H]1O]

A solution of latanoprost free acid (0.3989 g, 1.02 mmol) in anhydrous DCM (10 mL) was added dropwise into a solution mixture of 2-(prop-2-yn-1-yl)pent-4-yn-1-ol (0.1405 g, 1.15 mmol), HBTU (0.4391 g, 1.16 mmol) and triethylamine (0.60 mL, 0.4362 g, 4.31 mmol) in anhydrous DCM (5 mL) according to the procedure outlined in Method 2 above. The crude residue was purified on the automated flash chromatography using 0%-20% MeOH in DCM gradient elution to give the title compound as a clear colourless viscous oil (0.2251 g, 45% yield). ESI-MS: m/z 540 ([M+2Na]⁺). ¹H NMR (400 MHz, CDCl₃) δ 7.33-7.24 (m, 2H), 7.24-7.14 (m, 3H), 5.56-5.32 (m, 2H), 4.23-4.06 (m, 3H), 4.01-3.88 (m, 1H), 3.73-3.60 (m, 1H), 2.88-2.58 (m, 3H), 2.44-2.27 (m, 8H), 2.25-2.05 (m, 4H), 2.01 (t, J=2.7 Hz, 2H), 1.90-1.84 (m, 2H), 1.84-1.46 (m, 9H), 1.46-1.18 (m, 2H). ¹³C NMR (101 MHz, CDCl₃) δ 173.79, 142.20, 129.63, 129.57, 128.56, 128.55, 125.98, 81.04, 78.94, 74.88, 71.45, 70.63, 65.28, 53.06, 52.03, 42.68, 39.22, 36.38, 35.94, 33.70, 32.26, 29.79, 27.09, 26.76, 24.96, 20.00.

Example 13

2-(((Z)-7-((1R,2R,3R,5S)-3,5-Dihydroxy-2-((R)-3-hydroxy-5-phenylpentyl)cyclopentyl)hept-5-enoyl)oxy)propane-1,3-diyl bis(hex-5-ynoate)

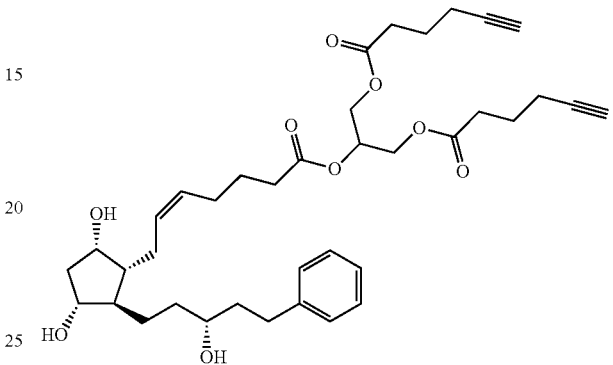

A solution of latanoprost free acid (0.1940 g, 0.50 mmol) in anhydrous DCM (10 mL) was added dropwise into a solution mixture of 2-hydroxypropane-1,3-diyl bis(hex-5-ynoate) (0.1800 g, 0.64 mmol), HBTU (0.2109 g, 0.56 mmol) and triethylamine (0.3 mL, 0.2181 g, 2.20 mmol) in anhydrous DCM (5 mL) according to the procedure outlined in Method 2 above. The crude residue was purified on the automated flash chromatography using 0%-30% MeOH in DCM gradient elution to give the title compound as a clear colourless oil (0.1346 g, 42% yield). ESI-MS: m/z 698 ([M+2Na]⁺). ¹H NMR (400 MHz, CDCl₃) δ 7.35-7.24 (m, 2H), 7.24-7.12 (m, 3H), 5.53-5.32 (m, 2H), 5.32-5.16 (m, 1H), 4.37-4.23 (m, 2H), 4.23-4.08 (m, 3H), 3.93 (t, J=8.6 Hz, 1H), 3.67 (m, 1H), 2.86-2.74 (m, 1H), 2.74-2.59 (m, 2H), 2.47 (tt, J=7.4, 3.7 Hz, 4H), 2.43-2.03 (m, 12H), 1.98 (t, J=2.6 Hz, 2H), 1.91-1.45 (m, 13H), 1.45-1.17 (m, 3H). ¹³C NMR (101 MHz, CDCl₃) δ 173.33, 172.66, 172.27, 142.12, 129.62, 129.27, 128.42, 125.83, 83.08, 78.72, 74.62, 71.28, 69.40, 69.38, 69.08, 68.94, 62.26, 62.18, 52.81, 51.81, 42.56, 39.07, 35.78, 33.53, 33.38, 32.78, 32.60, 32.12, 29.62, 26.93, 26.56, 26.53, 24.77, 24.73, 23.50, 23.44, 17.77, 17.74.

Example 14

2-(Prop-2-yn-1-yl)pent-4-yn-1-yl 4-(((Z)-7-((1R,2R,3R,5S)-3,5-dihydroxy-2-((R)-3-hydroxy-5-phenylpentyl)cyclopentyl)hept-5-enoyl)oxy)benzoate

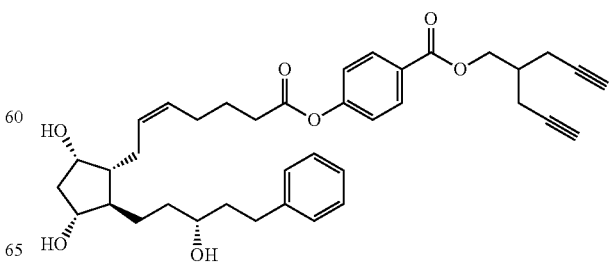

A solution of latanoprost free acid (102.4 mg, 0.26 mmol) in DCM (5 mL) was added dropwise to a solution of 2-(prop-2-yn-1-yl)pent-4-yn-1-yl 4-hydroxybenzoate (124.4 mg, 0.51 mmol), HBTU (111.1 mg, 0.29 mmol) and NEt$_3$ (214 μL, 1.54 mmol) in DCM (2 mL) according to the procedure outlined in Method 2. Flash chromatography (0-30% MeOH/DCM gradient elution) gave the title compound (57.7 mg, 0.094 mmol, 36%) as a colourless viscous oil. ESI-MS: m/z 615 ([M+H]$^+$). $^1$H NMR (400 MHz CDCl$_3$): δ 8.06 (m, 2H), 7.28 (m, 2H), 7.20-7.15 (m, 5H), 5.48 (m, 2H), 4.40 (d, J=6.1 Hz, 2H), 4.17 (s, 1H), 3.96 (s, 1H), 3.65 (m, 1H), 2.78 (ddd, J=13.5, 9.1, 6.3 Hz, 1H), 2.67 (m, 1H), 2.60 (t, J=7.3 Hz, 2H), 2.47 (dd, J=6.5, 2.6 Hz, 4H), 2.41-2.21 (m, 5H), 2.03 (t, J=2.6 Hz, 2H), 1.88-1.67 (m, 7H), 1.64-1.48 (m, 3H), 1.44-1.31 (m, 2H). $^{13}$C NMR (100 MHz): δ 171.9, 165.7, 154.6, 142.1, 131.4, 129.9, 129.4, 128.6, 128.5, 127.7, 126.0, 121.8, 81.0, 79.0, 75.0, 71.5, 70.7, 66.0, 53.1, 52.1, 42.7, 39.2, 36.6, 35.9, 33.9, 32.3, 29.8, 27.2, 26.7, 24.8, 20.2.

Example 15

(5-(((Z)-7-((1R,2R,3R,5S)-3,5-Dihydroxy-2-((R)-3-hydroxy-5-phenylpentyl)cyclopentyl)hept-5-enoyl)oxy)-6-methylpyridine-3,4-diyl)bis(methylene) bis(hex-5-ynoate)

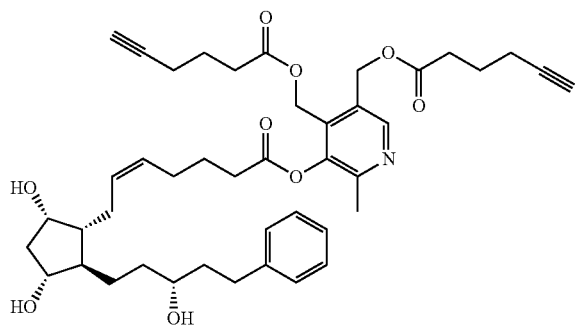 [SMILES: C#CCCCC(=O)OCc1cnc(C)c(OC(=O)CCC/C=C\C[C@@H]2[C@@H](CC[C@@H](O)CCc3ccccc3)[C@H](O)C[C@@H]2O)c1COC(=O)CCCC#C]

Latanoprost free acid (61.6 mg, 0.158 mmol), (5-hydroxy-6-methylpyridine-3,4-diyl)bis(methylene) bis(hex-5-ynoate) (82.1 mg, 0.230 mmol), HBTU (72.0 mg, 0.190 mmol), NEt$_3$ (128 μL, 0.923 mmol) and DCM (5 mL) were reacted according to the procedure outlined in Method 2. The crude material was purified by flash chromatography (0-30% MeOH/DCM gradient elution) to provide the title compound (74.8 mg, 0.102 mmol, 65%) as a colourless viscous oil. ESI-MS: m/z 730 ([M+H]$^+$). $^1$H NMR (400 MHz CDCl$_3$): δ 8.45 (s, 1H), 7.28 (m, 2H), 7.20-7.16 (m, 3H), 5.48 (m, 2H), 5.28 (s, 2H), 5.13 (s, 2H), 4.18 (s, 1H), 3.96 (m, 1H), 3.66 (m, 1H), 2.79 (ddd, J=13.6, 9.0, 6.3 Hz, 1H), 2.70-2.63 (m, 3H), 2.48 (t, J=7.4 Hz, 2H), 2.44-2.34 (m, 6H), 2.27-2.21 (m, 7H), 1.96 (t, J=2.6 Hz, 2H), 1.89-1.49 (m, 14H), 1.45-1.30 (m, 2H). $^{13}$C NMR (100 MHz): δ 172.7, 172.6, 171.4, 152.9, 147.1, 145.0, 142.2, 136.4, 130.1, 129.1, 128.6, 128.5, 126.0, 83.14, 83.13, 78.9, 74.9, 71.4, 69.6, 61.2, 57.0, 53.1, 52.0, 42.8, 39.3, 35.9, 33.5, 32.8, 32.6, 32.3, 29.8, 27.2, 26.8, 24.8, 23.51, 23.47, 19.5, 17.91, 17.88.

Example 16

2-((((Z)-7-((1R,2R,3R,5S)-3,5-Dihydroxy-2-((R)-3-hydroxy-5-phenylpentyl)cyclopentyl)hept-5-enoyl)oxy)methyl)-2-methylpropane-1,3-diylbis(hex-5-ynoate)

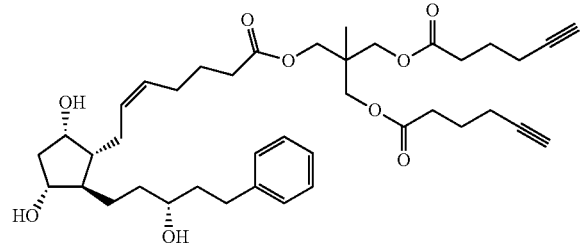 [SMILES: C#CCCCC(=O)OCC(C)(COC(=O)CCCC#C)COC(=O)CCC/C=C\C[C@@H]1[C@@H](CC[C@@H](O)CCc2ccccc2)[C@H](O)C[C@@H]1O]

A solution of 5-hexynoic acid (35 μL, 35.56 mg, 0.32 mmol), HBTU (83.3 mg, 0.22 mmol) and triethylamine (87 μL, 119.7 mg, 0.63 mmol) in anhydrous DCM (2 mL) was stirred at room temperature for ~1 hr or until HBTU was dissolved. The mixture was then added dropwise to a solution of (Z)-3-hydroxy-2-(hydroxymethyl)-2-methylpropyl 7-((1R,2R,3R,5S)-3,5-dihydroxy-2-((R)-3-hydroxy-5-phenylpentyl)cyclopentyl)hept-5-enoate (WO 2012/139164) (76.6 mg, 0.16 mmol) in anhydrous DCM (3 mL). The mixture was stirred at room temperature with the exclusion of light. After 4 days, a solution of 5-hexynoic acid (35 μL, 35.56 mg, 0.32 mmol), HBTU (83.7 mg, 0.22 mmol), triethylamine (87 μL, 119.7 mg, 0.63 mmol) in anhydrous DCM (2 mL) was added and stirred for further 3 days. The reaction was quenched with 1M aqueous citric acid and extracted with ethyl acetate. The organic phase was then washed with saturated aqueous sodium hydrogen carbonate, followed by brine. The organic phase was then dried over Na$_2$SO$_4$, filtered, concentrated and dried in vacuo. The crude residue was purified (SiO$_2$, MeOH:CHCl$_3$, 2:98). The title compound was obtained as a clear colourless oil (15.7 mg, 15% yield). ESI-MS: m/z 703 ([M+2Na]$^+$). $^1$H NMR (400 MHz, CDCl$_3$) δ 7.32-7.25 (m, 2H), 7.23-7.10 (m, 3H), 5.57-5.27 (m, 2H), 4.16 (bs, 1H), 4.08-3.88 (m, 7H), 3.71-3.61 (m, 1H), 2.87-2.73 (m, 1H), 2.73-2.58 (m, 1H), 2.51-2.42 (m, 4H), 2.40-2.03 (m, 12H), 1.98 (t, J=2.6 Hz, 2H), 1.91-1.46 (m, 12H), 1.46-1.23 (m, 2H), 1.02 (s, 3H). $^{13}$C NMR (101 MHz, CDCl$_3$) δ 173.63, 172.98, 142.20, 129.70, 129.44, 128.54, 128.53, 125.97, 83.16, 78.92, 74.84, 71.41, 69.50, 65.88, 65.81, 53.05, 51.99, 42.68, 39.22, 38.47, 35.93, 33.68, 32.83, 32.25, 29.78, 27.09, 26.75, 24.93, 23.58, 17.91, 17.26.

Example 17

(Z)-Isopropyl 7-((1R,2R,3R,5S)-3,5-dihydroxy-2-((R)-5-phenyl-3-((2-(prop-2-yn-1-yl)pent-4-ynoyl)oxy)pentyl)cyclopentyl)hept-5-enoate

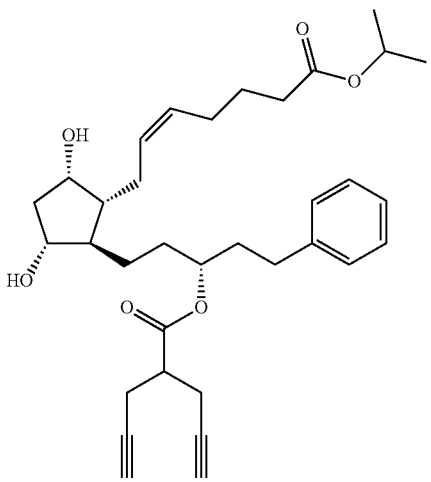 [SMILES: C#CCC(CC#C)C(=O)O[C@@H](CCc1ccccc1)CC[C@@H]1[C@@H](C/C=C\CCCC(=O)OC(C)C)[C@@H](O)C[C@H]1O]

A solution of example 9 (114.0 mg, 0.23 mmol) in anhydrous DCM (3 mL) was added dropwise to a solution of 2-(prop-2-yn-1-yl)pent-4-ynoic acid (33.9 mg, 0.25 mmol), DCC (52.9 mg, 0.26 mmol) and DMAP (8.4 mg, 0.07 mmol) in anhydrous DCM (4 mL) according to Method 1b outlined above. The residue was dissolved in methanol (6 mL) and stirred at room temperature for 2 days. The crude residue was purified on the automated flash chromatography using 0%-100% EtOAc in pet. spirit gradient elution to give the title compound as a clear colourless oil (56.8 mg, 45% yield). ESI-MS: m/z 573 ([M+Na]$^+$). $^1$H NMR (400 MHz, CDCl$_3$) δ 7.37-7.25 (m, 2H), 7.25-7.09 (m, 3H), 5.54-5.32 (m, 2H), 5.13-4.90 (m, 2H), 4.28-4.15 (m, 1H), 3.97-3.83 (m, 1H), 2.84-2.58 (m, 8H), 2.41-2.26 (m, 3H), 2.25-2.09 (m, 4H), 2.05 (t, J=2.6 Hz, 2H), 2.00-1.61 (m, 10H), 1.53-1.27 (m, 3H), 1.25 (s, 3H), 1.24 (s, 3H). $^{13}$C NMR (101 MHz, CDCl$_3$) δ 173.48, 172.09, 141.54, 129.80, 129.19, 128.45, 128.36, 125.98, 78.87, 74.78, 74.71, 70.73, 70.72, 67.68, 52.98, 51.71, 43.30, 42.49, 36.00, 34.04, 32.95, 31.69, 29.43, 26.91, 26.68, 24.92, 21.86, 20.06, 20.02.

Example 18

2-((((R)-1-((1R,2R,3S,5R)-3,5-Dihydroxy-2-((Z)-7-isopropoxy-7-oxohept-2-en-1-yl)cyclopentyl)-5-phenylpentan-3-yl)oxy)carbonyl)-2-methylpropane-1,3-diyl bis(hex-5-ynoate)

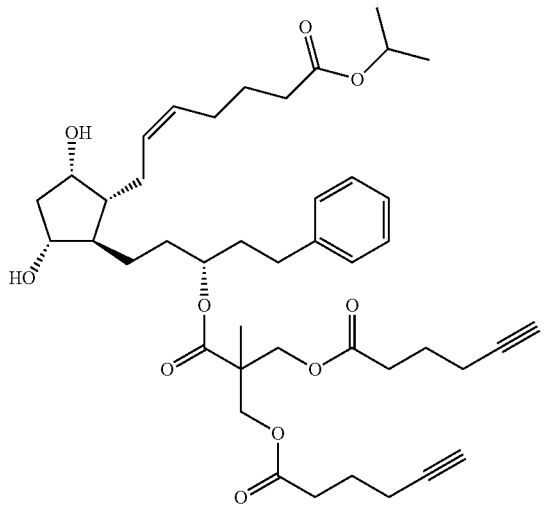 [SMILES: C#CCCCC(=O)OCC(C)(COC(=O)CCCC#C)C(=O)O[C@@H](CCc1ccccc1)CC[C@@H]1[C@@H](C/C=C\CCCC(=O)OC(C)C)[C@@H](O)C[C@H]1O]

A solution of example 9 (207.2 mg, 0.42 mmol) in anhydrous DCM (3 mL) was added dropwise to a solution of 3-(hex-5-ynoyloxy)-2-((hex-5-ynoyloxy)methyl)-2-methylpropanoic acid (143.0 mg, 0.44 mmol), DCC (99.3 mg, 0.48 mmol) and DMAP (15.2 mg, 0.12 mmol) in anhydrous DCM (5 mL) according to Method 1b outlined above. The residue was dissolved in methanol (6 mL) and stirred at room temperature for 24 hrs. The crude residue was purified on the automated flash chromatography using 0%-100% EtOAc in pet. spirit gradient elution to give the title compound as a clear colourless oil (104.2 mg, 42% yield). $^1$H NMR (400 MHz, CDCl$_3$) δ 7.34-7.26 (m, 2H), 7.23-7.10 (m, 3H), 5.47-5.32 (m, 2H), 5.05-4.93 (m, 2H), 4.34-4.19 (m, 4H), 4.16 (bs, 1H), 3.88 (bs, 1H), 2.71-2.50 (m, 2H), 2.48-2.39 (m, 4H), 2.39-2.25 (m, 5H), 2.24-2.18 (m, 4H), 2.18-2.01 (m, 3H), 1.96-1.60 (m, 15H), 1.49-1.29 (m, 4H), 1.26 (s, 3H), 1.23 (s, 3H), 1.21 (s, 3H). $^{13}$C NMR (101 MHz, CDCl$_3$) δ 173.56, 172.65, 172.58, 141.34, 129.99, 129.24, 128.65, 128.40, 126.22, 83.18, 78.94, 74.94, 74.74, 69.46, 67.79, 65.52, 53.00, 51.79, 46.49, 42.66, 36.01, 34.15, 32.87, 32.79, 32.77, 31.70, 29.51, 27.01, 26.79, 25.03, 23.55, 23.53, 21.98, 18.16, 17.87.

Example 19

(R)-1-((1R,2R,3S,5R)-3,5-Dihydroxy-2-((Z)-7-isopropoxy-7-oxohept-2-en-1-yl)cyclopentyl)-5-phenylpentan-3-yl (2-(prop-2-yn-1-yl)pent-4-yn-1-yl) succinate

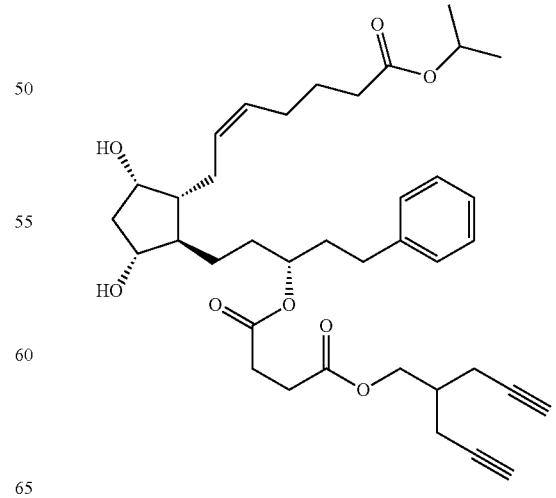

2-(Prop-2-yn-1-yl)pent-4-yn-1-ol (552.3 mg, 4.52 mmol) in anhydrous DCM (20 mL) was added succinic anhydride (5.99 mg, 5.99 mmol), DMAP (23.0 mg, 0.19 mmol) and pyridine (0.36 mL, 28.0 mmol). The mixture was heated at 45° C. for 16 h. The reaction mixture was washed with 1M HCl, followed by brine. The organic phase is then dried over $Na_2SO_4$, filtered, concentrated and dried in vacuo to give 4-oxo-4-((2-(prop-2-yn-1-yl)pent-4-yn-1-yl)oxy)butanoic acid as a clear colourless oil (quantitative yield). A solution of example 9 (117.7 mg, 0.24 mmol) in anhydrous DCM (1 mL) was added dropwise to a solution of 4-oxo-4-((2-(prop-2-yn-1-yl)pent-4-yn-1-yl)oxy)butanoic acid (60.6 mg, 0.27 mmol), DCC (62.2 mg, 0.30 mmol) and DMAP (3.8 mg, 0.03 mmol) in anhydrous DCM (5 mL) according to Method 1b outlined above. The residue was dissolved in methanol (2 mL) and stirred at room temperature for 3 days. The crude residue was purified on the automated flash chromatography using 0%-100% EtOAc in pet. spirit gradient elution to give the title compound as a clear colourless oil (81.9 mg, 54% yield) $^1$H NMR (400 MHz, $CDCl_3$) δ 7.24-7.17 (m, 2H), 7.14-7.07 (m, 3H), 5.43-5.25 (m, 2H), 4.97-4.83 (m, 2H), 4.15-4.03 (m, 3H), 3.83 (s, 1H), 2.67-2.43 (m, 7H), 2.35-2.17 (m, 7H), 2.15-1.96 (m, 4H), 1.95 (t, J=2.6 Hz, 2H), 1.91-1.75 (m, 4H), 1.75-1.50 (m, 6H), 1.43-1.23 (m, 3H), 1.16 (s, 3H), 1.15 (s, 3H). $^{13}$C NMR (101 MHz, $CDCl_3$) δ 173.48, 172.18, 172.05, 141.56, 129.62, 129.37, 128.44, 128.37, 125.95, 78.69, 74.60, 74.47, 70.58, 67.65, 65.48, 52.80, 51.63, 42.50, 36.26, 35.85, 34.09, 32.76, 31.76, 29.32, 29.27, 29.07, 26.95, 26.68, 24.96, 21.88, 19.85.

Example 20

(Z)-Isopropyl 7-((1R,2R,3R,5S)-3,5-dihydroxy-2-((R)-5-phenyl-3-((((2-(prop-2-yn-1-yl)pent-4-yn-1-yl)oxy)carbonyl)oxy)pentyl)cyclopentyl)hept-5-enoate

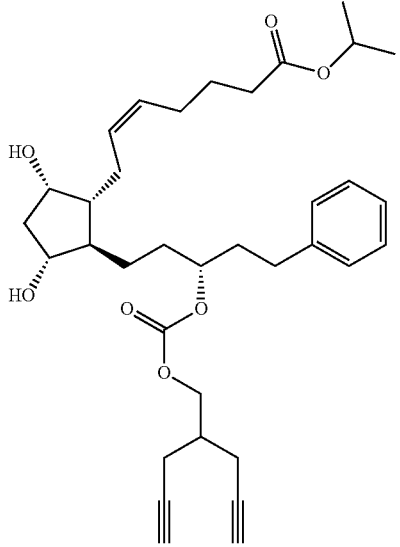 [SMILES: C#CCC(CC#C)COC(=O)O[C@@H](CCc1ccccc1)CC[C@@H]1[C@@H](C/C=C\CCCC(=O)OC(C)C)[C@@H](O)C[C@H]1O]

To a solution of 2-(prop-2-yn-1-yl)pent-4-yn-1-ol (716.9 mg, 5.87 mmol) and triphosgene (877.3 mg, 2.96 mmol) in anhydrous DCM (10 mL), pyridine (0.62 mL, 608.8 mg, 7.70 mmol) was added according to Method 4 outline above to give 2-(prop-2-yn-1-yl)pent-4-yn-1-yl carbonochloridate as a clear colourless oil (897.7 mg, 83% yield).

To a solution of example 9 (82.6 mg, 0.17 mmol) in anhydrous pyridine (3 mL), 2-(prop-2-yn-1-yl)pent-4-yn-1-yl carbonochloridate (68.4 mg, 0.37 mmol) was added according to Method 5 outlined above. The crude mixture was dissolved in methanol (5 mL) and stirred at room temperature for 16 h. The residue was purified on the automated flash chromatography using 0%-100% EtOAc in pet. spirit gradient elution to give the title compound as a clear colourless oil (21.9 mg, 23% yield). $^1$H NMR (400 MHz, $CDCl_3$) δ 7.34-7.24 (m, 2H), 7.23-7.11 (m, 3H), 5.48-5.30 (m, 2H), 4.99 (hept, J=6.3 Hz, 1H), 4.83-4.71 (m, 1H), 4.22 (dd, J=6.2, 1.3 Hz, 2H), 4.15 (bs, 1H), 3.91 (bs, 1H), 2.80-2.54 (m, 2H), 2.47-2.38 (m, 4H), 2.38-2.24 (m, 7H), 2.21-2.05 (m, 4H), 2.02 (t, J=2.7 Hz, 2H), 2.00-1.75 (m, 5H), 1.75-1.61 (m, 4H), 1.55-1.24 (m, 3H), 1.23 (s, 3H), 1.21 (s, 3H). $^{13}$C NMR (101 MHz, $CDCl_3$) δ 173.60, 155.07, 141.39, 129.85, 129.31, 128.58, 128.52, 128.44, 126.14, 78.84, 78.68, 74.79, 70.70, 68.50, 67.78, 66.48, 52.99, 51.83, 42.60, 36.45, 35.91, 34.15, 32.85, 31.73, 29.37, 27.02, 26.77, 25.03, 21.96, 21.76, 19.84.

Example 21

2-(Prop-2-yn-1-yl)pent-4-yn-1-yl 4-(((((R)-1-((1R,2R,3S,5R)-3,5-dihydroxy-2-((Z)-7-isopropoxy-7-oxohept-2-en-1-yl)cyclopentyl)-5-phenylpentan-3-yl)oxy)carbonyl)oxy)benzoate

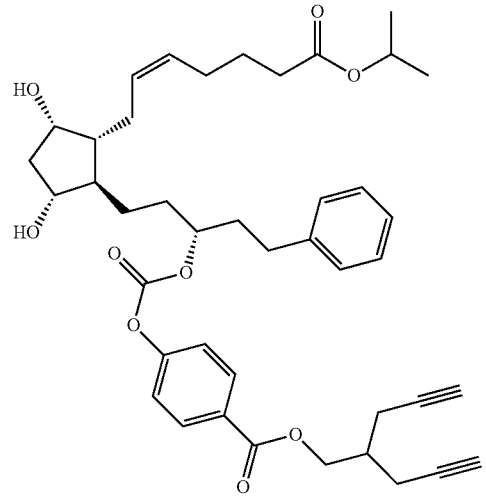 [SMILES: C#CCC(CC#C)COC(=O)c1ccc(OC(=O)O[C@@H](CCc2ccccc2)CC[C@@H]2[C@@H](C/C=C\CCCC(=O)OC(C)C)[C@@H](O)C[C@H]2O)cc1]

To a solution of 2-(prop-2-yn-1-yl)pent-4-yn-1-yl 4-hydroxybenzoate (660.0 mg, 2.72 mmol) and triphosgene (423.4 mg, 1.43 mmol) in anhydrous DCM (15 mL), pyridine (0.31 mL, 267.7 mg, 3.64 mmol) was added according to Method 4 outlined above to give 2-(prop-2-yn-1-yl)pent-4-yn-1-yl 4-((chlorocarbonyl)oxy)benzoate as a clear colourless oil (633.0 mg, 76% yield). To solution of example 9 (156.3 mg, 0.31 mmol) in anhydrous pyridine (8 mL), 2-(prop-2-yn-1-yl)pent-4-yn-1-yl 4-((chlorocarbonyl)oxy)benzoate (296.8 mg, 0.97 mmol) was added according to Method 5 outlined above. The crude mixture was dissolved in methanol (5 mL) and stirred at room temperature for 16 h. The residue was purified on the automated flash chromatography using 0%-100% EtOAc in pet. spirit gradient elution to give the title compound as a clear colourless oil (102.2 mg, 47% yield). ESI-MS: m/z 723 ([M+Na]$^+$) $^1$H NMR (400 MHz, $CDCl_3$) δ 8.17-7.98 (m, 2H), 7.35-7.24 (m, 5H), 7.24-7.08 (m, 3H), 5.50-5.32 (m, 2H), 5.00 (hept, J=6.3 Hz, 1H), 4.93-4.79 (m, 1H), 4.42 (d, J=6.1 Hz, 2H), 4.18 (s, 1H), 3.93 (s, 1H), 2.89-2.63 (m, 2H), 2.48 (dd, J=6.5, 2.6 Hz, 4H), 2.42-2.24 (m, 4H), 2.24-1.84 (m, 13H), 1.84-1.61 (m, 4H), 1.61-1.45 (m, 1H), 1.45-1.28 (m, 2H), 1.23 (s, 3H), 1.21 (s, 3H). $^{13}$C NMR (101 MHz, $CDCl_3$) δ 173.57, 165.56, 154.86, 152.95, 141.18, 131.40, 130.01, 129.25, 128.68, 128.47, 127.77, 126.29, 121.18, 80.09, 78.94, 77.36, 74.84, 70.73, 67.80, 66.00, 53.10, 51.91, 42.71, 36.58, 35.79, 34.15, 32.79, 31.74, 29.42, 27.06, 26.80, 25.04, 21.99, 20.18.

Example 22

(Z)-2-(Prop-2-yn-1-yl)pent-4-yn-1-yl 7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoate

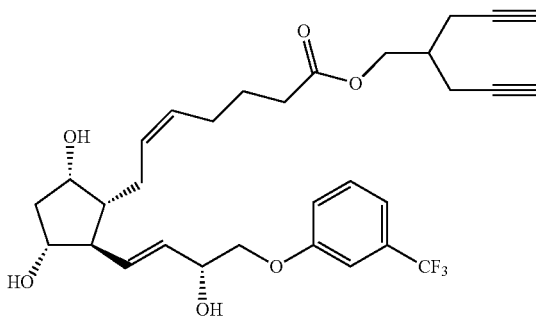 [SMILES: C#CCC(CC#C)COC(=O)CCC/C=C\C[C@@H]1[C@@H](/C=C/[C@@H](O)COc2cccc(C(F)(F)F)c2)[C@H](O)C[C@@H]1O]

A solution of travoprost free acid (316.5 mg, 0.69 mmol) in anhydrous THF (10 mL) was added dropwise into a solution mixture of 2-(prop-2-yn-1-yl)pent-4-yn-1-ol (97.2 mg, 0.79 mmol), HBTU (288.5 mg, 0.76 mmol) and triethylamine (0.38 mL, 276.3 mg, 2.73 mmol) in anhydrous DCM (5 mL) according to the procedure outlined in Method 2 above. The crude residue was purified on the automated flash chromatography using 0%-20% MeOH in DCM gradient elution to give the title compound as a clear colourless viscous oil (29.0 mg, 7.5% yield). ESI-MS: m/z 608 ([M+2Na]$^+$). $^1$H NMR (400 MHz, CDCl$_3$) δ 7.44-7.36 (m, 1H), 7.25-7.20 (m, 1H), 7.18-7.12 (m, 1H), 7.12-7.06 (m, 1H), 5.83-5.61 (m, 2H), 5.50-5.32 (m, 2H), 4.63-4.47 (m, 1H), 4.26-4.17 (m, 1H), 4.15 (d, J=6.2 Hz, 2H), 4.07-3.90 (m, 3H), 2.78-2.46 (m, 2H), 2.46-2.25 (m, 8H), 2.25-2.04 (m, 11H), 2.01 (t, J=2.6 Hz, 2H), 1.87-1.77 (m, 1H), 1.77-1.48 (m, 4H). $^{13}$C NMR (101 MHz, CDCl$_3$) δ 173.80, 158.77, 135.25, 133.27, 131.91, 130.22, 129.87, 129.43, 129.20, 122.67, 118.22, 118.03 (q, J$_{C-F}$=3.8 Hz), 111.62 (q, J$_{C-F}$=3.7 Hz), 78.25, 73.23, 72.23, 70.85, 65.31, 56.20, 50.68, 43.10, 36.38, 33.63, 31.07, 26.74, 25.81, 24.87, 20.00.

Example 23

(Z)-Isopropyl 7-((1R,2R,3R,5S)-3,5-dihydroxy-2-((R,E)-3-((2-(prop-2-yn-1-yl)pent-4-ynoyl)oxy)-4-(3-(trifluoromethyl)phenoxy)but-1-en-1-yl)cyclopentyl)hept-5-enoate

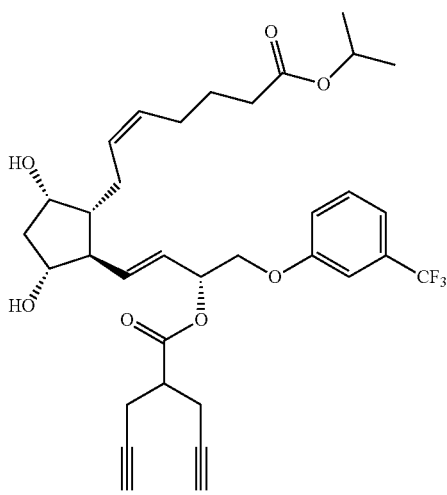 [SMILES: C#CCC(CC#C)C(=O)O[C@H](/C=C/[C@@H]1[C@@H](C/C=C\CCCC(=O)OC(C)C)[C@@H](O)C[C@H]1O)COc1cccc(C(F)(F)F)c1]

A solution of example 11 (124.6 mg, 0.22 mmol) in anhydrous DCM (3 mL) was added dropwise to a solution of 2-(prop-2-yn-1-yl)pent-4-ynoic acid (33.9 mg, 0.25 mmol), DCC (52.9 mg, 0.26 mmol) and DMAP (8.4 mg, 0.07 mmol) in anhydrous DCM (4 mL) according to Method 1b outlined above. The residue was dissolved in methanol (5 mL) and stirred at room temperature for 16 h. The crude residue was purified on the automated flash chromatography using 0%-100% EtOAc in pet. spirit gradient elution to give the title compound as a clear colourless oil (74.0 mg, 54% yield). ESI-MS: m/z 663 ([M+2Na]$^+$). $^1$H NMR (400 MHz, CDCl$_3$) δ 7.39 (t, J=8.0 Hz, 1H), 7.22 (d, J=7.7 Hz, 1H), 7.14 (d, J=11.3 Hz, 1H), 7.10-6.99 (m, 1H), 5.86-5.73 (m, 1H), 5.73-5.58 (m, 2H), 5.44-5.31 (m, 2H), 4.99 (hept, J=6.3 Hz, 1H), 4.24-4.17 (m, 1H), 4.17-4.05 (m, 2H), 4.03-3.86 (m, 1H), 2.85-2.73 (m, 1H), 2.72-2.53 (m, 4H), 2.44-2.21 (m, 4H), 2.21-2.00 (m, 7H), 1.98 (t, J=2.6 Hz, 1H), 1.87-1.75 (m, 1H), 1.73-1.60 (m, 2H), 1.60-1.48 (m, 1H), 1.25 (s, 3H), 1.21 (s, 3H). $^{13}$C NMR (101 MHz, CDCl$_3$) δ 173.57, 171.62, 158.67, 137.95, 132.20, 131.87, 130.20, 130.17, 128.94, 125.38, 118.24, 118.03 (q, J=3.7 Hz), 111.60 (q, J=3.7 Hz), 78.20, 73.28, 73.12, 69.40, 67.81, 56.35, 50.61, 43.17, 43.00, 34.10, 26.76, 25.84, 24.96, 21.97, 21.96, 20.06, 20.04.

Example 24

(Z)-7-((1R,2R,3R,5S)-3,5-Dihydroxy-2-((R)-3-hydroxy)-5 phenylpentyl)cyclopentyl)hept-5-enoic acid-2-prop-2-yn-1-yl)pent-4-ynoic anhydride

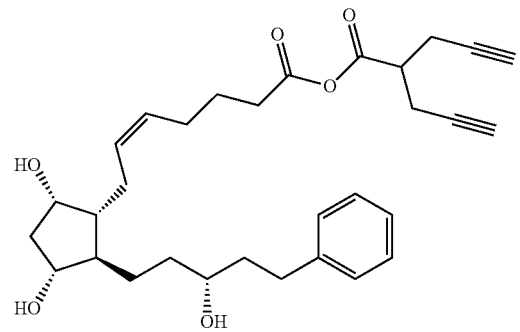 [SMILES: C#CCC(CC#C)C(=O)OC(=O)CCC/C=C\C[C@@H]1[C@@H](CC[C@@H](O)CCc2ccccc2)[C@H](O)C[C@@H]1O]

A mixture of latanoprost (0.1 g, 0.23 mmol), imidazole (0.157 g, 2.3 mmol) and tert-butyldimethylsilylchloride (0.174 g, 1.15 mmol) in DMF (0.7 mL) was stirred at room temperature for 16 h. The reaction was quenched by addition of 10% aq citric acid (2.8 mL). The mixture was extracted with tert-butylmethylether (3×5 mL), the combined organic phase was washed with 10% NaHCO$_3$ dried over anhydrous Na$_2$SO$_4$, filtered and concentrated in vacuo. The residue was purified by flash chromatography using 0%-20% EtOAc in pet. spirit gradient elution to give (Z)-Isopropyl 7-((1R,2R,3R,5S)-3,5-bis((tert-butyldimethylsilyl)oxy)-2-((R)-3-((tert-butyldimethylsilyl)oxy)-5-phenylpentyl)cyclopentyl) hept-5-enoate as a clear colourless oil (0.168 g, 94% yield).

To the tri-TBS protected latanoprost solution (505 mg, 0.652 mmol) in MeOH (10 mL), stirred under N$_2$, H$_2$O (1.0 mL) was added, followed by LiOH.H$_2$O (359 mg, 14.99 mmol). After stirring over three days, the reaction mixture was quenched with 5:3 mixture of saturated aqueous NH$_4$Cl and 2M aqueous NaHSO$_4$ (20 mL), and extracted with EtOAc (20 mL). The phases were separated, further aqueous NaHSO₄ (2M, 10 mL) was added to the aqueous phase, and the mixture was extracted with EtOAc (20 mL). the combined organic phases was washed with a mixture of 2:1 saturated aqueous NH₄Cl and 2M aqueous NaHSO₄ (30 mL), dried over anhydrous Na₂SO₄, filtered and concentrated in vacuo, to give (Z)-7-((1R,2R,3R,5S)-3,5-bis((tert-butyldimethylsilyl)oxy)-2-((R)-3-((tert-butyldimethylsilyl)oxy)-5-phenylpentyl)cyclopentyl)hept-5-enoic acid as a clear colourless oil (471 mg, 98% yield). ¹H NMR (400 MHz, CDCl₃) δ 7.27 (dt, J=6.5, 1.7 Hz, 2H), 7.21-7.14 (m, 3H), 5.48 (dt, J=7.7, 7.2 Hz, 1H), 5.34 (dt, J=10.8, 7.2 Hz, 1H), 4.14-3.98 (m, 1H), 3.85-3.61 (m, 2H), 2.73-2.54 (m, 2H), 2.41-2.26 (m, 2H), 2.23-2.00 (m, 5H), 1.86-1.62 (m, 5H), 1.62-1.22 (m, 6H), 0.94-0.85 (m, 27H), 0.05 (ddd, J=10.9, 6.2, 3.8 Hz, 18H). ¹³C NMR (101 MHz, CDCl₃) δ 177.87, 142.84, 130.43, 128.79, 128.48, 128.46, 125.79, 77.36, 77.16, 76.69, 72.88, 72.08, 50.35, 48.56, 44.41, 39.36, 34.06, 33.38, 31.82, 27.71, 26.73, 26.11, 26.03, 25.67, 24.83, 18.33, 18.23, 18.06, −3.91, −4.13, −4.20, −4.22, −4.59, −4.84.

A solution of tri-TBS protected latanoprost free acid (1.0 eq) in anhydrous DCM (4 mL) was added dropwise to a solution of 2-(prop-2-yn-1-yl)pent-4-ynoic acid (1.1 eq.), DCC (1.04 eq.) and DMAP (0.01 eq.) in anhydrous DCM (4 mL) according to Method 1b outlined above. The crude residue was purified on the automated flash chromatography using 0%-100% EtOAc in pet. spirit gradient elution to give (Z)-7-((1R,2R,3R,5S)-3,5-bis((tert-butyldimethylsilyl)oxy)-2-((R)-3-((tert-butyldimethylsilyl)oxy)-5-phenylpentyl)cyclopentyl)hept-5-enoic acid-2-prop-2-yn-1-yl)pent-4-ynoic anhydride.

A solution of tri-TBS latanoprost anhydride (1 eq.) and Bu₄NF (1 M solution in THF, 5.0 eq.) can be stirred for 16 h at room temperature and concentrated in vacuo. A solution of the residue in CH₂Cl₂ may be washed with 10% aq citric acid, dried over Na₂SO₄, filtered and concentrated in vacuo. The residue can be purified by automated flash chromatography using 0%-100% EtOAc in pet. spirit gradient elution in order to give the title compound.

Example 25

(Z)-Isopropyl 7-((1R,2R,3R,5S)-5-hydroxy-2-((R)-3-hydroxy-5-phenylpentyl)-3-((2-(prop-2-yn-1-yl)pent-4-ynoyl)oxy)cyclopentyl)hept-5-enoate

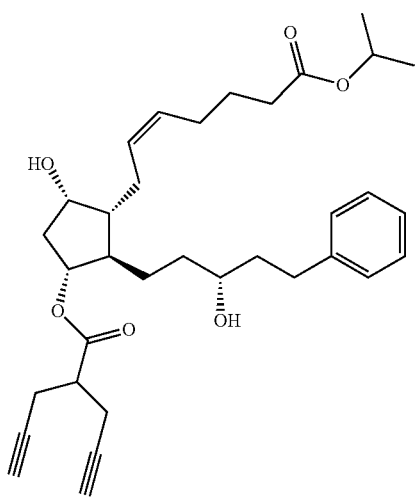 [SMILES: C#CCC(CC#C)C(=O)O[C@@H]1C[C@H](O)[C@H](C/C=C\CCCC(=O)OC(C)C)[C@H]1CC[C@@H](O)CCc1ccccc1]

Latanoprost and Novozyme 435 are dried under vacuum for 3 h. Anhydrous THF and vinyl 2-(prop-2-yn-1-yl)pent-4-ynoate are added. The reaction mixture may be heated at 64° C. for 16 h. The reaction may be quenched with chloroform and filtered. The solvent can then be removed in vacuo in order to give the title compound.

Example 26

(S)-1-(tert-Butylamino)-3-((4-morpholino-1,2,5-thiadiazol-3-yl)oxy)propan-2-yl (2-(prop-2-yn-1-yl)pent-4-yn-1-yl) carbonate

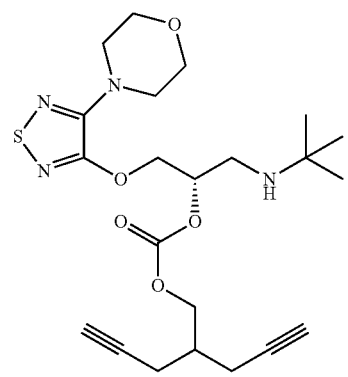 [SMILES: C#CCC(CC#C)COC(=O)O[C@@H](CNC(C)(C)C)COc1nsnc1N1CCOCC1]

To a stirring solution of timolol free base (506.0 mg, 1.6 mmol) and triethylamine (0.27 mL, 0.20 mmol) in anhydrous DCM (5 mL), a solution of 2-(prop-2-yn-1-yl)pent-4-yn-1-yl carbonochloridate (368.4 mg, 2.00 mmol) in anhydrous DCM (5 mL) was added dropwise at 0° C. The reaction mixture was stirred at room temperature for 24 h. The mixture was extracted and washed with saturated aqueous NaHCO₃ and saturated brine. The organic phase was dried over anhydrous Na₂SO₄, filtered, concentrated and dried in vacuo. The crude residue was purified on the automated flash chromatography using 0%-60% EtOAc in pet. spirit gradient elution to give the title compound as a clear colourless oil (206.3 mg, 28% yield). ESI-MS: m/z 465 (M⁺). ¹H NMR (400 MHz, CDCl₃) δ 5.08 (qd, J=5.9, 3.1 Hz, 1H), 4.62 (ddd, J=18.4, 11.7, 5.0 Hz, 2H), 4.25-4.16 (m, 2H), 3.83-3.71 (m, 4H), 3.56-3.39 (m, 4H), 2.92-2.78 (m, 2H), 2.44-2.30 (m, 4H), 2.24-2.08 (m, 1H), 2.06-1.90 (m, 2H), 1.06 (s, 9H). ¹³C NMR (101 MHz, CDCl₃) δ 154.59, 153.32, 149.78, 80.60, 76.54, 70.72, 70.70, 70.02, 68.67, 66.52, 50.32, 47.80, 42.65, 36.32, 28.96, 19.74, 19.73.

Example 27

(S)-1-(tert-Butylamino)-3-((4-morpholino-1,2,5-thiadiazol-3-yl)oxy)propan-2-yl-2-(prop-2-yn-1-yl)pent-4-ynoate

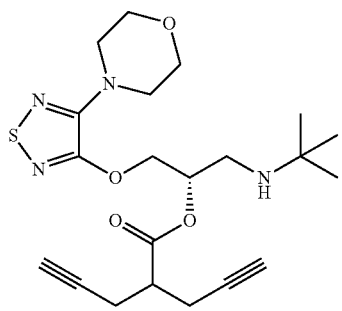 [SMILES: C#CCC(CC#C)C(=O)O[C@@H](CNC(C)(C)C)COc1nsnc1N1CCOCC1]

To a stirring solution of timolol free base (1.0 g, 3.16 mmol) in anhydrous DCM (25 mL), 2-(prop-2-yn-1-yl)pent-4-ynoic acid (0.4317 g, 3.17 mmol), triethylamine (0.89 mL, 0.647 g, 2.02 mmol) and BOP-Cl (0.8131 g, 3.19 mmol) were added according to the procedure outlined in Method 3. The reaction mixture was stirred at room temperature for 16 h. The crude residue was purified by automated flash chromatography using 0%-70% EtOAc in pet. spirit gradient elution to give the title compound as a clear colourless oil (0.8145 g, 59% yield). ESI-MS: m/z 435.3 ([M+H]$^+$). $^1$H NMR (400 MHz, CDCl$_3$) δ 5.40-5.25 (m, 1H), 4.66-4.57 (m, 2H), 3.87-3.73 (m, 4H), 3.57-3.41 (m, 4H), 2.85 (t, J=9.5 Hz, 2H), 2.82-2.72 (m, 1H), 2.72-2.53 (m, 4H), 2.02-1.91 (m, 2H), 1.53-1.44 (m, 1H), 1.09 (s, 9H). $^{13}$C NMR (101 MHz, CDCl$_3$) δ 171.86, 153.52, 149.93, 80.45, 80.41, 73.09, 70.91, 70.80, 70.25, 66.67, 50.92, 47.98, 43.28, 42.84, 28.89, 20.16, 20.04.

Example 28

(S)-1-(4-(2-(Cyclopropylmethoxy)ethyl)phenoxy)-3-isopropylamino)propan-2-yl-2-(prop-2-yn-1-yl)pent-4-ynoate

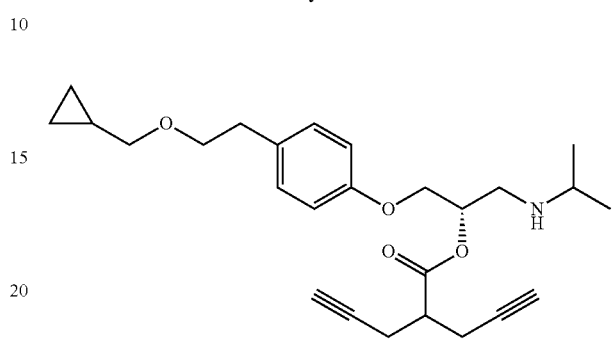

To a stirring solution of betaxolol (0.971 g, 3.16 mmol) in anhydrous DCM (25 mL), 2-(prop-2-yn-1-yl)pent-4-ynoic acid (0.43 g, 3.17 mmol), triethylamine (0.88 mL, 0.64 g, 2.02 mmol) and BOP-Cl (0.804 g, 3.19 mmol) were added according to the procedure outlined in Method 3 above. The reaction mixture was stirred at room temperature for 16 h. The crude residue was purified by automated flash chromatography using 0%-50% EtOAc in pet. spirit gradient elution to give the title compound as a clear colourless oil (0.679 g, 50% yield.). ESI-MS: m/z 426.3 (M$^+$+H).

Using the procedures described the following monomers shown in Table 4 may be prepared.

| Example | Drug | Linking Point | Linkage | Alkyne/azide precursor |
|---|---|---|---|---|
| 29 | LTP | 15-OH | Carbonate | |
| 30 | LTP | 1-COOH | Ester | |
| 31 | LTP | 15-OH | Carbonate | |

| 32 | LTP | 1-COOH | Ester | 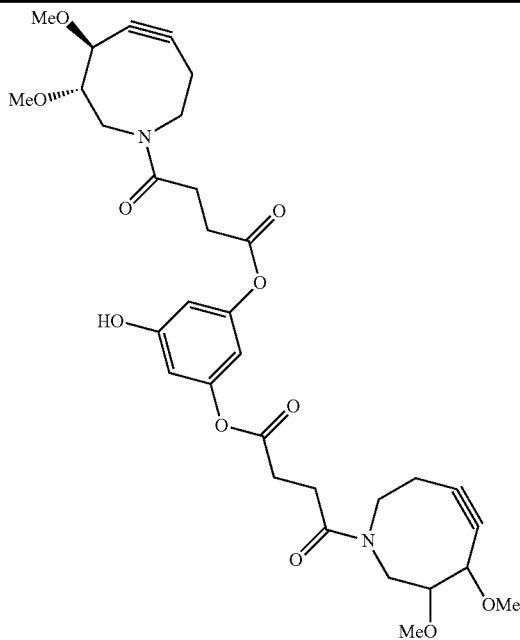 |
|---|---|---|---|---|
| 33 | LTP | 1-COOH | Ester | 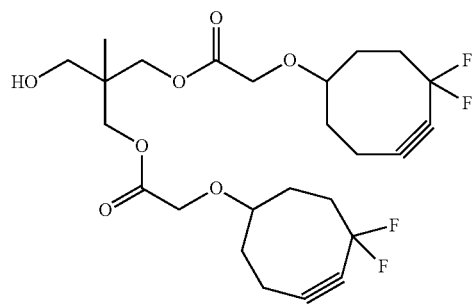 [SMILES: CC(CO)(COC(=O)COC1CCC#CC(F)(F)CC1)COC(=O)COC1CCC#CC(F)(F)CC1] |
| 34 | LTP | 15-OH | Carbonate | 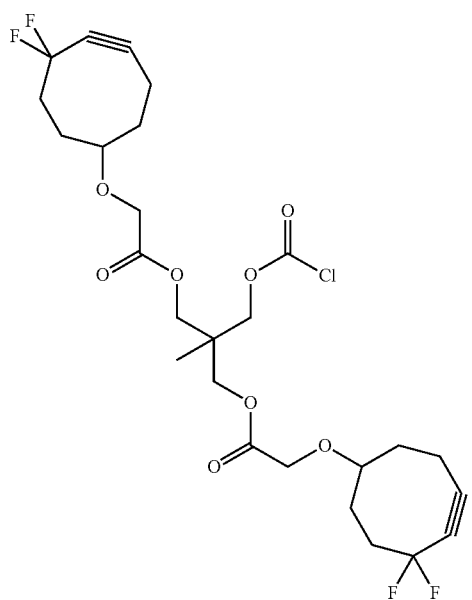 [SMILES: CC(COC(=O)Cl)(COC(=O)COC1CCC#CC(F)(F)CC1)COC(=O)COC1CCC#CC(F)(F)CC1] |

| | | | | |
|---|---|---|---|---|
| 35 | TVP | 15-OH | Carbonate | 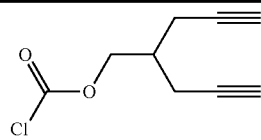 |
| 36 | TVP | 15-OH | Carbonate | 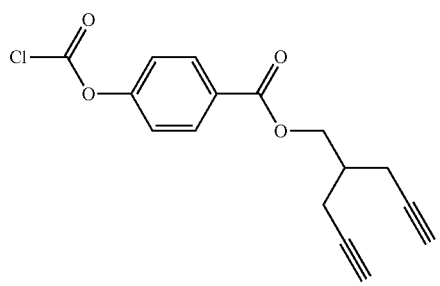 [SMILES: C#CCC(CC#C)COC(=O)c1ccc(OC(=O)Cl)cc1] |
| 37 | LTP | 1-COOH | Ester | 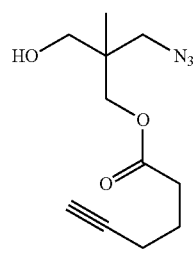 [SMILES: C#CCCCC(=O)OCC(C)(CO)CN=[N+]=[N-]] |
| 38 | LTP | 1-COOH | Ester | 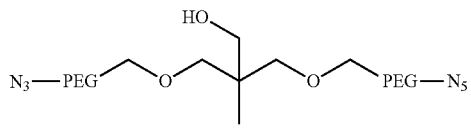 |
| 39 | LTP | 15-OH | Carbonate | 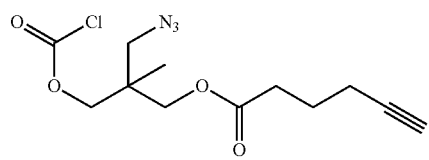 [SMILES: C#CCCCC(=O)OCC(C)(CN=[N+]=[N-])COC(=O)Cl] |
| 40 | TIM | OH | Ester | 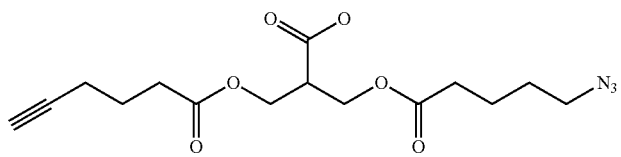 [SMILES: C#CCCCC(=O)OCC(COC(=O)CCCCN=[N+]=[N-])C(=O)O] |
| 41 | TIM | OH | Ester | 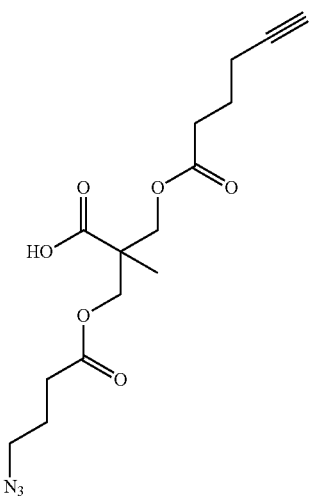 [SMILES: C#CCCCC(=O)OCC(C)(COC(=O)CCCN=[N+]=[N-])C(=O)O] |

| | | | | |
|---|---|---|---|---|
| 42 | TIM | OH | Carbonate | 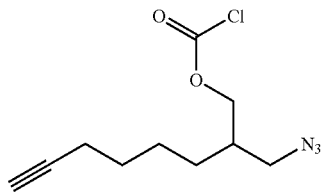 [SMILES: C#CCCCCC(CN=[N+]=[N-])COC(=O)Cl] |
| Example | Production Method | Monomer |
|---|---|---|
| 29 | Method 5 | 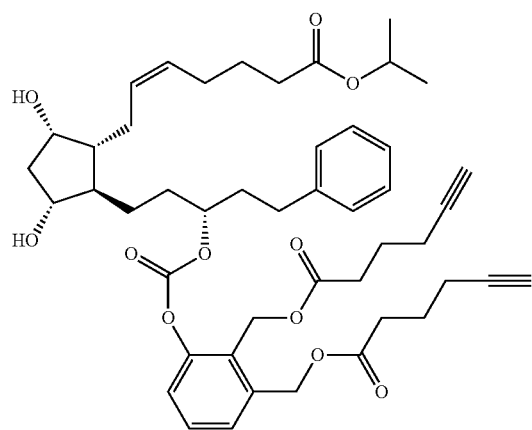 [SMILES: C#CCCCC(=O)OCc1cccc(OC(=O)O[C@@H](CCc2ccccc2)CC[C@@H]2[C@@H](C/C=C\CCCC(=O)OC(C)C)[C@@H](O)C[C@H]2O)c1COC(=O)CCCC#C] |
| 30 | Method 2 | 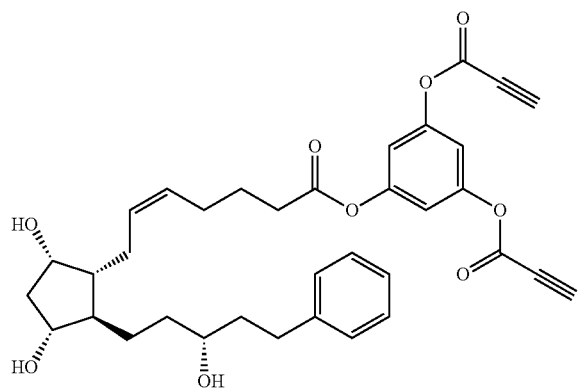 [SMILES: C#CC(=O)Oc1cc(OC(=O)C#C)cc(OC(=O)CCC/C=C\C[C@@H]2[C@@H](CC[C@@H](O)CCc3ccccc3)[C@H](O)C[C@@H]2O)c1] |
| 31 | Method 2 | 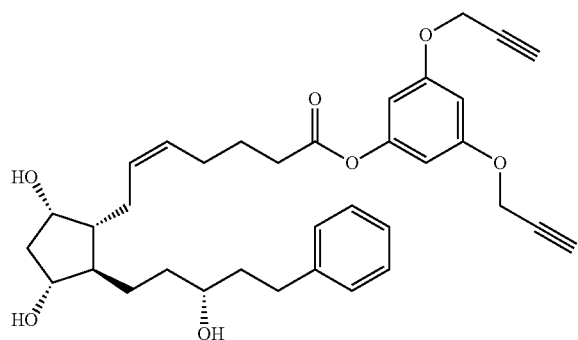 [SMILES: C#CCOc1cc(OCC#C)cc(OC(=O)CCC/C=C\C[C@@H]2[C@@H](CC[C@@H](O)CCc3ccccc3)[C@H](O)C[C@@H]2O)c1] |

| | | |
|---|---|---|
| 32 | Method 2 | 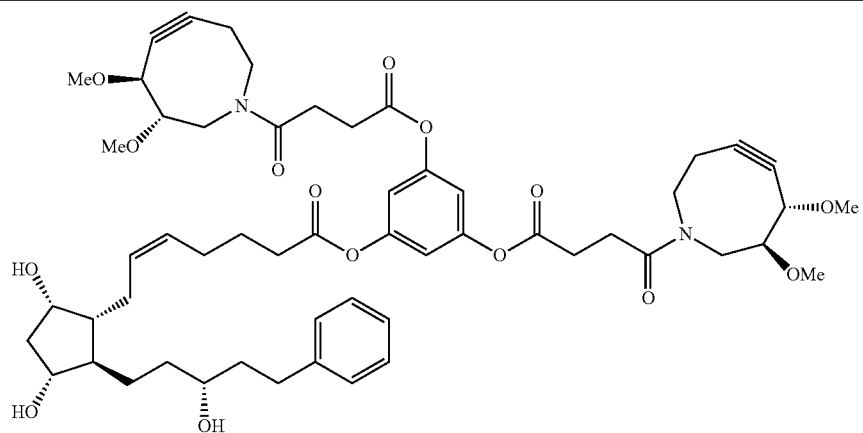 |
| 33 | Method 2 | 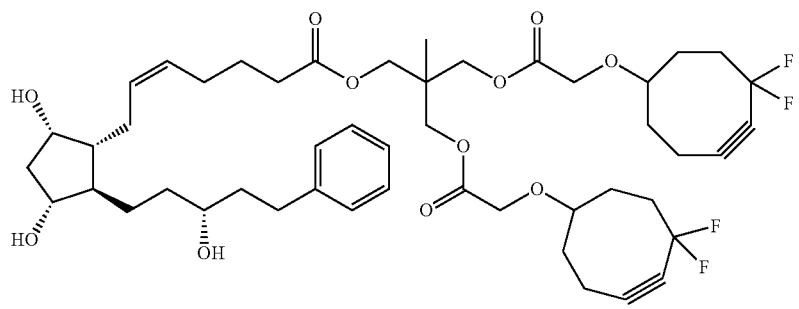 [SMILES: CC(COC(=O)CCC/C=C\C[C@@H]1[C@@H](CC[C@@H](O)CCc2ccccc2)[C@H](O)C[C@@H]1O)(COC(=O)COC1CCC#CC(F)(F)CC1)COC(=O)COC1CCC#CC(F)(F)CC1] |
| 34 | Method 5 | 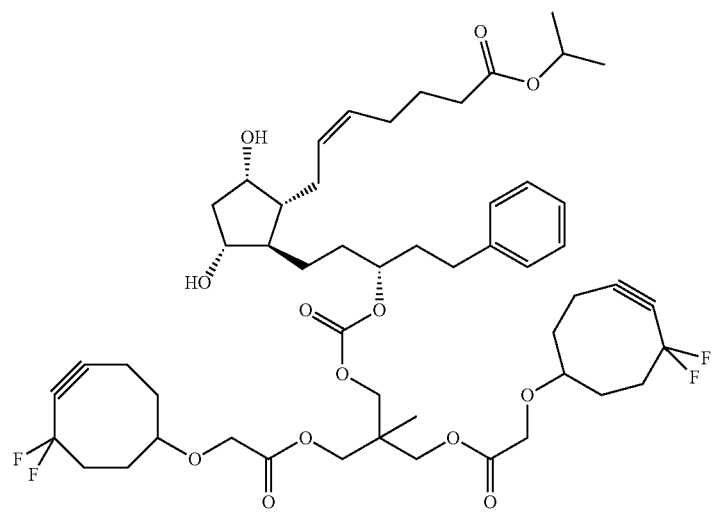 [SMILES: CC(C)OC(=O)CCC/C=C\C[C@@H]1[C@@H](CC[C@H](CCc2ccccc2)OC(=O)OCC(C)(COC(=O)COC2CCC#CC(F)(F)CC2)COC(=O)COC2CCC#CC(F)(F)CC2)[C@H](O)C[C@@H]1O] |
| 35 | Method 5 | 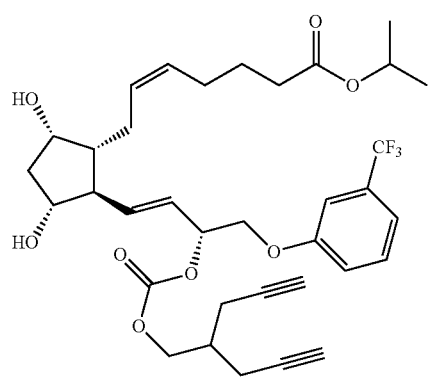 [SMILES: C#CCC(CC#C)COC(=O)O[C@H](/C=C/[C@@H]1[C@@H](C/C=C\CCCC(=O)OC(C)C)[C@@H](O)C[C@H]1O)COc1cccc(C(F)(F)F)c1] |

| | | |
|---|---|---|
| 36 | Method 5 | 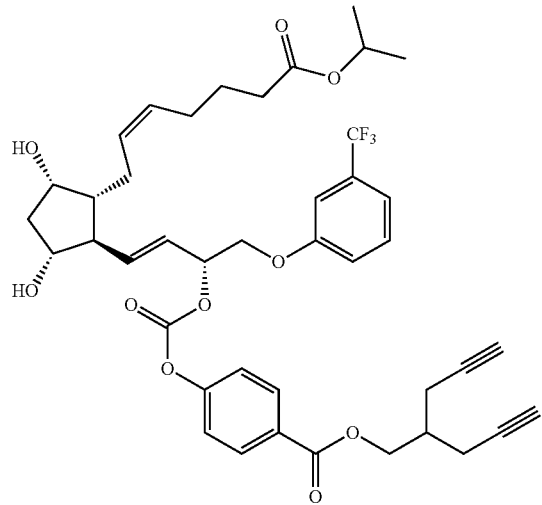 [SMILES: C#CCC(CC#C)COC(=O)c1ccc(OC(=O)O[C@H](/C=C/[C@@H]2[C@@H](C/C=C\CCCC(=O)OC(C)C)[C@@H](O)C[C@H]2O)COc2cccc(C(F)(F)F)c2)cc1] |
| 37 | Method 2 | 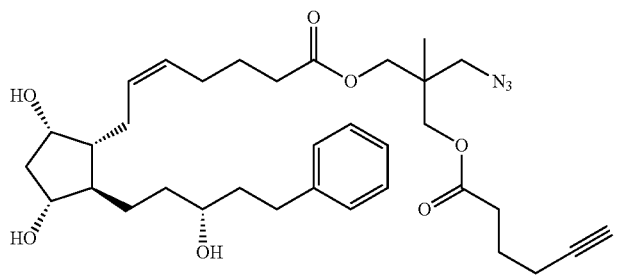 [SMILES: C#CCCCC(=O)OCC(C)(CN=[N+]=[N-])COC(=O)CCC/C=C\C[C@@H]1[C@@H](CC[C@@H](O)CCc2ccccc2)[C@H](O)C[C@@H]1O] |
| 38 | Method 5 | 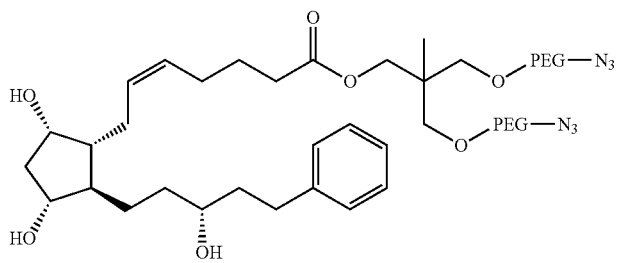 |
| 39 | Method 5 | 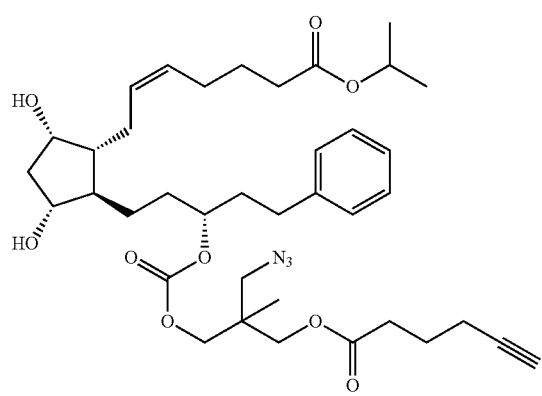 [SMILES: C#CCCCC(=O)OCC(C)(CN=[N+]=[N-])COC(=O)O[C@@H](CCc1ccccc1)CC[C@@H]1[C@@H](C/C=C\CCCC(=O)OC(C)C)[C@@H](O)C[C@H]1O] |

| | | |
|---|---|---|
| 40 | Method 3 | 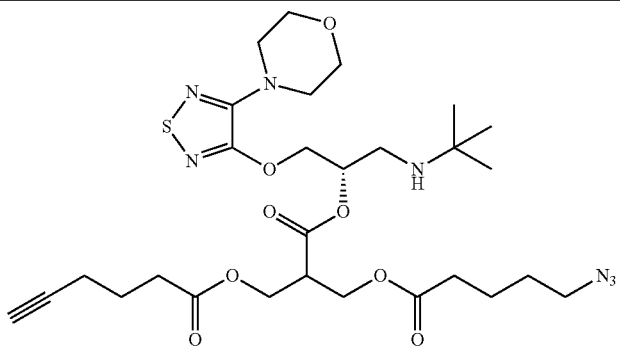 |
| 41 | Method 3 | 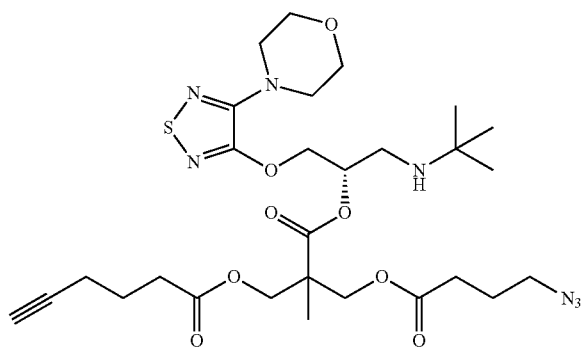 [SMILES: C#CCCCC(=O)OCC(C)(COC(=O)CCCN=[N+]=[N-])C(=O)O[C@@H](CNC(C)(C)C)COc1nsnc1N1CCOCC1] |
| 42 | As per Example 26 | 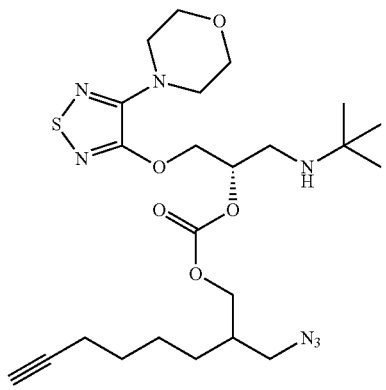 [SMILES: C#CCCCCC(CN=[N+]=[N-])COC(=O)O[C@@H](CNC(C)(C)C)COc1nsnc1N1CCOCC1] |

LTP = latanoprost
TVP = travoprost
TIM = timolol

Preparation of Polymer-Bioactive Agent Conjugates
Preparation of Co-Monomers
  Co-monomer Methods
  Method 6: Reaction of Alcohols with Isocyanates
  To a solution of isocyanate monomer (1 eq.) in anhydrous solvent is added the alcohol derivative (>2 eq.) and dibutyltin dilaurate (cat., ~0.05 eq). The reaction is stirred at rt under an argon atmosphere for 24 h or until the reaction is complete. The mixture is concentrated in vacuo to yield the desired product.
  Method 7: Azidation of Alkyl Halides, Alkyl Tosylates or Alkyl Mesylates
  To a solution of alkyl halide/tosylate/mesylate (1 eq.) in anhydrous DMF is added NaN$_3$ (5 eq.) and the reaction mixture stirred at 60° C. for 24 h or until the reaction is complete. The resultant precipitate was removed via filtration and the filtrate was concentrated in vacuo. The resulting residue is washed with DCM and filtered before concentrating in vacuo to give the desired product.
  Method 8: Reaction of Acid Chlorides with Alcohols or Amines
  To a solution of acid chloride (1 eq.) in anhydrous solvent at 0° C. is added an excess of the relevant alcohol or amine (≥2 eq.), DMAP and an appropriate amine base. The solution is allowed to gradually warm to rt and stirred for 48 h or until the reaction is complete. The crude reaction mixture is washed (0.1 M NaHCO$_3$, followed by 0.1 M HCl), dried (MgSO$_4$) and concentrated under reduced pressure.

Example 43

Synthesis of (S)-ethyl 2,6-bis(((3-azidopropoxy)carbonyl)amino)hexanoate

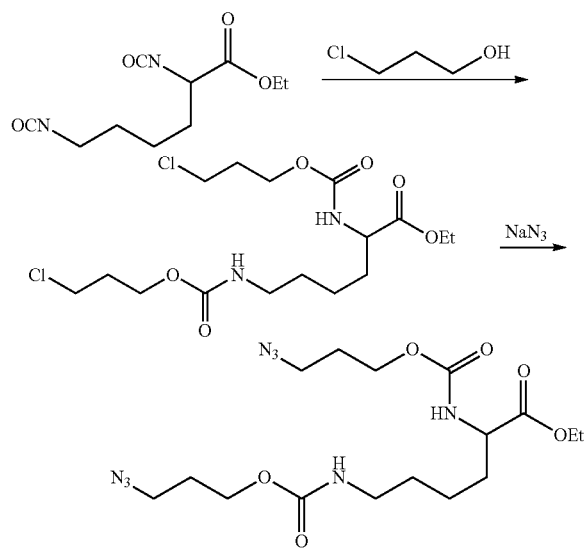

Ethyl 2,6-diisocyanatohexanoate (ELDI) (1.00 g, 4.42 mmol) and 3-chloro-1-propanol (1.04 g, 11.1 mmol) in anhydrous DCM (10 mL) were reacted in the presence of a catalytic amount of dibutyltin dilaurate according to the procedure described in Method 6 above to yield (S)-ethyl 2,6-bis(((3-chloropropoxy)carbonyl)amino)hexanoate as a clear oil (1.37 g, 3.30 mmol, 75%).

A solution of (S)-ethyl 2,6-bis(((3-chloropropoxy)carbonyl)amino)hexanoate (1.37 g, 3.31 mmol) and NaN$_3$ (1.07 g, 16.5 mmol) in DMF (20 mL) was reacted according to the procedure outlined in Method 7 above to give (S)-ethyl 2,6-bis(((3-azidopropoxy)carbonyl)amino)hexanoate as an oil (1.33 g, 3.10 mmol, 94%). $^1$H NMR (400 MHz, d$_1$-CDCl$_3$) δ$_H$ 1.28 (t, 3H, J=6.9 Hz), 1.39-1.72 (m, 6H), 1.81-1.93 (m, 4H), 3.15 (q, 2H, J=7.2 Hz), 3.36 (q, 4H, J=6.4 Hz), 4.13-4.23 (m, 6H), 4.29-4.34 (m, 1H), 4.72 (m, 1H), 5.26 (d, 1H, J=8.0 Hz).

Example 44

Synthesis of bis(3-azidopropyl) hexane-1,6-diyldicarbamate

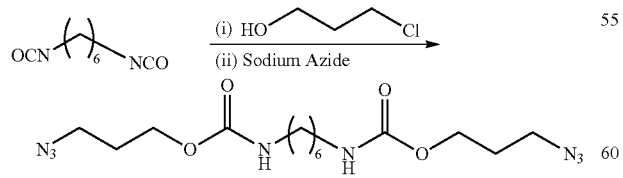

1,6-diisocyanatohexane (HDI) (2.00 g, 11.9 mmol) and 3-chloro-1-propanol (4.50 g, 47.5 mmol) in anhydrous DCM (20 mL) were reacted in the presence of a catalytic amount of dibutyltin dilaurate according to the procedure described in Method 6 above to yield bis(3-chloropropyl) hexane-1,6-diyldicarbamate as a clear oil (4.20 g, 11.8 mmol, 99%). A solution of bis(3-chloropropyl) hexane-1,6-diyldicarbamate (4.20 g, 11.8 mmol) and NaN$_3$ in DMF (20 mL) was reacted according to the procedure outlined in Method 7 above to give bis(3-azidopropyl) hexane-1,6-diyldicarbamate as a white solid (3.86 g, 10.4 mmol, 88%). $^1$H NMR (400 MHz, d$_1$-CDCl$_3$) δ$_H$ 1.32-1.35 (m, 4H), 1.48-1.52 (m, 4H), 1.85 (p, 4H, 6.8 Hz), 3.14 (q, 4H, J=6.8 Hz), 3.36 (t, 4H, J=6.4 Hz), 4.19 (t, 4H, J=6.0 Hz), 4.68 (t, 1H, J=0.8 Hz).

Example 45

Synthesis of 3-azidopropyl 2-azidoacetate

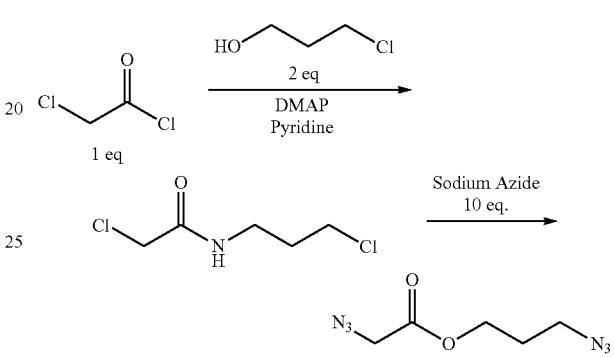

Chloroacetyl chloride (2.00 g, 17.7 mmol), was reacted with 3-chloro-1-propanol (3.35 g, 35.4 mmol), DMAP and pyridine (2.10 g, 26.5 mmol) in DCM (15 mL) according to the procedure outlined in Method 8 above. The crude material was purified by bulb-to-bulb distillation (65° C./0.5 Mbar) to yield 3-chloropropyl 2-chloroacetate as a clear oil (1.10 g, 6.43 mmol, 36%). A solution of 3-chloropropyl 2-chloroacetate (1.10 g, 6.43 mmol) and NaN$_3$ (4.18 g, 64.3 mmol) in DMF (20 mL) was reacted according to the general procedure outlined in Method 7 above to give the desired product 3-azidopropyl 2-azidoacetate.

Example 46

Synthesis of 2-azido-N-(3-azidopropyl)acetamide

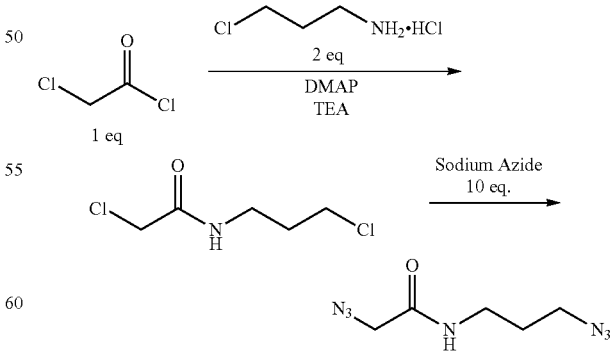

Chloroacetyl chloride (1.00 g, 8.85 mmol), was reacted with 3-chloro-1-propan-1-amine hydrochloride (2.30 g, 17.7 mmol), DMAP (54.1 mg, 0.443 mmol) and triethylamine (2.69 g, 26.6 mmol) in DCM (10 mL) according to the procedure outlined in Method 8 above to yield 2-chloro-N-(3-chloropropyl)acetamide as a clear oil (0.381 g, 2.24 mmol, 25%). A solution of 2-chloro-N-(3-chloropropyl)acetamide (0.381 g, 2.24 mmol) and $NaN_3$ (1.45 g, 22.4 mmol) in DMF (10 mL) was reacted according to the general procedure outlined in Method 7 above to give the desired product 2-azido-N-(3-azidopropyl)acetamide as a brownish oil (0.215 g, 1.17 mmol, 52%). $^1$H NMR (400 MHz, $d_1$-$CDCl_3$) $\delta_H$ 1.77 (p, 2H, J=6.4 Hz), 3.37 (m, 4H), 3.98 (s, 2H).

Example 47

Synthesis of (S)-ethyl 2,6-bis(((prop-2-yn-1-yloxy)carbonyl)amino)hexanoate

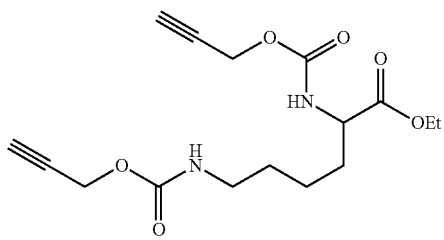 [SMILES: C#CCOC(=O)NCCCCC(NC(=O)OCC#C)C(=O)OCC]

Ethyl 2,6-diisocyanatohexanoate (ELDI) (1.00 g, 4.42 mmol) and propargyl alcohol (0.620 g, 11.0 mmol) in anhydrous DCM (10 mL) were reacted in the presence of a catalytic amount of dibutyltin dilaurate according to the procedure described in Method 6 above. The solution was passed through an aluminium oxide column before concentrating under reduced pressure to yield (S)-ethyl 2,6-bis(((prop-2-yn-1-yloxy)carbonyl)amino)hexanoate as a clear oil (1.24 g, 3.66 mmol, 83%). $^1$H NMR (400 MHz, $d_1$-$CDCl_3$) $\delta_H$ 1.25 (t, 3H, J=7.2 Hz), 1.39-1.83 (m, 6H), 2.45-2.48 (m, 2H), 3.15 (q, 2H, J=6.8 Hz), 3.36 (q, 4H, J=6.4 Hz), 4.16 (q, 2H, J=7.2 Hz), 4.28-4.33 (m, 1H), 4.65-4.68 (m, 4H), 4.94 (m, 1H), 5.47 (d, 1H, J=8.0 Hz)

Example 48

PEG3000-dilysine diazide co-monomer

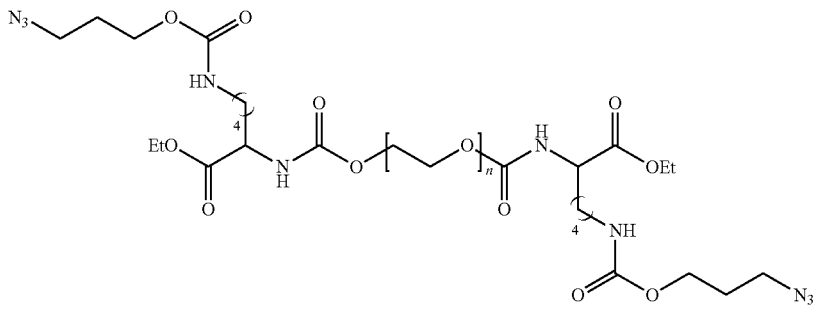

A mixture of ethyl 2,6-diisocyanatohexanoate (ELDI) (1.51 g, 6.67 mmol) and PEG3000 (2.0 g, 0.67 mmol) in anhydrous DCM (25 mL) was reacted according to the procedure outlined in Method 6. The crude material was precipitated several times in $Et_2O$ and dried in vacuo to give a PEG3000-dilysine dicarbamate intermediate product as a white solid (1.8 g). $^1$H NMR and MALDI-TOF analysis showed quantitative incorporation of ELDI onto both ends of PEG3000.

The above intermediate (0.726 g, 0.210 mmol) was treated with 3-chloropropanol (0.199 g, 2.10 mmol) in anhydrous DCM (50 mL) according to the procedure outlined in Method 6. The crude material was precipitated several times in $Et_2O$ and dried in vacuo to give the PEG3000-dilysine dichloropropanolintermediate as a white solid (0.710 g). $^1$H NMR and MALDI-TOF analysis confirmed the end group modifications.

The above dichloro intermediate (0.710 g, 0.223 mmol) was treated with $NaN_3$ (0.31 mg, 4.76 mmol) in DMF (20 mL) according to the procedure outlined in Method 7. The crude material was precipitated several times in $Et_2O$ and dried in vacuo to give the PEG3000-dilysine diazide tetracarbamate product as a white solid (0.539 g). $^1$H NMR and MALDI-TOF analysis confirmed the end group modifications.

Example 49

Synthesis of PEG3000-dilysine dipropargyl co-monomer

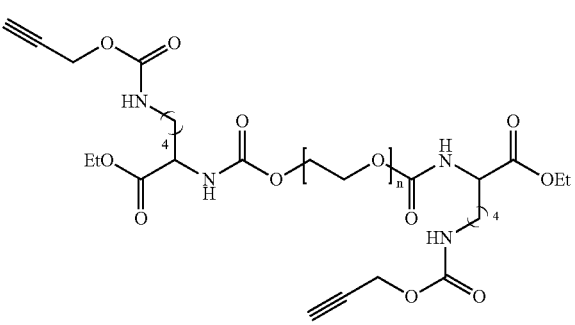

A mixture of the PEG3000-dilysine diisocyanate derivative described in Example 48 (1.0 g, 0.29 mmol) and propargyl alcohol (0.162 g, 2.89 mmol) in anhydrous DCM (50 mL) were reacted according to the procedure outlined in Method 6. The crude material was precipitated several times in $Et_2O$ and dried in vacuo to give the PEG3000-dilysine dipropargyl tetracarbamate product as a white solid (0.486 g). MALDI-TOF analysis confirmed the end group modifications.

Example 50

Preparation of poly(ethyleneglycol) bis(4-((3S,4S)-(3,4-dimethoxy)azacyclooct-5-yn-1-yl)-4-oxobutanoate)

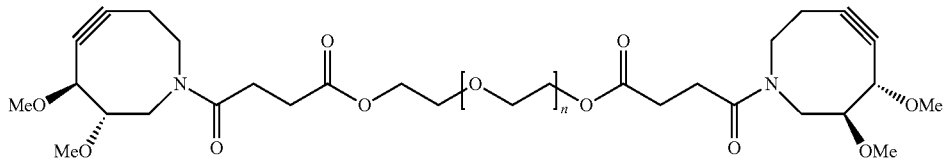

DCC (2.2 eq) can be added to a solution of a polyethylene glycol (1 eq), 4-((3S,4S)-(3,4-dimethoxy)azacyclooct-5-yn-1-yl)-4-oxobutanoic acid (2.5 eq) and DMAP (0.1 eq) in DCM in an analogous procedure to that described in Method 1a. Precipitation of the crude material can provide the title compound poly(ethyleneglycol) bis(4-((3S,4S)-(3,4-dimethoxy)azacyclooct-5-yn-1-yl)-4-oxobutanoate).

Example 51

Preparation of (S)-ethyl 2,6-bis(((((1R,8S,9r)-1,8-dimethylbicyclo[6.1.0]non-4-yn-9-yl)methoxy)carbonyl)amino)hexanoate

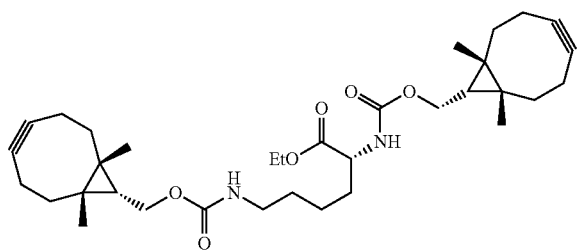

A solution of (S)-ethyl 2,6-diisocyanatohexanoate (1 eq), ((1R,8S,9r)-1,8-dimethylbicyclo[6.1.0]non-4-yn-9-yl) methanol (2.2 eq) and dibutyltin dilaurate (catalytic, ~0.05 eq.) in anhydrous DCM can be reacted according to the procedure outlined in Method 6. The solvent can be removed under reduced pressure and flash chromatography of the crude material can provide the title compound.

Example 52

Preparation of (S)-ethyl 2,6-bis((((1R,8S,9s)-bicyclo[6.1.0]non-4-yn-9-ylmethoxy)carbonyl)amino)hexanoate

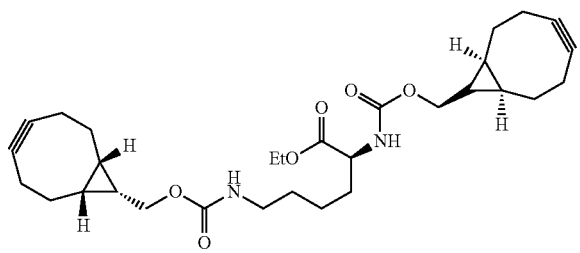

A solution of (S)-ethyl 2,6-diisocyanatohexanoate (1 eq), (1R,8S,9s)-bicyclo[6.1.0]non-4-yn-9-ylmethanol (2.2 eq) and dibutyltin dilaurate (catalytic, ~0.05 eq.) in anhydrous DCM can be reacted according to the procedure outlined in Method 6. The solvent can be removed under reduced pressure and flash chromatography of the crude material can provide the title compound.

Polymer Synthesis

Method 9: Copper Catalysed Click Reaction (a) Polymer Conjugate Prepared with Dialkyne-Bioactive Agent Conjugate Monomer The dialkyne-bioactive agent conjugate monomer (1 eq.) and a diazide co-monomer (1 eq.) are dissolved in the solvent of choice. The solution is purged with argon for 30 minutes before copper (II) bromide ($CuBr_2$) (0.05 mol eq.), PMDETA (0.05 mol eq.) and sodium ascorbate (0.15 mol eq.) are added into the solution. The heterogeneous mixture is stirred vigorously overnight under argon atmosphere and at room temperature for 24 hours. The reaction mixture is then passed through a column of basic alumina to remove the $CuBr_2$ catalyst, and then concentrated in vacuo before being precipitated several times in excess amount of diethyl ether to afford the desired polymer as solids. The polymer-bioactive agent conjugates are analysed by $^1$H NMR and $^{13}$C NMR and GPC.

(b) Polymer Conjugate Prepared with Diazide-Bioactive Agent Conjugate Monomer.

The diazide-bioactive agent conjugate monomer (1 eq.) and a dialkyne co-monomer (1 eq.) are dissolved in the solvent of choice. The solution is purged with argon for 30 minutes before copper (II) bromide ($CuBr_2$) (0.05 mol eq.), PMDETA (0.05 mol eq.) and sodium ascorbate (0.15 mol eq.) are added into the solution. The heterogeneous mixture is stirred vigorously overnight at room temperature until complete consumption of starting materials, as indicated by TLC. The mixture is diluted with water and any precipitate that forms is collected. Purification of the product by precipitation from DMF and further purification on Sephadex LH-20 gives the title polymer-bioactive agent conjugate. The polymer-bioactive agent conjugates are analysed by IR, $^1$H NMR and $^{13}$C NMR and GPC (c) Linear Click Polymer Conjugate Prepared with Dialkyne-Bioactive Agent Conjugate Monomer with Additives.

The dialkyne-bioactive agent conjugate monomer and diazide co-monomer 1 and co-monomer 2 are dissolved in the solvent of choice while keeping an equimolar ratio between the number of alkyne units and azide units. The solution is purged with argon for 30 minutes before copper (II) bromide ($CuBr_2$) (0.05 mol eq.), PMDETA (0.05 mol eq.) and sodium ascorbate (0.15 mol eq.) are added into the solution. The heterogeneous mixture is stirred overnight under argon atmosphere and at room temperature for 24 hours. The reaction mixture is then passed through a column of basic alumina to remove the $CuBr_2$ catalyst, and then concentrated in vacuo before being precipitated several times in excess of diethyl ether to afford the desired polymer a solid. The polymer-bioactive agent conjugates are analysed by $^1$H NMR and GPC.

(d) Polymer Conjugate Prepared with Alkyne-Azide-Bioactive Agent Conjugate Monomer (Drug Monomer Only)

The alkyne-azide bioactive agent conjugate monomer (1 eq.) is dissolved in the solvent of choice. The solution is purged with argon for 30 minutes before copper (II) bromide ($CuBr_2$) (0.05 mol eq.), PMDETA (0.05 mol eq.) and sodium ascorbate (0.15 mol eq.) are added into the solution. The heterogeneous mixture is stirred vigorously overnight until complete consumption of starting materials, as indicated by TLC. The mixture is diluted with water and any precipitate that forms is collected. Purification of the product by precipitation from DMF and further purification on Sephadex LH-20 gives the title polymer-bioactive agent conjugate. The polymer-bioactivea agent conjugates are analysed by IR, $^1$H NMR and $^{13}$C NMR and GPC (e) Polymer Conjugate Prepared with Alkyne-Azide-Bioactive Agent Conjugate Monomer (and Co-Monomer)

The alkyne-azide-bioactive agent conjugate monomer (1 eq.) and an alkyne-azide co-monomer (1 eq.) are dissolved in the solvent of choice. The solution is purged with argon for 30 minutes before copper (II) bromide ($CuBr_2$) (0.05 mol eq.), PMDETA (0.05 mol eq.) and sodium ascorbate (0.15 mol eq.) are added into the solution. The heterogeneous mixture is stirred vigorously overnight until complete consumption of starting materials, as indicated by TLC. The mixture is diluted with water and any precipitate that forms is collected. Purification of the product by precipitation from DMF and further purification on Sephadex LH-20 gives the title polymer-bioactive agent conjugate. The polymer-bioactivea agent conjugates are analysed by IR, $^1$H NMR and $^{13}$C NMR and GPC.

Method 10: Ruthenium-Catalyzed Click Reaction

The 1,5 disubstituted 1,2,3 triazole containing polymers can be formed using a procedure described in Zhang et al. *J. Am. Chem. Soc.,* 2005, 127 (46), pp 15998-15999.

(a) Polymer Conjugate Prepared with Dialkyne-Bioactive Agent Conjugate Monomer

The dialkyne-bioactive agent conjugate monomer (1 eq.), a diazide co-monomer (1 eq.) and Cp*RuCl(PPh$_3$)$_2$ is dissolved in the solvent of choice (benzene, THF, DMF or dioxane) and allowed to stir at 60-80° C. until reaction is complete. Progress of the reaction is monitored by $^1$H NMR or TLC. The mixture is diluted with water and any precipitate that forms is collected. Purification of the product by precipitation from diethyl ether and further purification on Sephadex LH-20 gives the title polymer-bioactive agent conjugate. The polymer-bioactive agent conjugates are analysed by IR, $^1$H NMR and $^{13}$C NMR and GPC.

(b) Polymer Conjugate Prepared with Diazide-Bioactive Agent Conjugate Monomer

The diazide-bioactive agent conjugate monomer (1 eq.) and a dialkyne co-monomer (1 eq.) and Cp*RuCl(PPh$_3$)$_2$ are dissolved in the solvent of choice (benzene, THF, DMFor dioxane) and allowed to stir at 60-80° C. until reaction is complete. Progress of the reaction is monitored by $^1$H NMR or TLC. The mixture is diluted with water and any precipitate that forms is collected. Purification of the product by precipitation from diethyl ether and further purification on Sephadex LH-20 gives the title polymer-bioactive agent conjugate. The polymer-bioactive agent conjugates are analysed by IR, $^1$H NMR and $^{13}$C NMR and GPC.

(c) Polymer Conjugate Prepared with Azide-Alkyne-Bioactive Agent Conjugate Monomer The azide-alkyne-bioactive agent conjugate monomer and Cp*RuCl(PPh$_3$)$_2$ are dissolved in the solvent of choice (benzene, THF, DMF or dioxane) and allowed to stir at 60-80° C. until reaction is complete. Progress of the reaction is monitored by $^1$H NMR or TLC. The mixture is diluted with water and any precipitate that forms is collected. Purification of the product by precipitation from diethyl ether and further purification on Sephadex LH-20 gives the title polymer-bioactive agent conjugate. The polymer-bioactive agent conjugates are analysed by IR, $^1$H NMR and $^{13}$C NMR and GPC.

Method 11: Strain Promoted Azide Alkyne Cycloaddition a) Polymer Conjugate Prepared with Dicycloalkyne-Bioactive Agent Conjugate Monomer and Diazide Co Monomer The dicycloalkyne-bioactive agent conjugate monomer substrate and the diazide monomer substrate can be dissolved separately in a solvent ($CH_3CN$ or DMF) and mixed in a 1:1 ratio. The reaction mixture can be stirred for 12 h at room temperature. The mixture may be diluted with water and any precipitate formed collected. Purification of the product by precipitation from DMF and diethyl ether and further purification on Sephadex LH-20 will give the title polymer-bioactive agent conjugate.

b) Polymer Conjugate Prepared with Diazide-Bioactive Agent Conjugate Monomer and Dialkyne (Cyclooctyne) Co-Monomer A diazide-bioactive agent conjugate monomer and a dicycloalkyne co-monomer can be dissolved separately in solvent ($CH_3CN$ or DMF) and reacted using the same procedure as described for Method 12 a)

Using the above methods the following polymers in Table 5 were prepared.

TABLE 5

Examples of Click Polymers

| Example | Drug | Drug-monomer 1 (mg) | Drug-monomer 2 (mg | Co-Monomer 1 (mg) | Co-Monomer 2 (mg) | Production Method (solvent) | Characterisation |
|---|---|---|---|---|---|---|---|
| 53 | LTP | 13 (23) | — | ELDN$_3$ (14.1) | | 9(a) (DMF) | Mw = 24.5 kDa, PDI = 1.33 solid (25 mg) |
| 54 | LTP | 12 (108) | — | ELDN3 (87.4) | | 9(a) (DMF) | Mw = 36.5 kDa, PDI = 1.57, solid (101.9 mg) |

TABLE 5-continued

Examples of Click Polymers

| Example | Drug | Drug-monomer 1 (mg) | Drug-monomer 2 (mg) | Co-Monomer 1 (mg) | Co-Monomer 2 (mg) | Production Method (solvent) | Characterisation |
|---|---|---|---|---|---|---|---|
| 55 | LTP | 12 (108) | — | ELDN$_3$ (78.6) | PEG3000 diN$_3$ (65.5) | 9(a) (DMF) | Mw = 36.2 kDa, PDI = 1.61 solid (137.1 mg) |
| 56 | LTP | 13 (113) | — | ELDN$_3$ (69.8) | | 9(a) (DMF) | Mw = 72.3 kDa, PDI = 2.20 Solid (151 mg) |
| 57 | LTP | 17 (100) | — | ELDN$_3$ (72.7) | | 9(a) (DMF) | Mw = 14.7 kDa, PDI = 1.39 foam (106 mg) |
| 58 | LTP | 17 (100) | — | ELDN$_3$ (65.4) | PEG3000 diN$_3$ (54.4) | 9(b) (DMF) | Mw = 35.5 kDa, PDI = 1.14 solid (150 mg) |
| 59 | LTP | 13 (150) | — | ELDN$_3$ (91.9) | | 9(a) (DMF)) | Mw = 71.3 kDa, PDI = 2.29 foam (211 mg) |
| 60 | LTP | 12 (101.4) | — | ELDN3 (73.8) | PEG400diN$_3$ (9.92) | 9(b) (DMF) | Mw = 13.9 kDa, PDI = 1.32 foam |
| 61 | LTP | 12 (100.7) | — | ELDN3 (40.7) | PEG400diN$_3$ (49.2) | 9(b) (DMF) | Mw = 26.9 kDa, PDI = 1.65 foam |
| 62 | LTP | 12 (94.8) | — | HDN$_3$ (71.0) | | 9(a) (DMF) | Mw = 37.7 kDa, PDI = 1.83 foam |
| 63 | LTP | 19 (100) | — | ELDN$_3$ (62.8) | | 9(a) (DMF) | Mw = 6.85 kDa, PDI = 1.10 solid |
| 64 | LTP | 14 (88.5) | — | — | PEG400diN$_3$ (69.6) | 9(a) (DMF) | Mw = 13.9 kDa, PDI = 1.32 soft green tacky solid |
| 65 | LTP | 17 (96) | — | | PEG400diN$_3$ (84.4) | 9(a) (DMF) | Mw = 15.5 kDa, PDI = 1.37 solid |
| 66 | LTP | 20 (51.5) | — | | PEG400diN$_3$ (42.9) | 9(a) (DMF) | Mw = 27.4 kDa, PDI = 1.67 solid |
| 67 | LTP | 21 (83.4) | — | | PEG400diN$_3$ (57.6) | 9(a) (DMF) | Mw = 28.1 kDa, PDI = 1.68 solid |
| 68 | LTP | 18 (78.2) | — | | PEG400diN$_3$ (51.4) | 9(a) (DMF) | Mw = 20.6 kDa, PDI = 1.48 solid |
| 69 | LTP and Timolol | 13 (52.5) | Tim-O-carbonate-dialkyne 26 (37.3) | | PEG400diN$_3$ (77.8) | 9(a) (DMF) | Mw = 18.0 kDa, PDI = 1.42 solid |
| 70 | LTP | 13 (82.9) | — | | PEG400diN$_3$ (61.5) | 9(a) (DMF) | Mw = 21.3 kDa, PDI = 1.51 solid |
| 71 | TVP | 23 (70) | — | | PEG400diN$_3$ (54.7) | 9(a) (DMF) | Mw = 21.3 kDa, PDI = 1.52 solid |
| 72 | LTP | 15 (68.2) | — | | PEG400diN$_3$ (45.2) | 9(a) (DMF) | Mw = 21.5 kDa, PDI = 1.51 solid |
| 73 | Timolol | 27 (100) | — | ELDN$_3$ (98.6) | | 9(a) (DMF) | Mw = 26.9 kDa, PDI = 1.64 |
| 74 | LTP | 14 (100) | — | ELDN$_3$ (69.7) | | 9(a) (DMF) | Mw = 51.3 kDa, PDI = 2.00 |
| 75 | LTP and Timolol | 18 (55.3) | Tim-O-ester-dialkyne 27 (32.6) | ELDN$_3$ (64.3) | | 9(a) (DMF) | Mw = 9.83 kDa, PDI = 1.15 |
| 76 | LTP | 14 (100) | — | HDN$_3$ (60.3) | | 9(a) (DMF) | Mw = 84.1 kDa, PDI = 2.09 |
| 77 | Timolol | 26 (144) | — | ELDN$_3$ (124) | | 9(a) (DMF) | Mw = 36.5 kDa, PDI = 1.20 foam |

Using the above methods the following polymers may also be prepared.

| Example | Drug | Drug-monomer conjugate | Co-Monomer 1 | Co-Monomer 2 | Method of Synthesis (solvent) |
|---|---|---|---|---|---|
| 78 | LTP | 12 | N₃ with OH, OH, OH substituents and N₃ terminus | | 9(a) (DMF) |
| 79 | LTP | 12 | N₃-(CH₂CH₂O)ₙ-N₃ | — | 10(a) (DMF) |
| 80 | LTP | 18 | Isosorbide bis(azidoacetate) | — | 10(a) (DMF) |
| 81 | LTP | 38 | Bis(propargyl) glutarate | — | 9(b) (DMF) |
| 82 | LTP | 38 | Bis(propargyl) glutarate | — | 10(b) (DMF) |
| 83 | LTP | 12 | Propane-1,3-diyl bis(2-azidoacetate) | PEG 3000 diN₃ | 9(c) (DMF) |
| 84 | LTP | 37 | 2-(azidomethyl)-2-methyl-3-hydroxypropyl hex-5-ynoate | — | 9(e) (DMF) |
| 85 | LTP | 37 | — | | 9(d) (DMF) |
| 86 | LTP | 37 | Lysine derivative with N₃-propyl carbamate and propargyl carbamate, EtO ester | | 9(e) (DMF) |
| 87 | TIM LTP | 40 | 37 | — | 9(e) (DMF) |
| 88 | TVP | 22 | 43 | — | 9(a) (DMF) |
| 89 | TVP | 23 | 43 | — | 9(a) (DMF) |
| 90 | TVP | 35 | 43 | — | 9(a) (DMF) |
| 91 | LTP | 33 | 43 | — | 9(a) (DMF) |
| 92 | LTP | 34 | 43 | — | 11(a) (DMF) |

| Example | Drug | Drug-monomer conjugate | Co-Monomer 1 | Co-Monomer 2 | Method of Synthesis (solvent) |
|---|---|---|---|---|---|
| 93 | LTP | 38 | (structure) | — | 11(b) (DMF) |
| 94 | LTP | 31 | (structure) | — | 11(b) (DMF) |

Drug Release Method

Polymer samples were tested for in vitro drug release following guidelines recommended by the International Organisation of Standardisation. The samples were placed onto a wire mesh folded into an M shape and suspended in isotonic phosphate buffer (IPB) pH 7.4 or pH 8.4 (Table 1), and stirred at 37° C. Aliquots of the receptor solution were collected at pre-determined time points until the drug was depleted from the polymer.

The amount of drug in the aliquots was quantified by reverse phase high performance liquid chromatography (HPLC) coupled with UV detection. Analytes were separated on a C18 column with a solvent mixture of acetonitrile and phosphate buffer (Latanoprost: acetonitrile and phosphate buffer pH 2.5, Latanoprost free acid: acetonitrile and phosphate buffer pH 5.0) or acetonitrile and water with triethylamine and phosphoric acid (Timolol). The rate of drug release from various polymers is shown in Table 6. It is anticipated that the other polymer-drug conjugates of the invention will release drug in a similar fashion.

TABLE 6

Drug release from polymers.

| Example no. | Buffer pH for release study | Release study Drug | Rate [μg/10 mg/24 hrs] |
|---|---|---|---|
| 54 | 7.4 | Latanoprost | 0.59 |
|  | 8.4 | free acid | 2.10 |
| 55 | 7.4 | Latanoprost | 1.91 |
|  | 8.4 | free acid | 4.91 |
| 56 | 7.4 | Latanoprost free acid | 0.85 |
| 60 | 7.4 | Latanoprost free acid | 2.27 |
| 61 | 7.4 | Latanoprost free acid | 5.05 |
| 62 | 7.4 | Latanoprost free acid | 1.68 |
| 77 | 7.4 | Timolol | 1527 |
| 64 | 7.4 | Latanoprost | 58.73 |
|  | 8.4 | free acid | 135.23 |
| 67 | 8.4 | Latanoprost | 1.55 |
| 70 | 7.4 | Latanoprost | 16.48 |
|  | 8.4 | free acid | 47.51 |
| 72 | 7.4 | Latanoprost free acid | 36.37 |

It is to be understood that various other modifications and/or alterations may be made without departing from the spirit of the present invention as outlined herein.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A polymer-bioactive agent conjugate comprising:
  a polymer backbone comprising a plurality of triazole moieties; and
  a plurality of releasable bioactive agents covalently bonded to and pendant from the polymer backbone,
  wherein the bioactive agents are selected from the group consisting of prostaglandin analogues, β-blockers, and mixtures thereof.

2. The polymer-bioactive agent conjugate according to claim 1, which is a copolymer of at least one monomer of formula (IV):

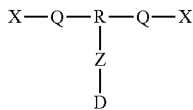
(IV)

where:
X may be the same or different at each occurrence and represents a terminal functional group comprising an alkyne or an azide;
Q is independently selected at each occurrence and may be present or absent and when present, represents a linking group;
R is an optionally substituted linear or branched hydrocarbon and may comprise optionally substituted aromatic hydrocarbon or heteroaromatic hydrocarbon;
Z is a cleavable linking group; and
D is one of the plurality of releasable bioactive agents and is selected from the group consisting of prostaglandin analogues and β-blockers;
and a monomer of formula (V):

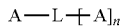
(V)

where:
A may be the same or different at each occurrence and represents a group comprising a terminal functional group comprising an alkyne or an azide functionality, wherein said terminal functional group is complementary to the terminal functional group of X;
L is an optionally substituted linker group; and
n is an integer and is at least 1.

3. The polymer-bioactive agent conjugate according to claim 2, comprising a moiety of formula (I):

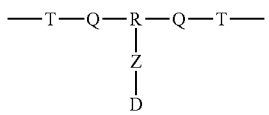
(I)

where:
T at each occurrence represents a triazole moiety;
Q is independently selected at each occurrence and may be present or absent and when present represents a linking group;
R is an optionally substituted linear or branched hydrocarbon and may comprise optionally substituted aromatic hydrocarbon or heteroaromatic hydrocarbon;
Z is a cleavable linking group; and
D is one of the plurality of releasable bioactive agents.

4. The polymer-bioactive agent conjugate according to claim 1, comprising a moiety of formula (Ib):

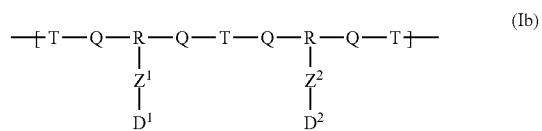
(Ib)

where:
T at each occurrence represents a triazole moiety;
Q is independently selected at each occurrence may be present or absent and when present represents a linking group;
R is an optionally substituted linear or branched hydrocarbon and may include optionally substituted aromatic hydrocarbon and heteroaromatic hydrocarbon;
$Z^1$ and $Z^2$ are each cleavable linking groups that may be the same or different; and
$D^1$ and $D^2$ are each one of the plurality of releasable bioactive agents and may be the same or different.

5. The polymer-bioactive agent conjugate according to claim 3, wherein the polymer backbone comprises at least one triazole moiety selected from the group consisting of formula (II), (III) and (IX):

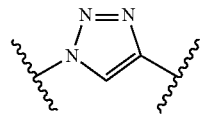
(II)

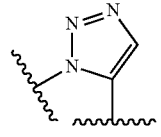
(III)

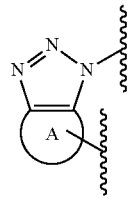
(IX)

wherein, in formula (IX), A is an optionally substituted cyclic group.

6. The polymer-bioactive agent conjugate according to claim 3, wherein the polymer backbone comprises at least one moiety selected from formula (IIa) and (IIb):

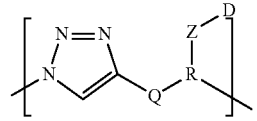
(IIa)

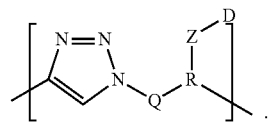
(IIb)

7. The polymer-bioactive agent conjugate according to claim 3, wherein the polymer backbone comprises at least one moiety selected from formula (IIIa) and (IIIb):

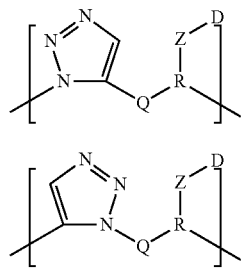

8. The polymer-bioactive agent conjugate according to claim 2, wherein the conjugate comprises a bioactive agent which is a prostaglandin analogue, wherein the prostaglandin analogue is conjugated to the polymer backbone at a position selected from the 1, 9, 11 and 15 position of the prostaglandin analogue.

9. The polymer-bioactive agent conjugate according to claim 8, wherein the prostaglandin analogue is conjugated to the polymer backbone via an ester, anhydride or carbonate linking group.

10. The polymer-bioactive agent conjugate according to claim 8, wherein the prostaglandin analogue is of formula (X):

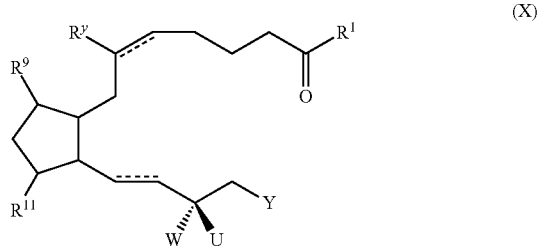

where:
  ----- represents a double or single bond;
  W and U are selected from the group consisting of where W and U together form oxo (=O), where W and U are each halo, and where W is $R^{15}$ and U is hydrogen;
  $R^y$ is an optional substituent selected from the group consisting of oxo and hydroxy;
  Y is optionally substituted to $C_4$ to $C_{10}$ hydrocarbyl or optionally substituted $C_4$ to $C_{10}$ hydrocarbyloxy; and
  one of $R^1$, $R^9$, $R^{11}$ and $R^{15}$ is linked to the polymer backbone and wherein:
  $R^9$, $R^{11}$ and $R^{15}$ when linked to the polymer backbone are the alcohol residue of an ester or carbonate linking group and $R^1$ when linked to the polymer backbone forms the acid residue of an ester or anhydride linking group; and
  $R^1$ when not linked to the backbone is selected from the group consisting of —OH, —O($C_{1-6}$ alkyl), and —$NR^aR^b$ where $R^a$ and $R^b$ are each independently selected from the group consisting of H and $C_{1-6}$ alkyl;
  $R^9$ and $R^{11}$ when not linked to the polymer backbone are each hydroxy or where one of $R^9$ and $R^{11}$ is linked to the backbone, the other is hydroxy; and when $R^{15}$ is not linked to the backbone then W is hydroxy and U is hydrogen, or W and U are each fluoro, or W and U together form oxo.

11. The polymer-bioactive agent conjugate according to claim 2, wherein the conjugate comprises a bioactive agent which is a β-blocker.

12. The polymer-bioactive agent conjugate according to claim 11, wherein the β-blocker comprises a beta-amino alcohol group and is conjugated to the polymer backbone via an ester or carbonate linking group formed with the alcohol moiety of the beta-amino alcohol group.

13. The polymer-bioactive agent conjugate according to claim 11, wherein the bioactive agent is a β-blocker of formula (XX):

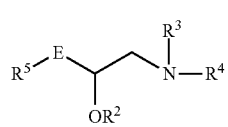

wherein:
  E is a bond or —$OCH_2$— (preferably —$OCH_2$—);
  $R^2$ is linked to the polymer backbone and is the alcohol residue of an ester or carbonate linking group;
  $R^3$ and $R^4$ are each independently selected from the group consisting of H, and linear or branched $C_1$-$C_4$ alkyl optionally substituted by one or more substituents selected from the group consisting of hydroxy, optionally substituted alkoxy, optionally substituted aryloxy, optionally substituted amido, optionally substituted cycloalkyl, and optionally substituted aryl; and
  $R^5$ is an optionally substituted cycloalkyl or aryl moiety.

14. The polymer-bioactive agent conjugate according to claim 2, wherein the triazole moieties constitute at least 10 mol % of the polymer backbone.

15. The polymer-bioactive agent conjugate according to claim 2, wherein in the monomer of formula (V), L comprises a linker moiety selected from the group consisting of optionally substituted linear or branched aliphatic hydrocarbon, optionally substituted carbocyclyl, optionally substituted heterocyclyl, optionally substituted aryl, optionally substituted heteroaryl, and an optionally substituted polymeric segment.

16. The polymer-bioactive agent conjugate according to claim 15, wherein L comprises a linking moiety comprising a biodegradable polymer.

17. The polymer-bioactive agent conjugate according to claim 16 wherein the biodegradable polymer comprises at least one biodegradable moiety selected from the group consisting of an ester, an amide, a urethane, a urea and a disulfide moiety.

18. The polymer-bioactive agent conjugate according to claim 2, wherein in the monomer of formula (V), L comprises a polymer selected from the group consisting of a polyether, a polyester, a polyurethane, and copolymers thereof.

19. The polymer-bioactive agent conjugate according to claim 2, wherein in the monomer of formula (V), n is 1, 2, or 3.

20. The polymer-bioactive agent conjugate according to claim 2, wherein the monomer of formula (V), L comprises a functional group selected from the group consisting of an amide, ether, ester, urethane, urea and carbonate ester.

21. The polymer-bioactive agent conjugate according to claim 2, wherein in the monomer of formula (IV), Q is present and each Q-X is independently selected from the following group:

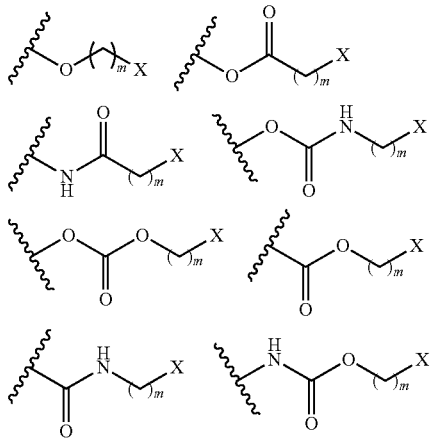

wherein m is an integer in the range of from 0 to 10.

22. The polymer-bioactive agent conjugate according to claim 2, wherein in the monomer of formula (IV), each Q-X is a group of formula (VII):

(VII)

where:
X is a terminal functional group comprising an alkyne or an azide functionality; and
m is an integer in the range of from 0 to 10.

23. The polymer-bioactive agent conjugate according to claim 2, wherein in the monomer of formula (IV), R is an optionally substituted aromatic hydrocarbon or heteroaromatic hydrocarbon.

24. An ocular implant for the treatment of glaucoma comprising the polymer-bioactive agent conjugate of claim 2.

* * * * *